(12) United States Patent
Solomon

(10) Patent No.: US 8,296,116 B2
(45) Date of Patent: Oct. 23, 2012

(54) BIOINFORMATICS SYSTEM

(76) Inventor: Neal Solomon, Oakland, CA (US)

( * ) Notice: Subject to any disclaimer, the term of this patent is extended or adjusted under 35 U.S.C. 154(b) by 0 days.

(21) Appl. No.: 12/012,004

(22) Filed: Jan. 30, 2008

(65) Prior Publication Data

US 2011/0131027 A1    Jun. 2, 2011

(51) Int. Cl.
*G06G 7/58* (2006.01)

(52) U.S. Cl. ............... 703/11; 700/30; 702/19; 707/769

(58) Field of Classification Search .................. None
See application file for complete search history.

(56) References Cited

U.S. PATENT DOCUMENTS 6,813,615 B1 * 11/2004 Colasanti et al. ............... 706/46

OTHER PUBLICATIONS

Peleg et al. "Qualitative Models of Molecular Function: Linking Genetic Polymorphisms of tRNA to Their Functional Sequelae", 2002, Proceedings of the IEEE, vol. 90, No. 12, pp. 1875-1886.*

* cited by examiner

*Primary Examiner* — Carolyn L. Smith

(57) ABSTRACT

The invention develops models of functional proteomics. Simulation scenarios of protein pathway vectors and protein-protein interactions are modeled from limited information in protein databases. The system focuses on three integrated subsystems, including (1) a system to model protein-protein interactions using an evolvable Global Proteomic Model (GPM) of functional proteomics to ascertain healthy pathway operations, (2) a system to identify haplotypes customized for specific pathology using dysfunctional protein pathway simulations of the function of combinations of single nucleotide polymorphisms (SNPs) so as to ascertain pathology mutation sources and (3) a pharmacoproteomic modeling system to develop, test and refine proposed drug solutions based on the molecular structure and topology of mutant protein(s) in order to manage individual pathologies. The system focuses on simulating the degenerative genetic disease categories of cancer, neurodegenerative diseases, immunodegenerative diseases and aging. The system reveals approaches to reverse engineer and test personalized medicines based upon dysfunctional proteomic pathology simulations.

20 Claims, 45 Drawing Sheets

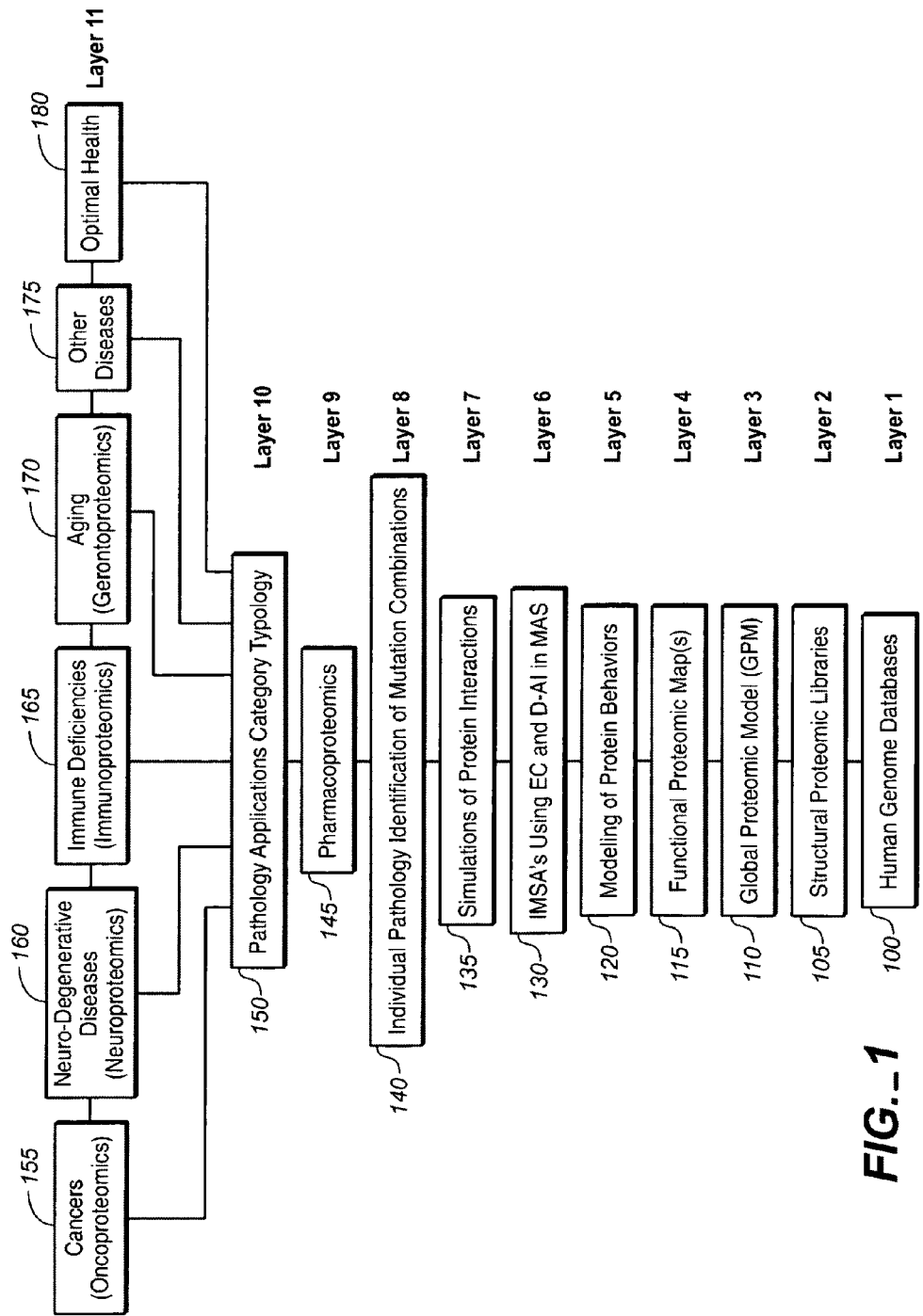
FIG._1

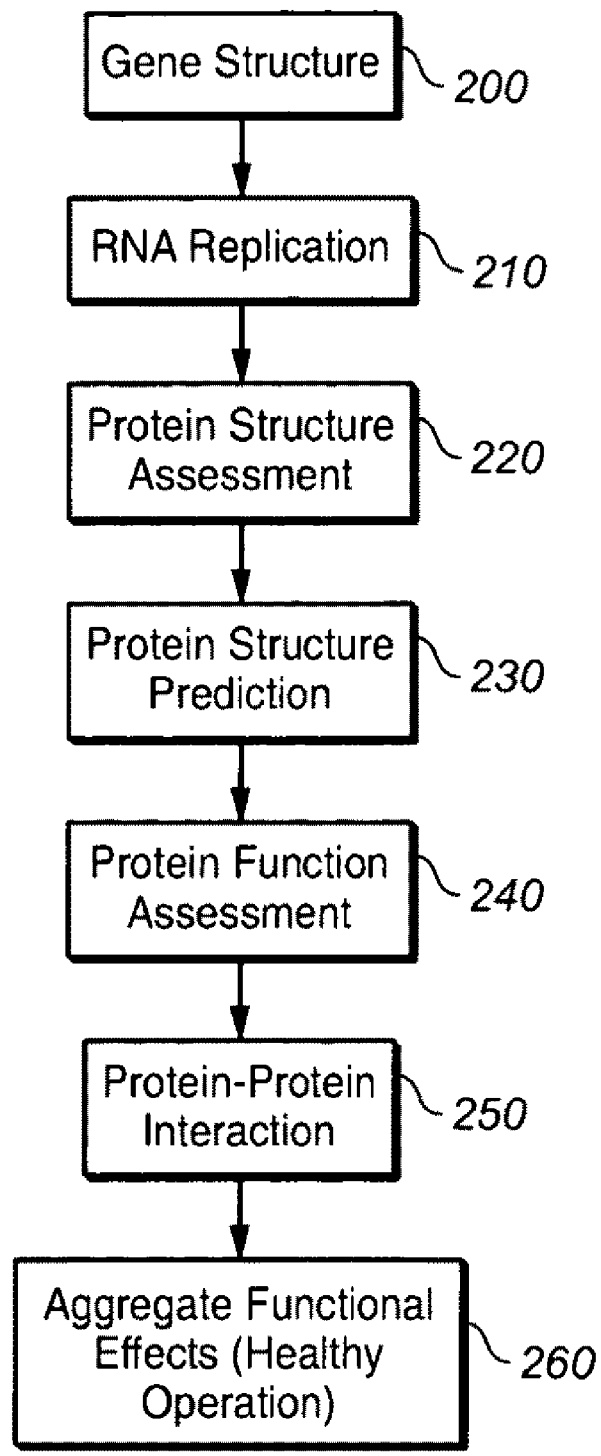
FIG._2

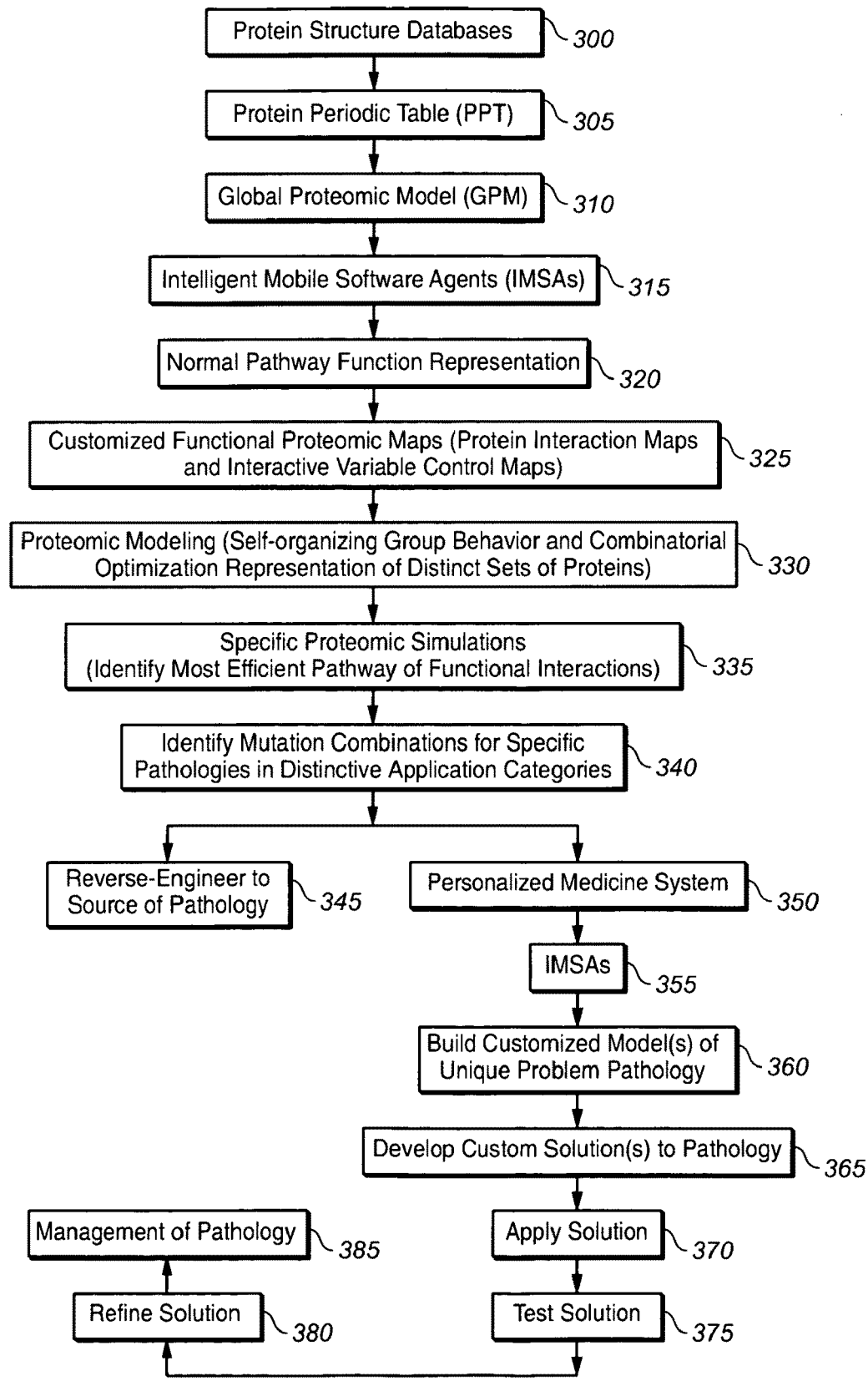
FIG._3

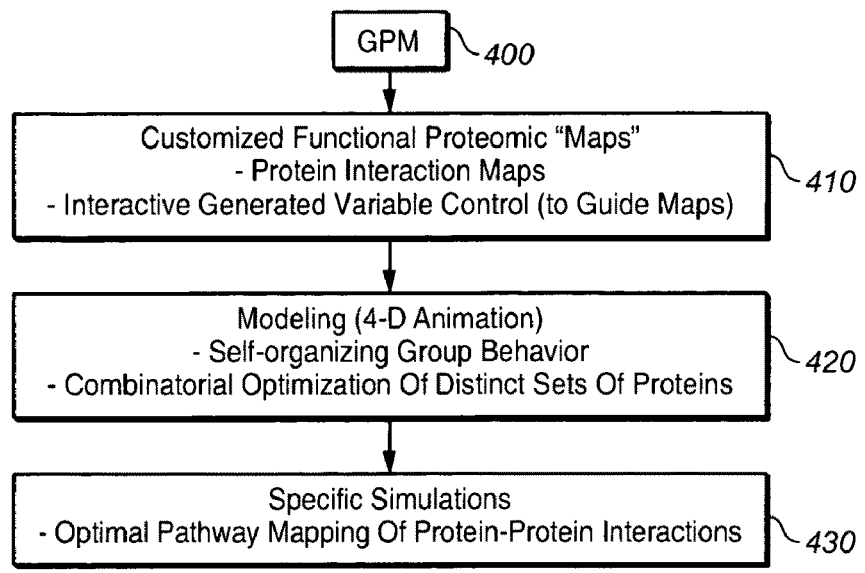
FIG._4
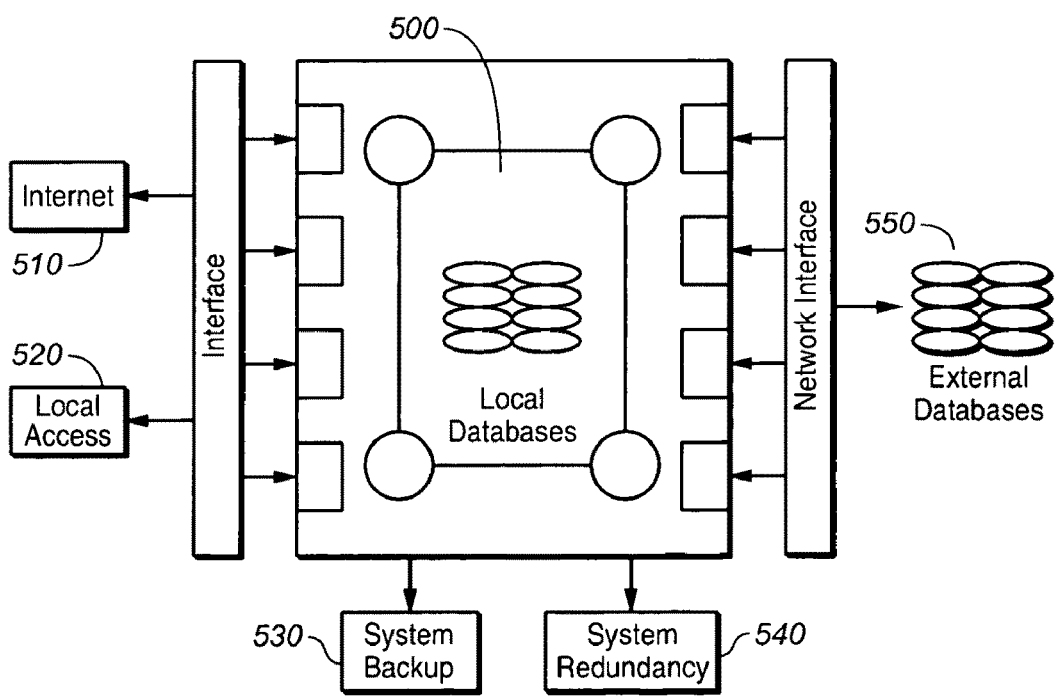
FIG._5

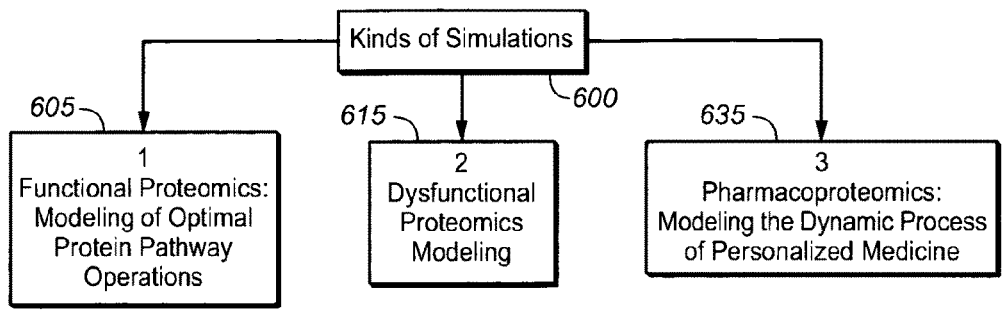
FIG._6
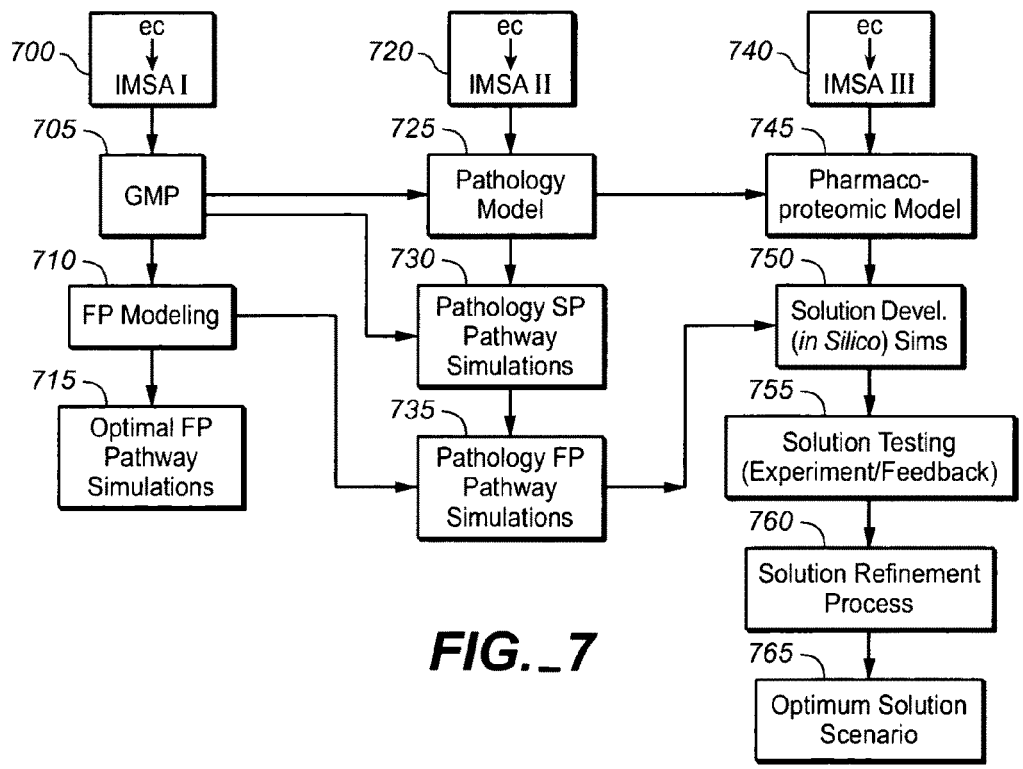
FIG._7

|  | Model Type | Data Source |
|---|---|---|
| 1st Level | Raw Data | Protein Databases |
| 2nd Level<br>(View of Protein)<br>2-D | Individual Protein Groupings | Protein Databases<br>- Initial Organization<br>(Protein Structure Prediction) |
| 3rd Level<br>(Protein and<br>Predisposition)<br>3-D | PPT<br>-Relations of Protein<br>-Evolutionary Origins | Protein Structure<br>- Protein Properties Organized |
| 4th Level<br>(Protein<br>Operation/Function/<br>Interaction)<br>4-D | GPM<br><br>Dynamic System Interaction<br>-Dynamic Sims/Modeling<br>using ISMAs<br>-Multivariate Analysis to<br>Simulate and Accelerate<br>Experiments | Functional Proteomic Model<br>- Protein Conditions<br>- Protein Interaction<br>Potentials |

FIG._8

| | Binding<br>(48.1%) | | Activities<br>(38%) | | |
|---|---|---|---|---|---|
| Protein<br>Function/<br>Protein<br>Structure | General<br>Binding<br>(37.5%) | Chemical<br>Binding<br>(10.6%) | Specialized<br>Activities<br>(30%) | Electron<br>Transport<br>Activity (8%) | Misc. |
| A | | | | | |
| Complexity  B | | | | | |
| A/B | | | | | |
| Composite | | | | | |
| Protein Family<br>Classification<br>Organizational Scheme | | | | | |

FIG._9

| Binding (48.1%) | Activities (38%) | Misc (13%) |
|---|---|---|
| DNA Binding (13.26%) | Oxidoreductose Activity (6.8%) | (13%) other |
| Protein Binding (18.1%) | Electron Transport (4.8%) | |
| ATP Binding (6.63%) | Catalytic Activity (4.4%) | |
| RNA Binding (4.95%) | Structural Molecule Activity (3.84%) | |
| Nucleic Acid Binding (4.58%) | Electron Transporter Activity (3.4%) | |
| Calcium Ion Binding (3.58%) | Receptor Activity (2.84%) | |
| Magnesium Ion Binding (3.53%) | Hydrolase Activity (on Glycosyl Bonds) (2.42%) | |
| Zinc Ion Binding (3.47%) | Endonuclease Activity (2.26%) | |
| | Signal Transducer Activity (2.26%) | |
| | Protein Kinase Activity (2.1%) | |
| | Nuclease Activity (2.05%) | |
| | Serine-type Endopeptibase Inhibitor Activity (1.84%) | |

*FIG._10*

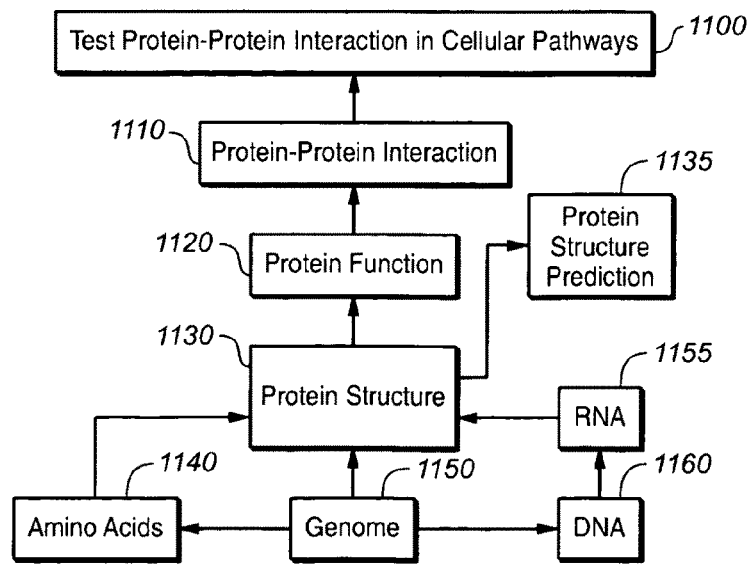

*FIG._11*

| Structural Proteomics | Functional Proteomics |
|---|---|
| (3-D)<br><br>"Prediction" of Protein Structure<br><br>Representation of Conditions of Individual Proteins | (4-D)<br><br>Representation of Forward Sequence of Protein's Operation<br><br>Representation of Backward Sequence of Protein's Operation to Cause<br><br>Representation of Reaction of Protein Operation<br><br>Representation of Optimal Protein-Protein Interactions<br><br>Representation of Sub-optimal Protein-Protein Interactions |

FIG._12

```
Chemical         Carbon
                 Hydrogen
                 Nitrogen
                 Oxygen
                 Phosphorus
                 Sulphur Electron Charge  Electron Binding Energies
                 Ionization Energies
                 Nuclear Charges
                 Electronegativities Temperature ph
```

FIG._13

```
Geometric Surface Shape Type
Protein Fold Type
Amino Acid Aggregate Configuration Type
Combinatorial Geometry
(Possible Aggregation Combinations)
Protein Structure Conditions
Extra-equilibrium Forms
```

FIG._14

| Optimal Conditions | Sub-optimal Conditions | Post-optimal Conditions |
|---|---|---|
| Binding<br>Transport<br>Regulate<br>Signaling<br>Receptor<br>Target<br>Inhibitor<br>Disruption | | |

*FIG._15*

- Narrow Range of Proteins that Combine with Other Proteins to Perform Specific Function
- Narrow Range of Protein <u>Networks</u> with Specific Functions
- Narrow Range of Macromolecular Assemblies of Interacting Proteins
- Specify Cellular Pathways with Specific Range of Protein Functions
- Specify Nearest Neighbor Protein Interaction
- Narrow Range of Proteins that Do <u>Not</u> Combine with Other Specific Classes of Proteins

*FIG._16*

Discreet Event Isolation

Threshold Event Identification

Time Release Aspect of Protein Pathway Sequence

Statistical Trial and Error as Key Method for Protein Inter-operation Compatibility in Cellular Pathways

*FIG._17*

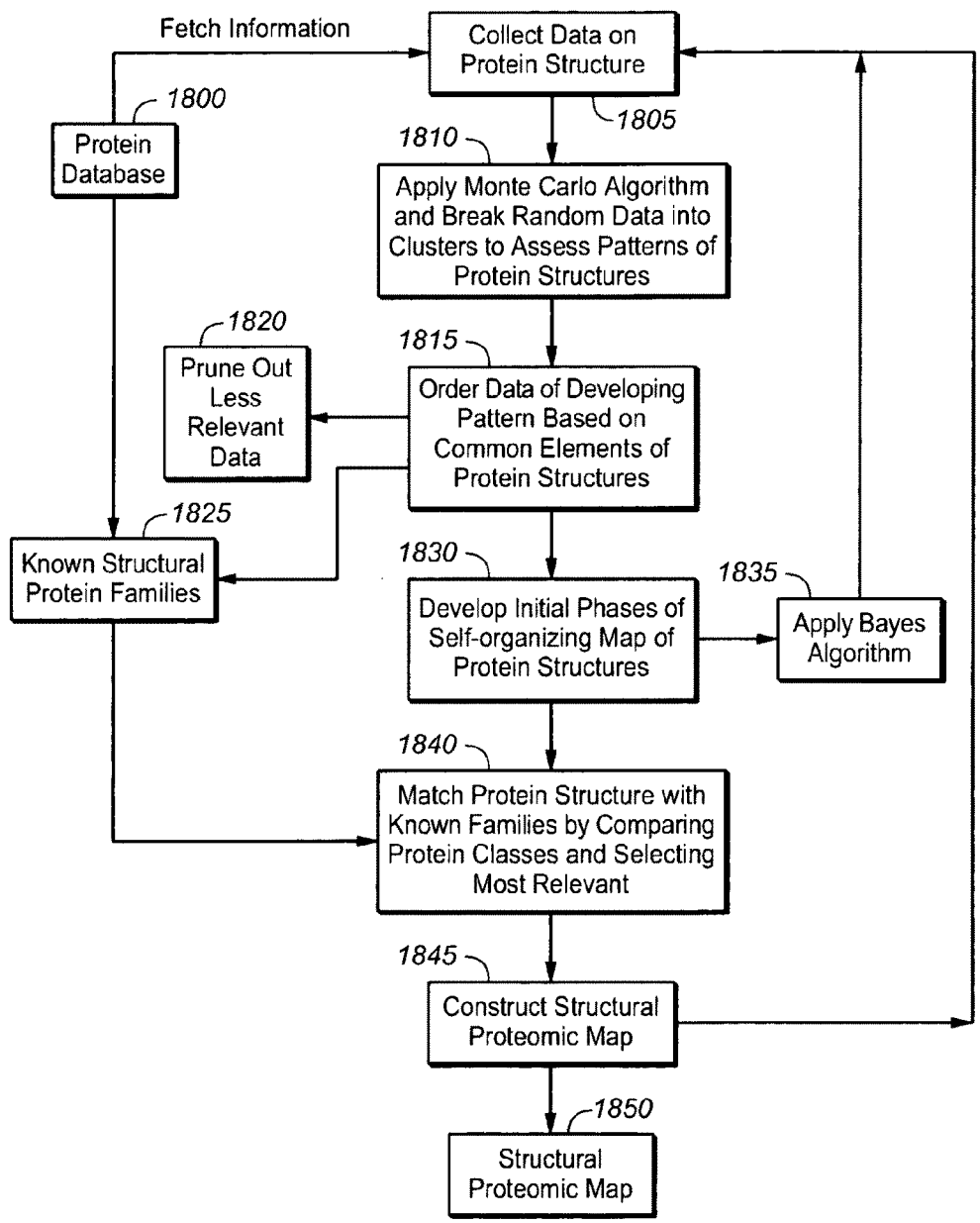
FIG._18

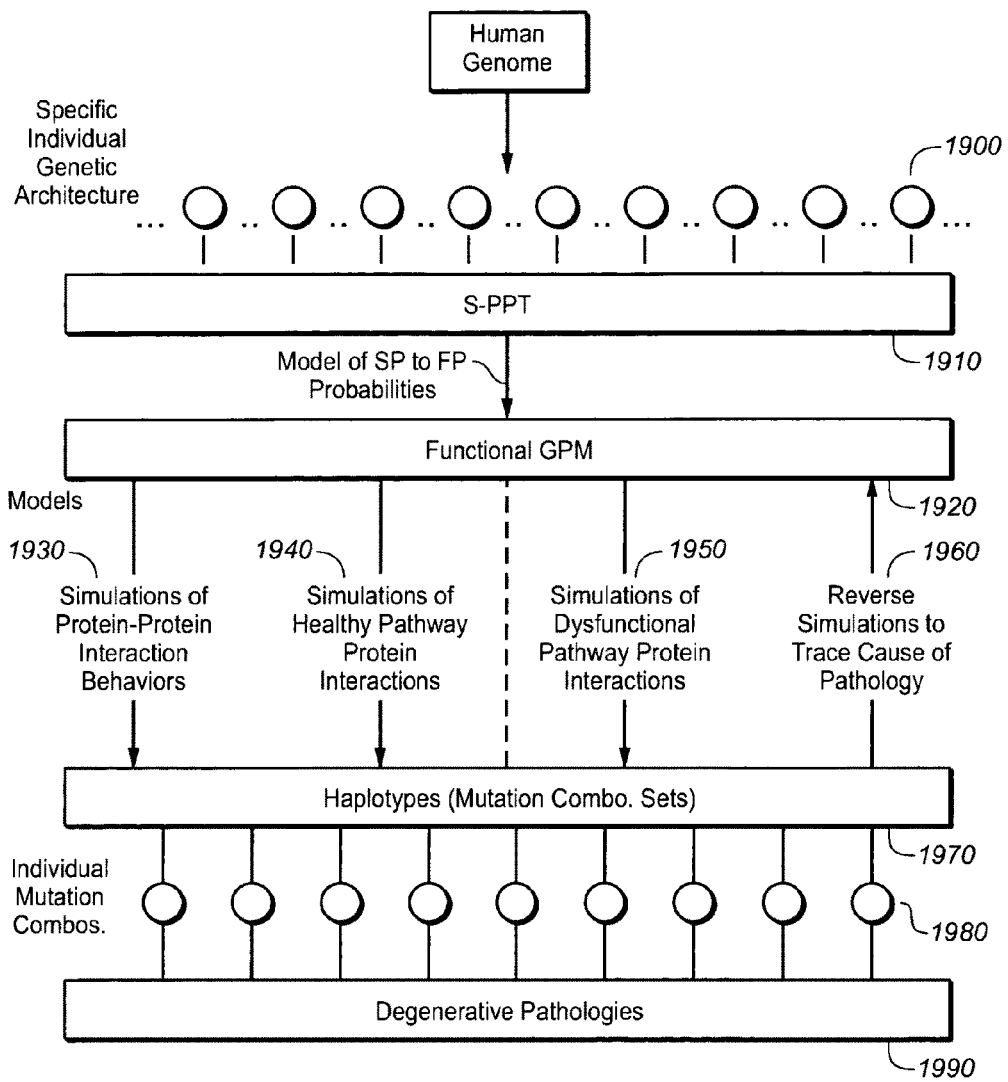
FIG._19

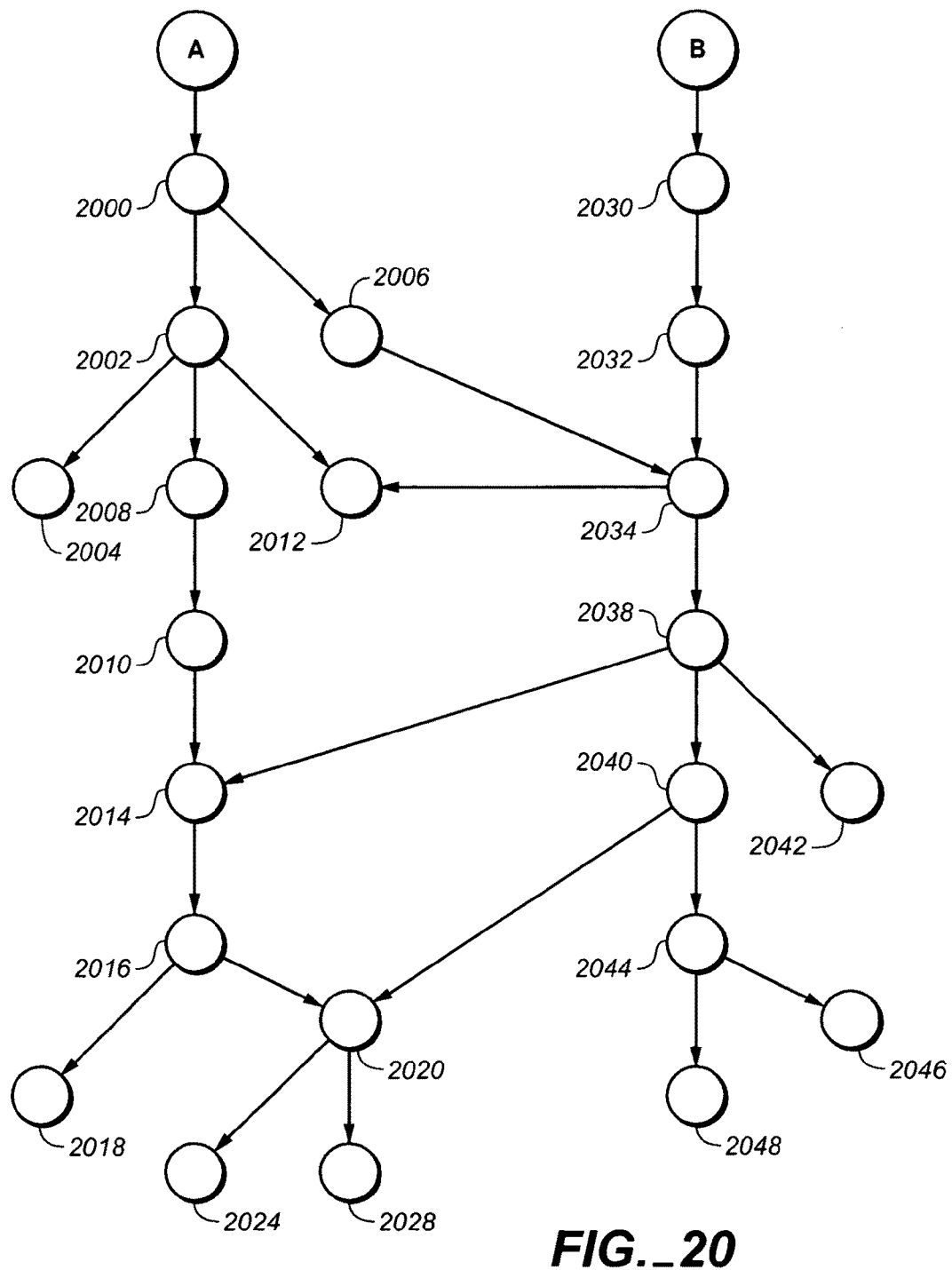
FIG._20

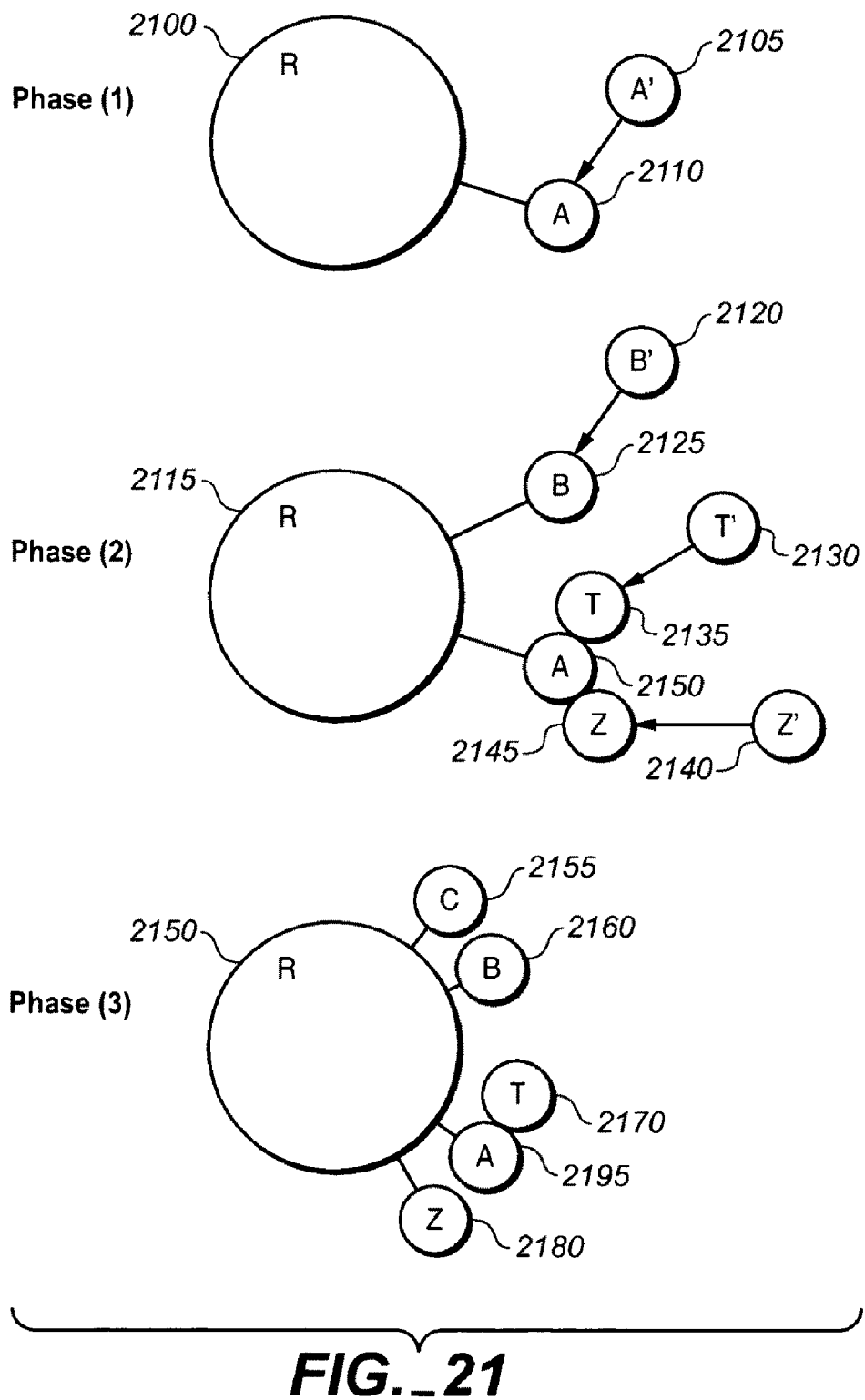
FIG._21

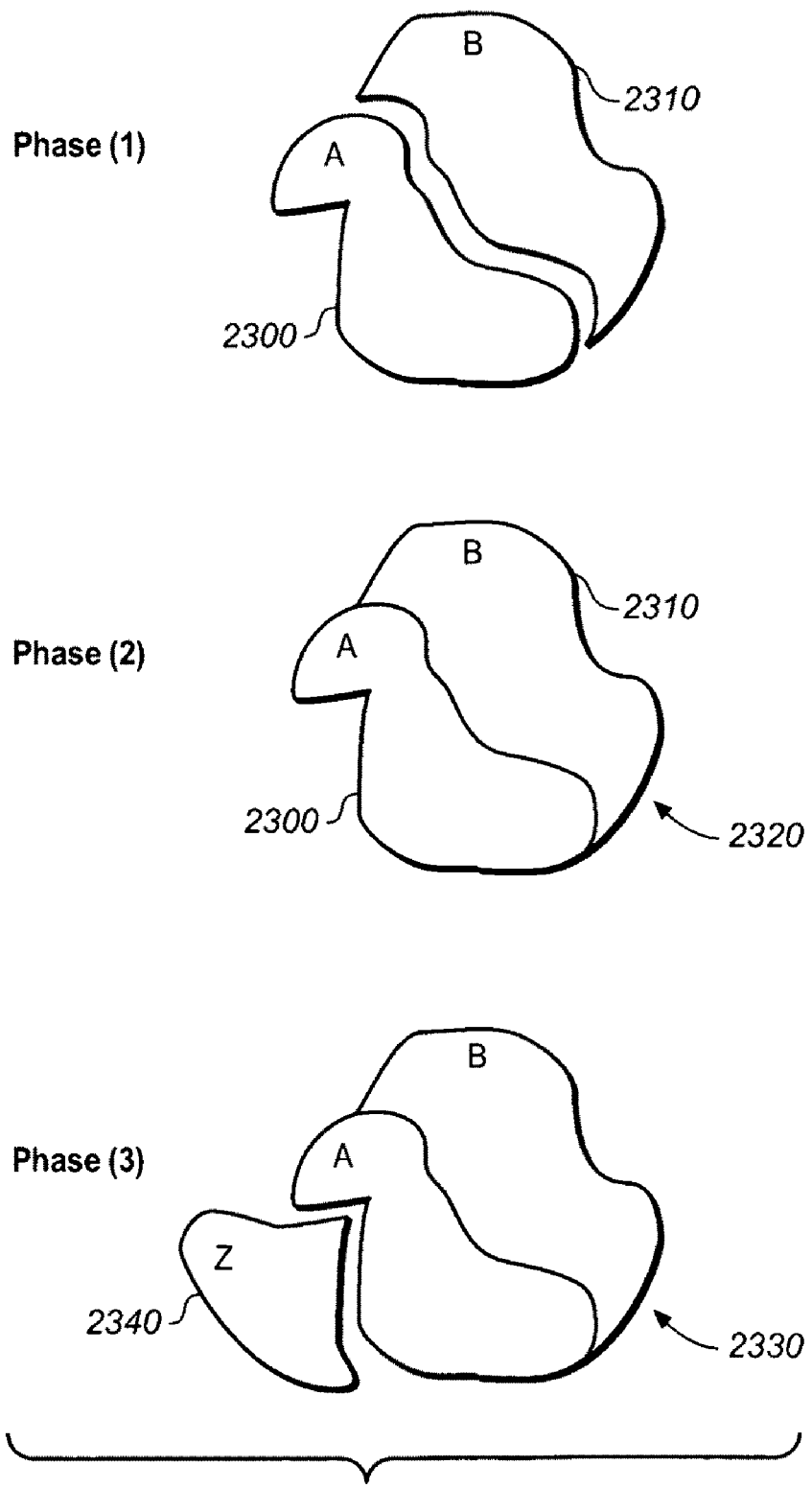
FIG._23

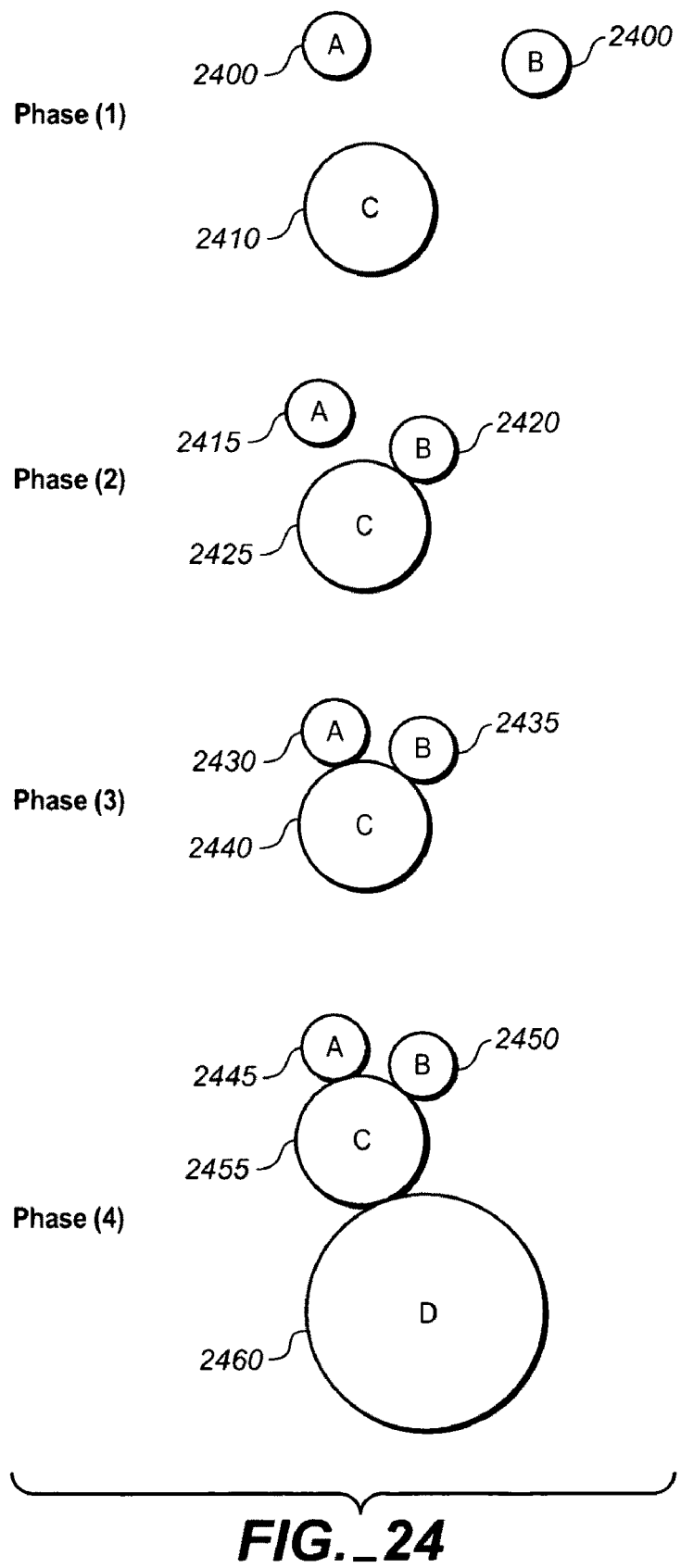
FIG._24

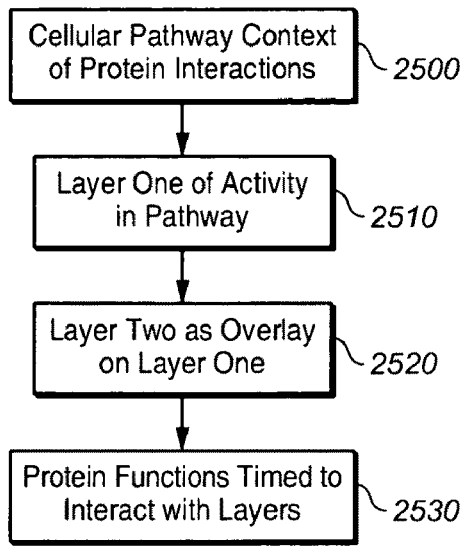
FIG._25
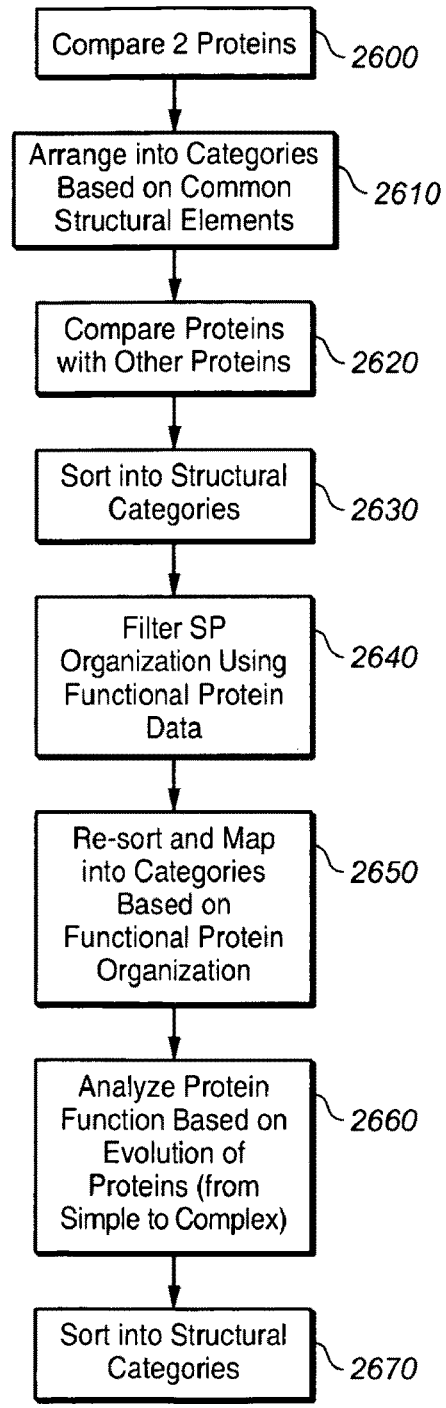
FIG._26

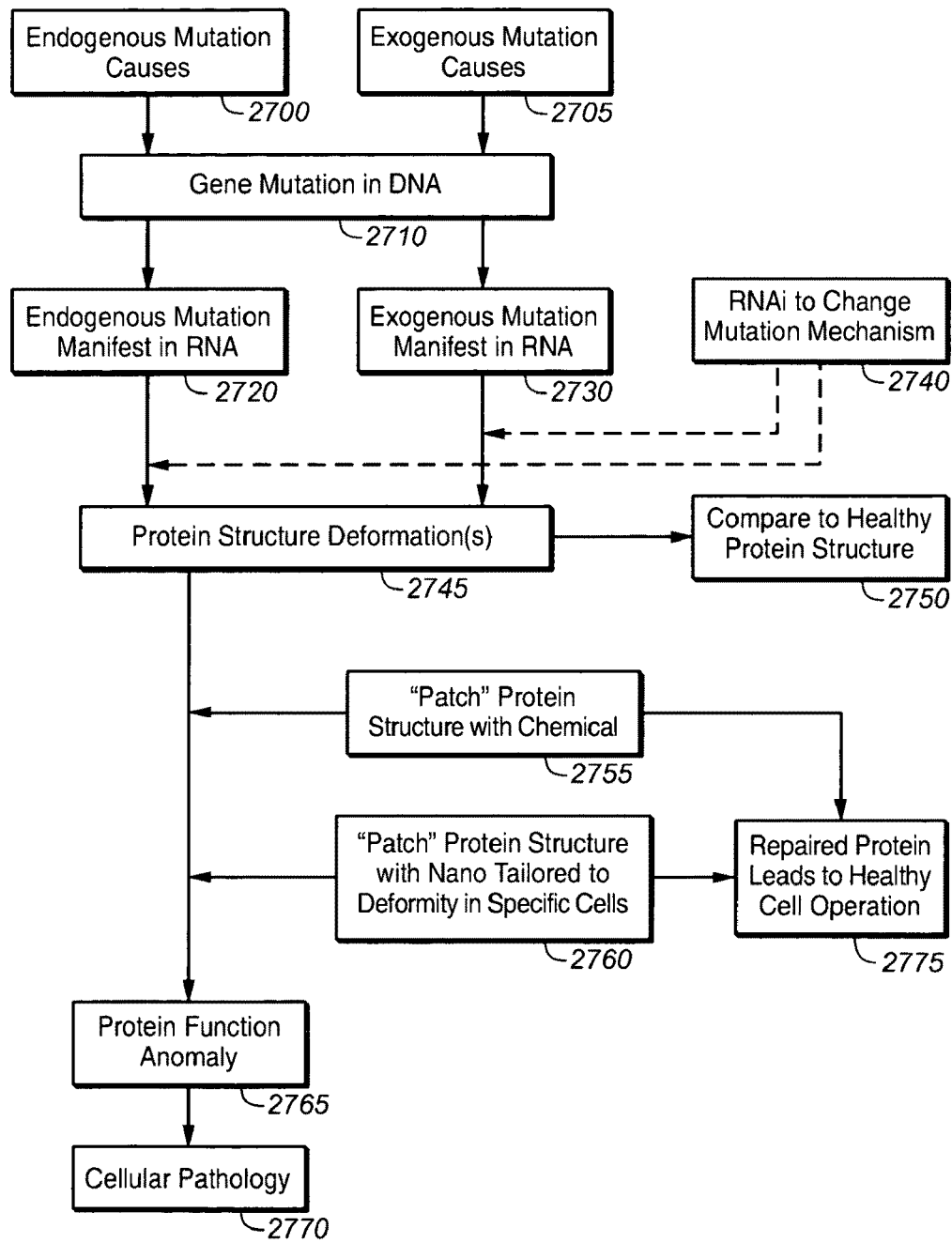
FIG._27

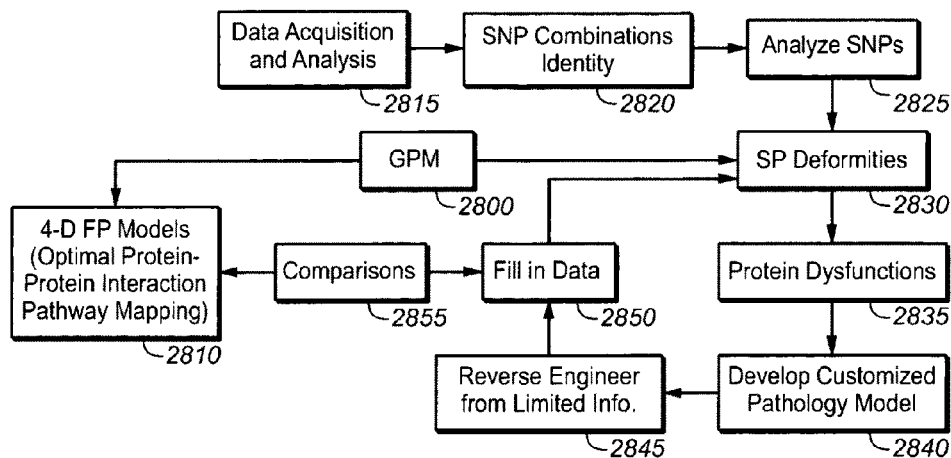
FIG._28
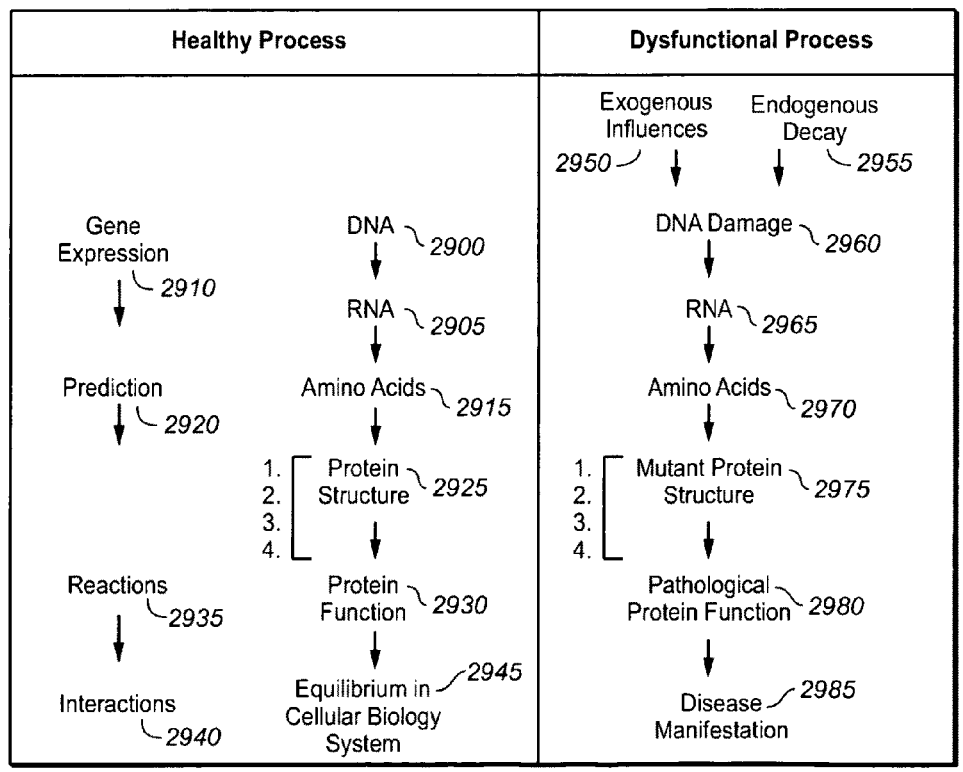
FIG._29

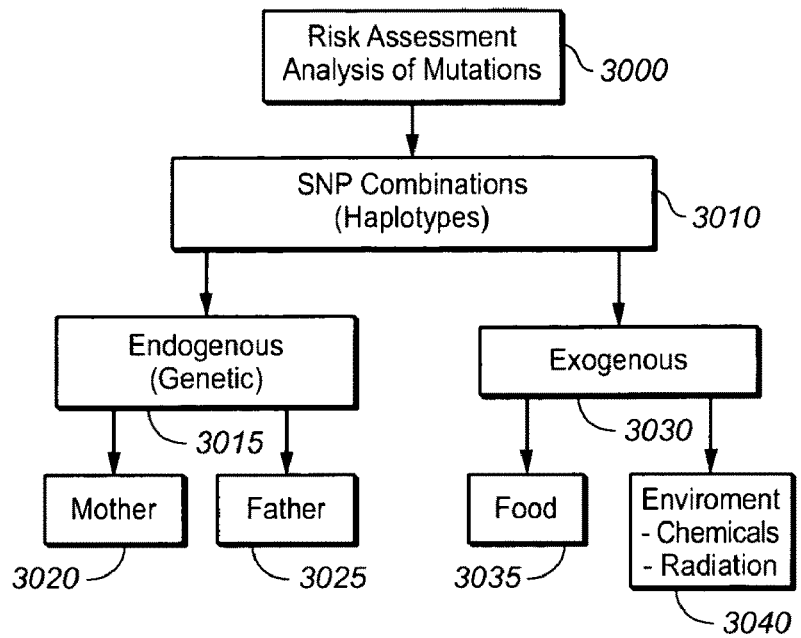
FIG._30
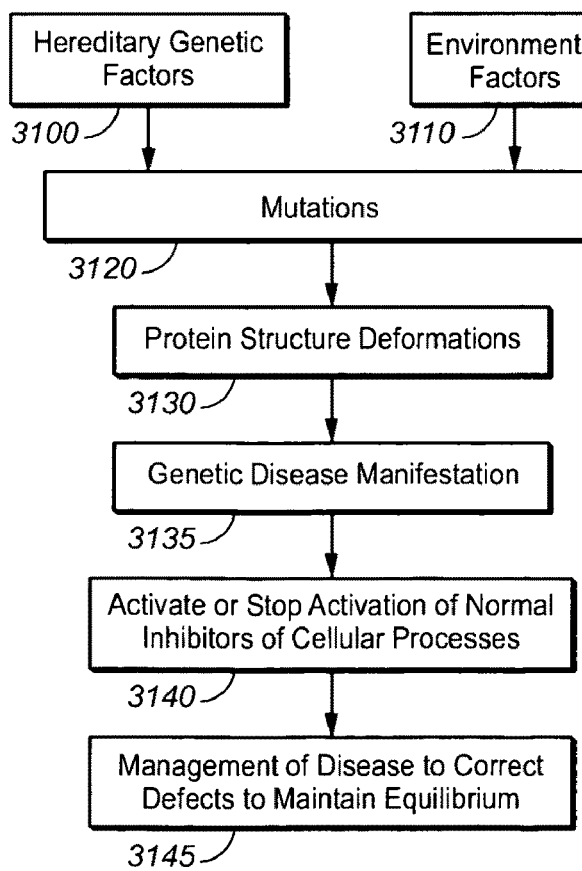
FIG._31

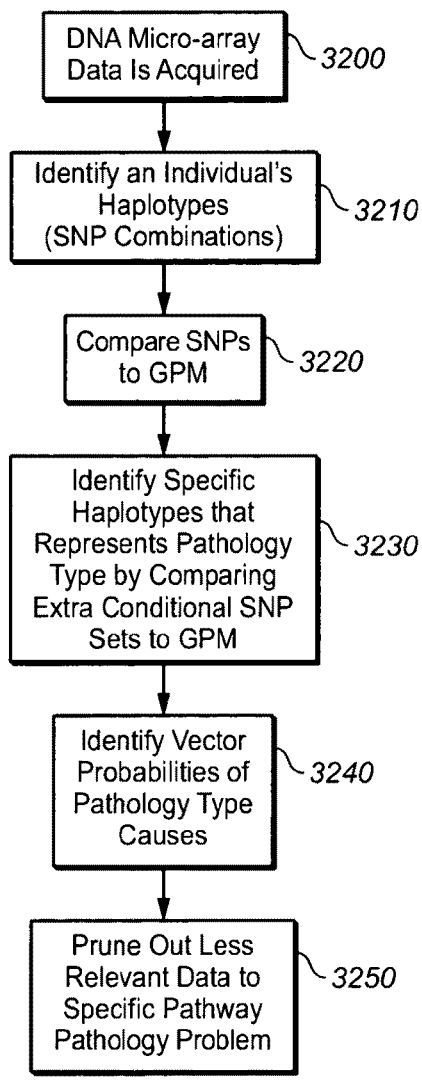
FIG._32
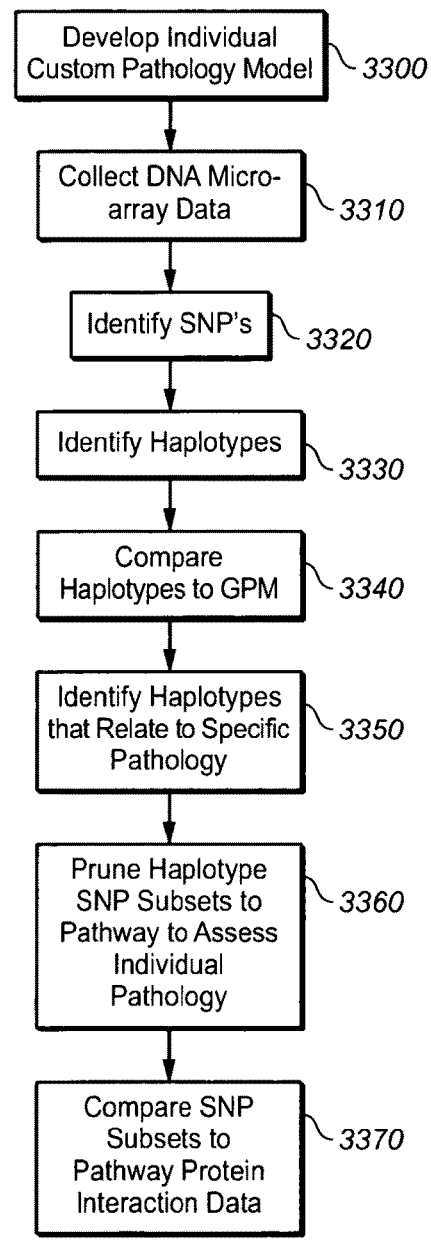
FIG._33

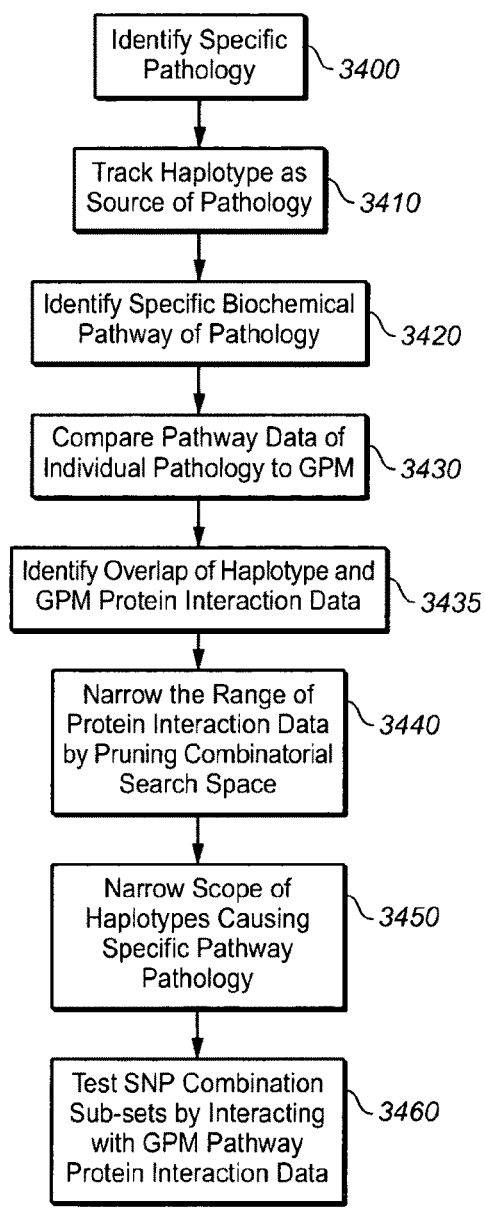
FIG._34
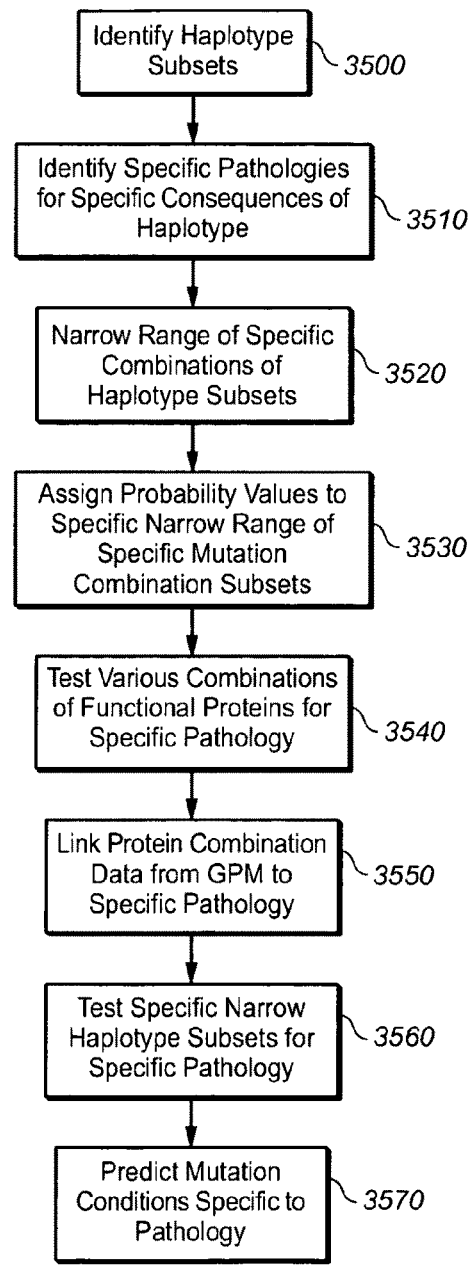
FIG._35

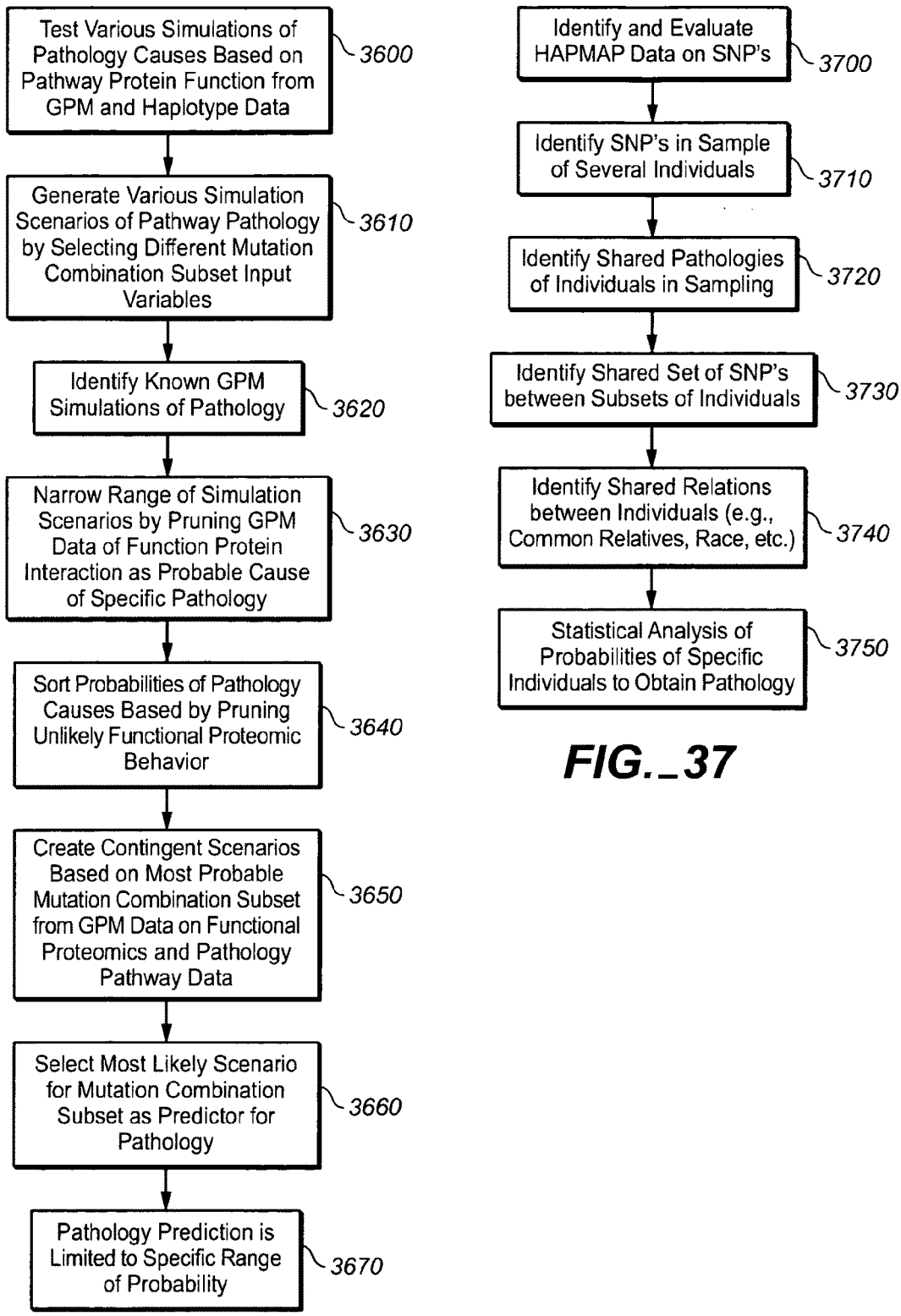

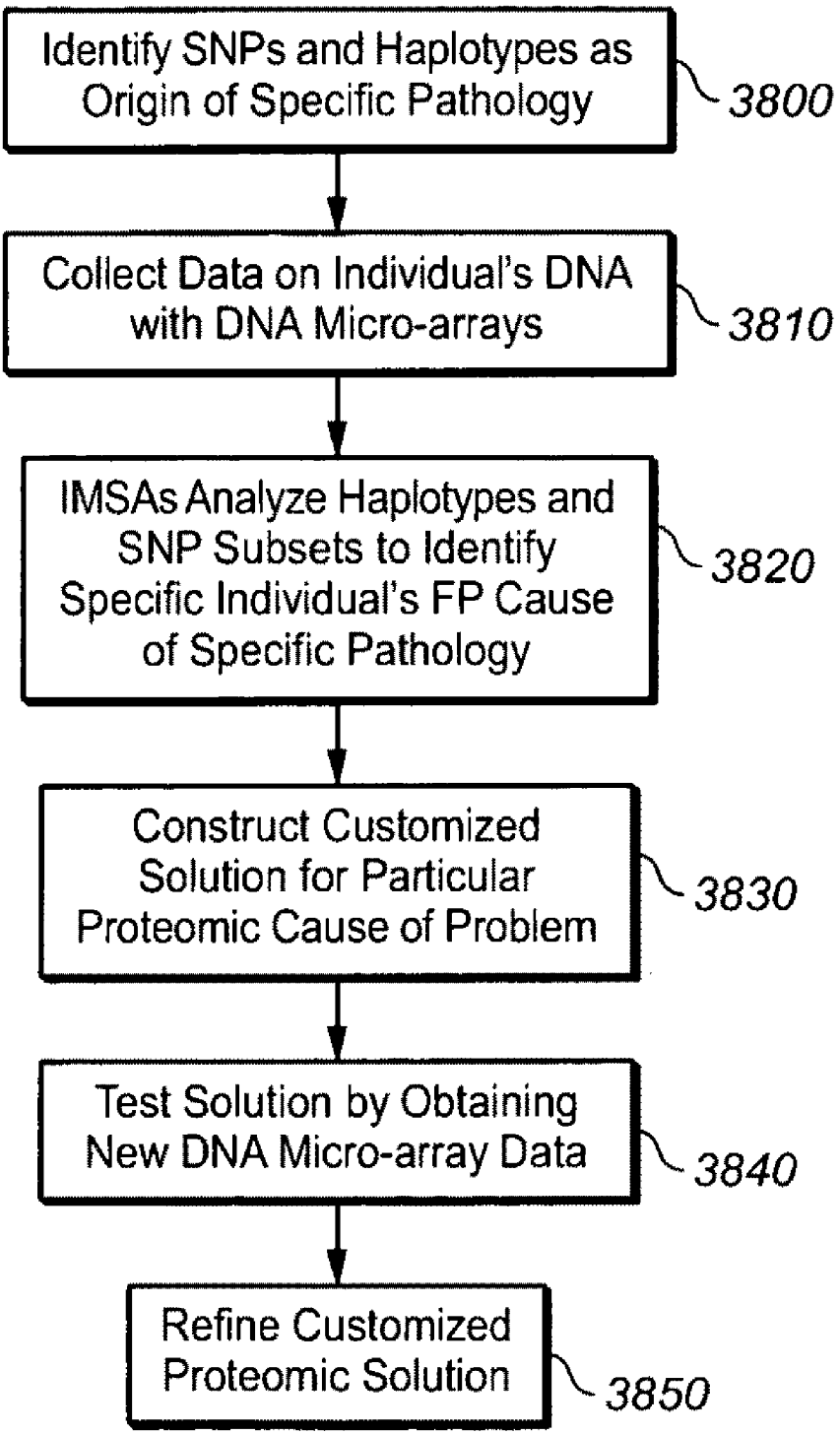
FIG._38

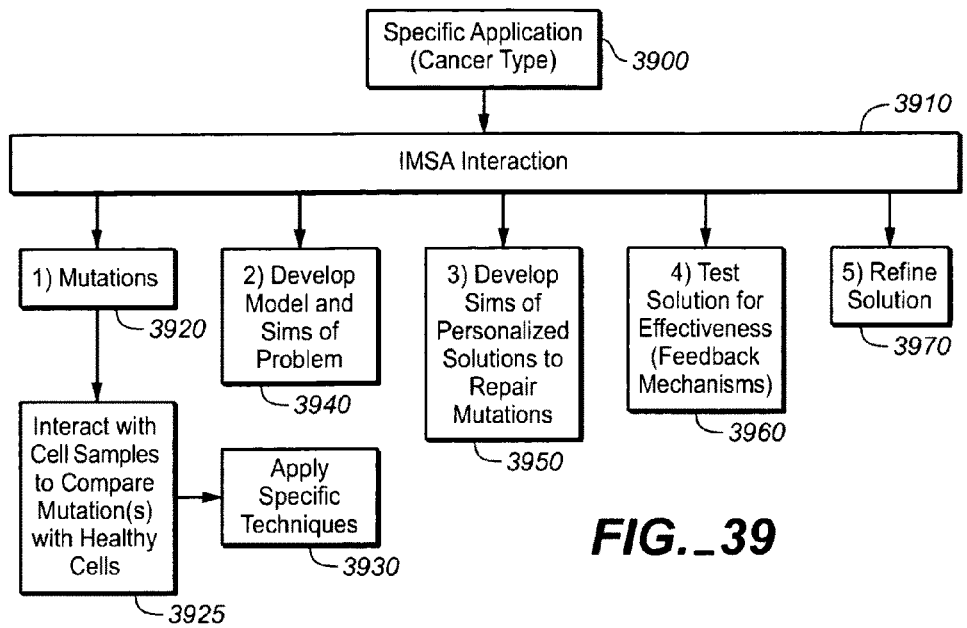
FIG._39
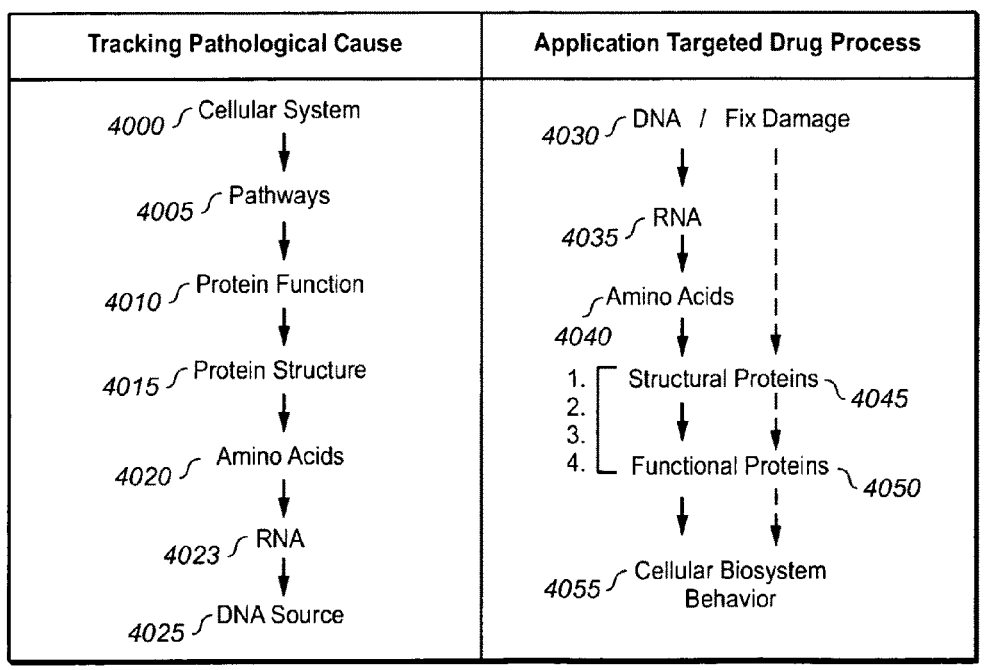
FIG._40

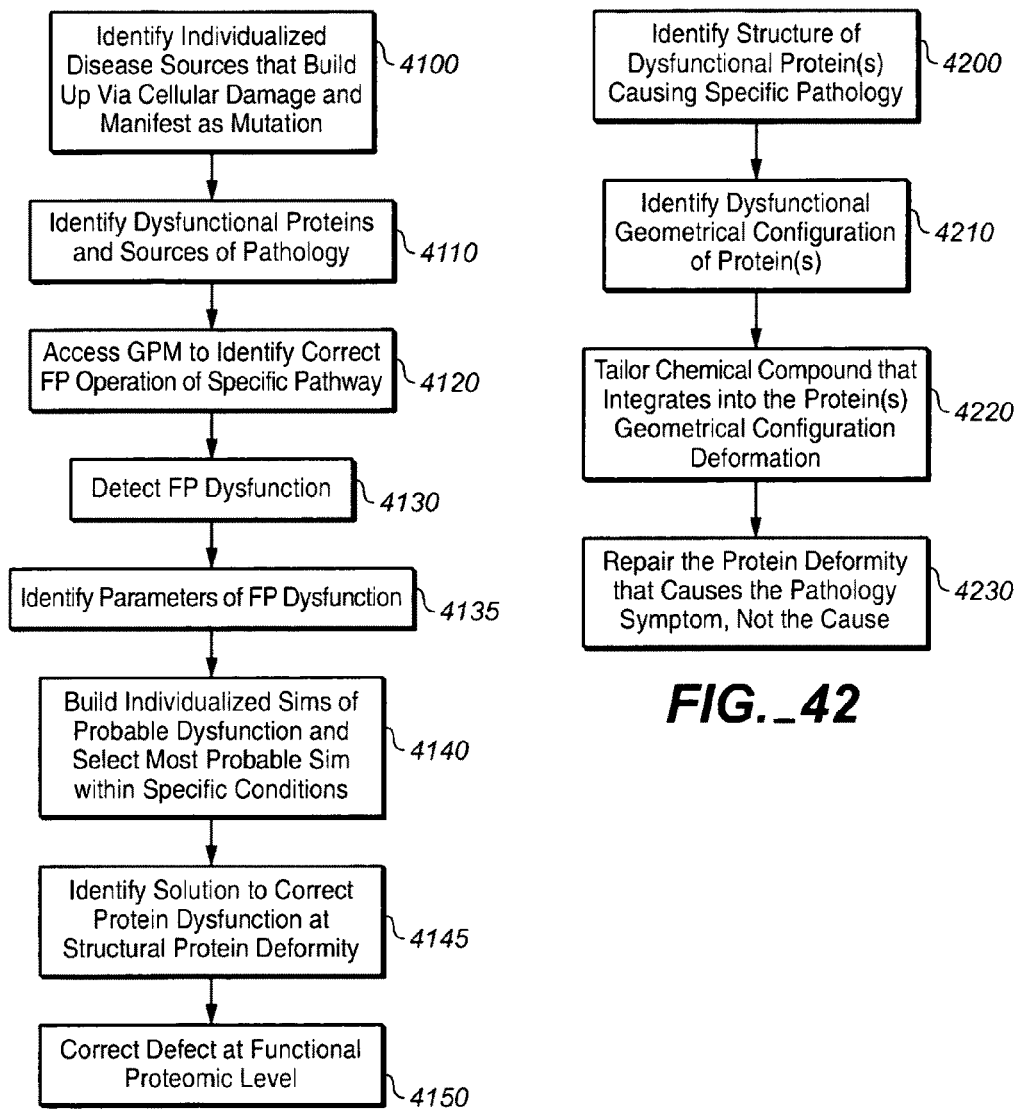
FIG._41
FIG._42

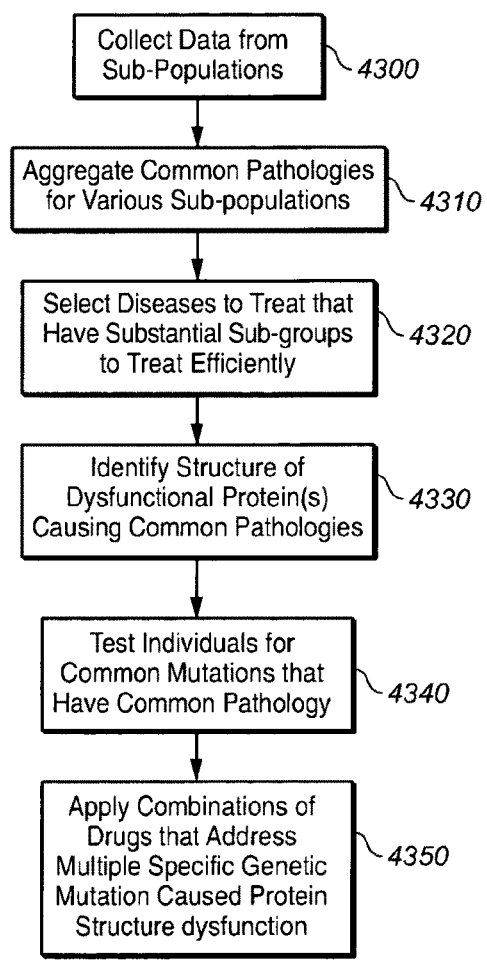

```
                    ┌─────────────────────┐
                    │  Collect Data from  │
                    │   Sub-Populations   │──4300
                    └──────────┬──────────┘
                               ▼
                ┌─────────────────────────────┐
                │ Aggregate Common Pathologies│
                │ for Various Sub-populations │──4310
                └──────────────┬──────────────┘
                               ▼
                ┌─────────────────────────────┐
                │ Select Diseases to Treat that│
                │ Have Substantial Sub-groups │──4320
                │      to Treat Efficiently   │
                └──────────────┬──────────────┘
                               ▼
                ┌─────────────────────────────┐
                │    Identify Structure of    │
                │   Dysfunctional Protein(s)  │──4330
                │ Causing Common Pathologies  │
                └──────────────┬──────────────┘
                               ▼
                ┌─────────────────────────────┐
                │    Test Individuals for     │
                │   Common Mutations that     │──4340
                │   Have Common Pathology     │
                └──────────────┬──────────────┘
                               ▼
                ┌─────────────────────────────┐
                │    Apply Combinations of    │
                │      Drugs that Address     │
                │  Multiple Specific Genetic  │──4350
                │  Mutation Caused Protein    │
                │    Structure dysfunction    │
                └─────────────────────────────┘
```

FIG._43

1. Universal Molecular Paste to Patch Parts of Dysfunctional Protein Structure
2. Individually Tailored Chemical Compound to Integrate into Protein Geometrical Configuration Dysfunction
3. Individually Tailored Nano-structure to Integrate into Protein Geometrical Configuration Dysfunction
4. Generate Healthy Protein to Substitute for Dysfunctional Protein
5. Apply RNA-i Techniques (Applied with Adinovirus) to Block Gene that Causes Secondary Dysfunctional Protein
6. Generate Synthetic Protein to Replace Dysfunctional Protein
7. Turn On Mechanisms to Attack
8. Fortify Immune System to Resist
9. Antibodies to Carry the Above Remedies
10. Develop and Apply Customized Vaccines
11. Combinations of These Approaches Tailored to Each Individual's Pathologies

FIG._44

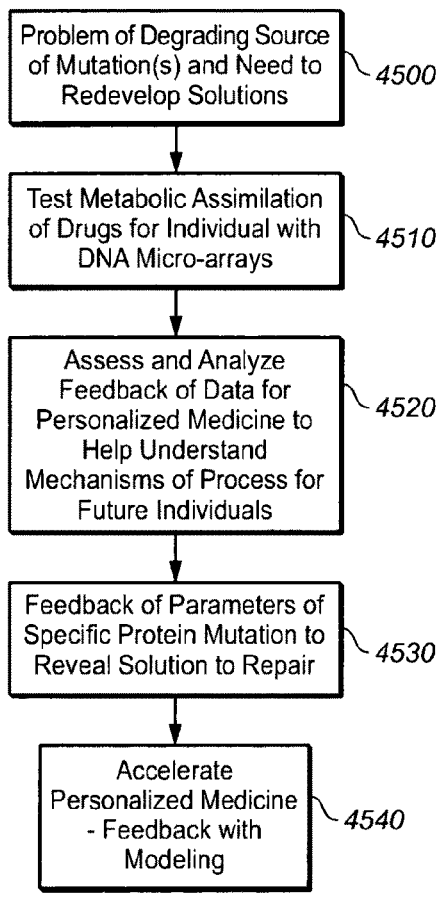
FIG._45
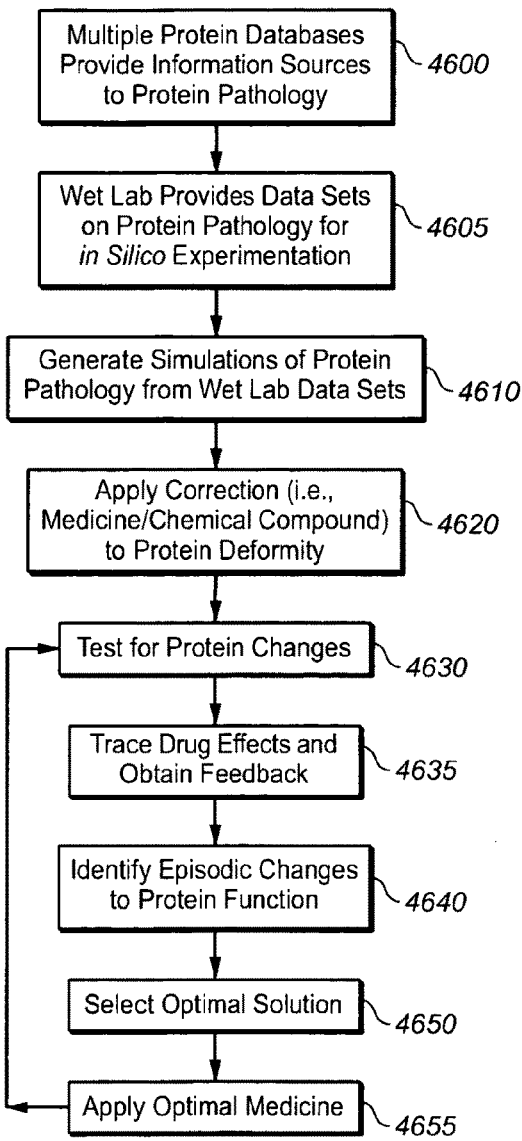
FIG._46

| | Cancer(s) | Neuro-Degenerative Diseases | Immuno-Degenerative Diseases | Aging | Optimum Health |
|---|---|---|---|---|---|
| Problem | Cellular Mechanism Dysfunction (to Stimulate Cell Division) | Cellular Mechanism Dysfunction or Decay | Regulatory Master System (in State of Equilibrium) as Protector Against Dysfunction, Decay and Exogenous Factors | Cellular Mechanism Deterioration (Erosion) | Compare with GPM to Seek Optimal Equilibrium |
| Proteomics | Genetic Mutations Cause Unique Combinations | Genetic Mutations Intracellular Degradation | Intracellular Degradation Extracellular Degradation | Genetic Mutations Accumulation Intracellular Degradation | |
| Source | Endogenous Sources | Endogenous Sources | Endogenous Sources and Exogenous Sources | Endogenous Sources | |
| Solution | Retard Growth of Tumors | Delay Onset or Stimulate Growth of Cells | Fortify Immune System and Delay Accumulation of Degradation Attack | Delay Degradation or Stimulate Healthy Function | |
| Bio-Mechanism | Block, Inhibit or Disable Mechanisms | Block, Inhibit or Disable Mechanisms | Block or Fortify Mechanisms | Block Degradation or Fortify Mechanisms | |

FIG._47

| Cancer Type | Endogenous Mutations | Exogenous Mutations | Drug |
|---|---|---|---|
| Lung | EGFR<br>Tyrasine Kinase (TK) →<br>Seek TK Inhibitor | Smoking<br>(Chemical) | Iressa<br>(Angiogenic) |
| Breast | HER-2 →<br>Cell Surface Receptor Protein | | Herceptin<br>(Antibody Based) |
| Colo-Rectal | B-RAF (20%) | Radiation<br>Chemical | Erbitux |
| Kidney | EGFR →<br>Tyrasine Kinase (TK) →<br>Seek TK Inhibitor | Chemical | Avastin<br>(Angiogenic)<br>Tarceva<br>(TK Inhibitor) |
| Leukemia | Chromosomes 9&22<br>Hybrid BCR - ABL Genes- ALM at Chromosomal Junction between BCR - ABL Genes<br>Tyrasine Kinase (TK) →<br>Seek TK Inhibitor | Radiation/Chemical | Gleevec<br>(Promitotic) |
| Skin (Melonoma) | B-RAF (80%) | Radiation | |

*FIG._48*

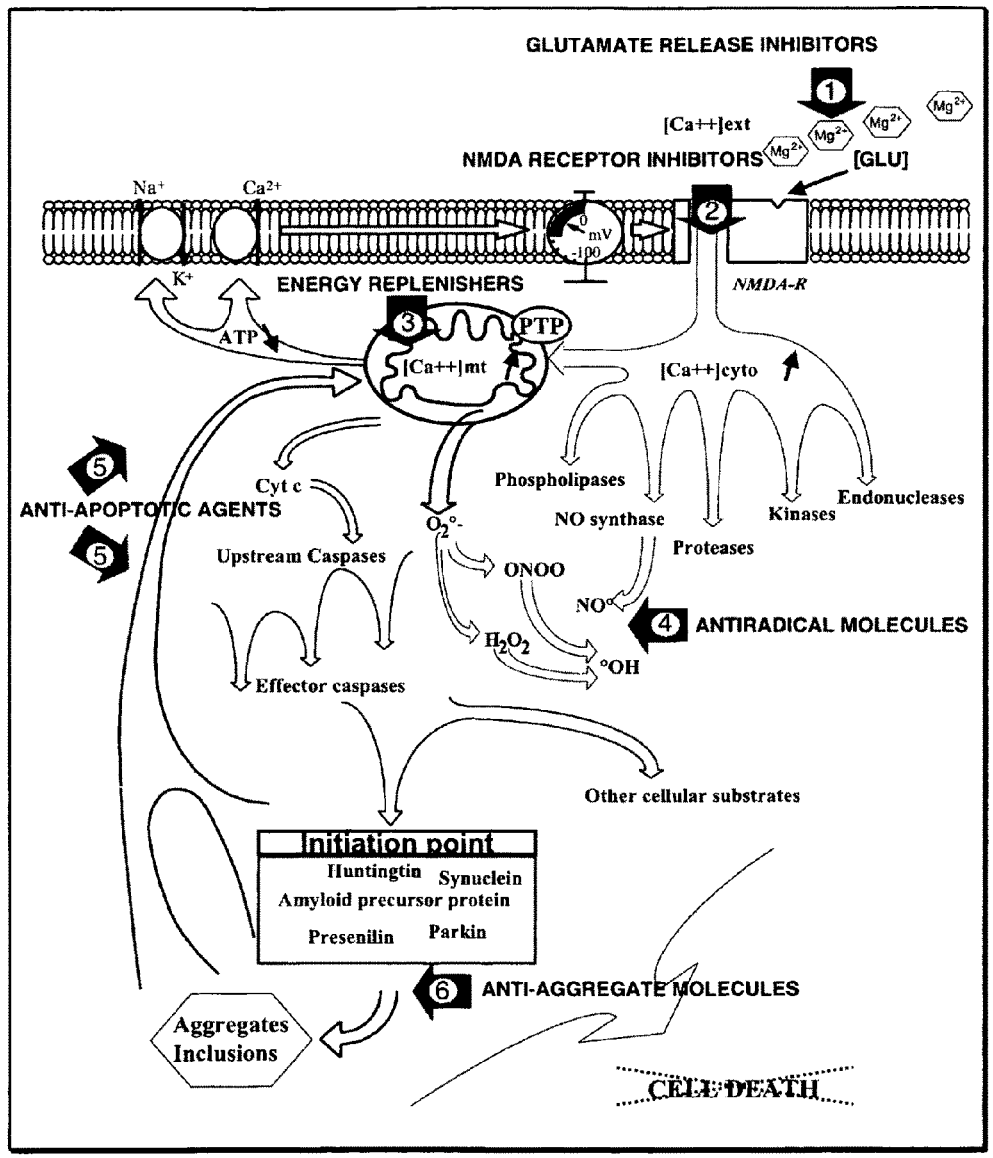
Source: Pharmacogenomics, Licinio & Wang, '04
FIG._50

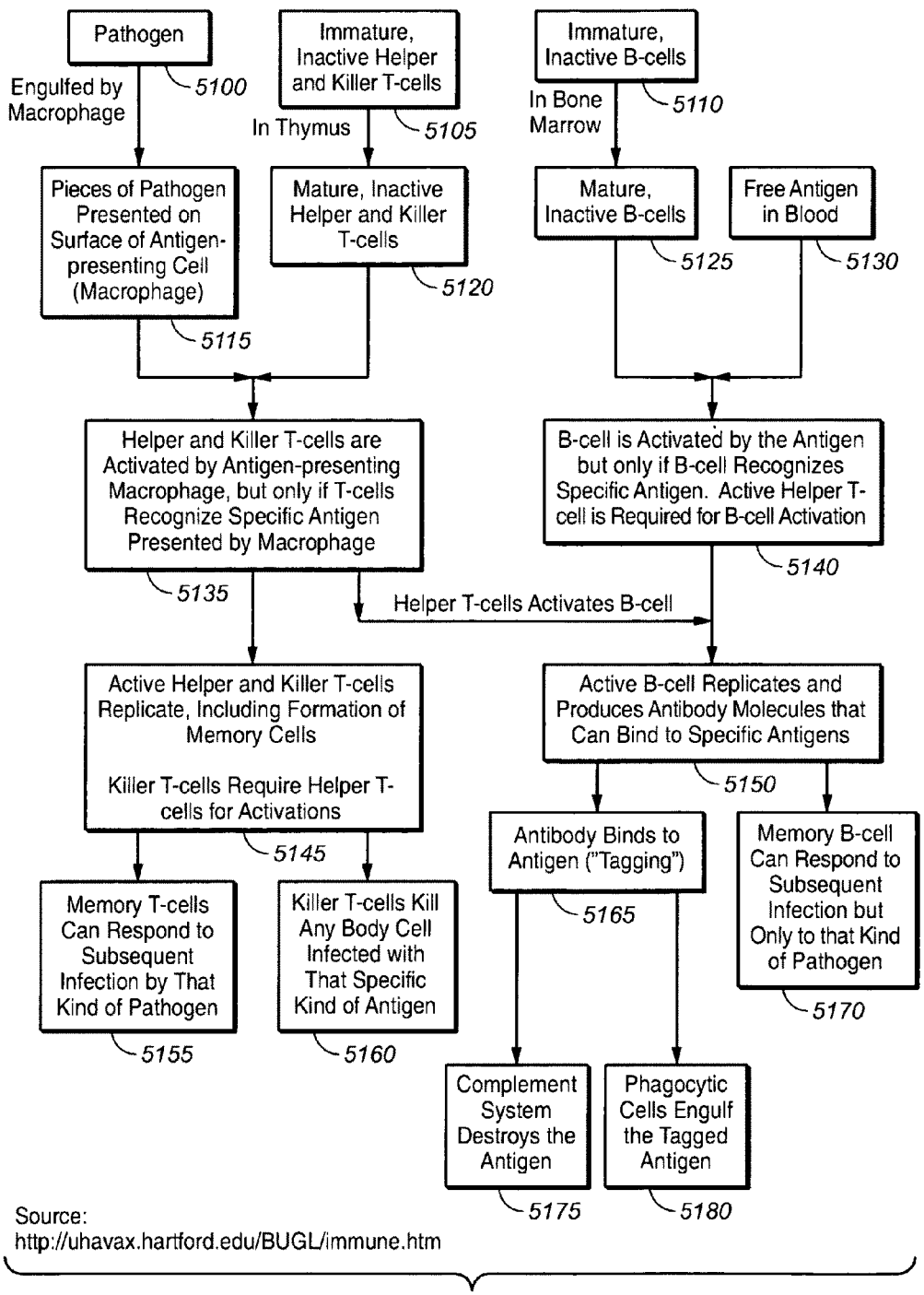
FIG._51

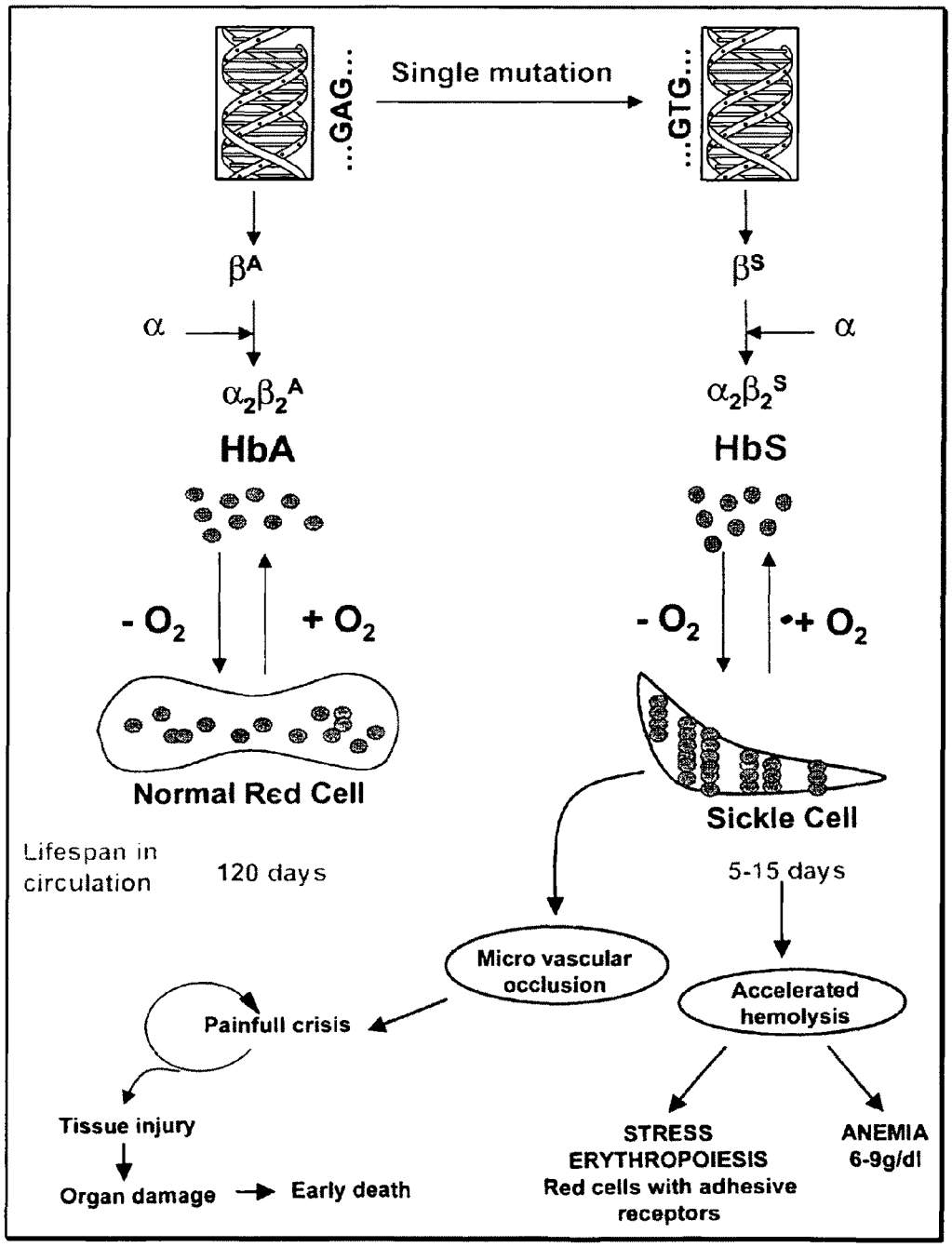
FIG._52

|  | Gerontoproteomics |
|---|---|
| Mitochondrial Membrane Integrity | Oxidation Causes Degeneration |
| Cellular Wall Decay | Oxidation Causes Degeneration |
| Telomere Decay | - Chromosome Tips Decayed by DNA Replication<br>- Cell Copy Degradation (Manifest as Aging) |
| Mitochondrial DNA Mutation Accumulation |  |

FIG._53

|  | Monte Carlo<br>Small Cluster<br>(Parallel Process) | Monte Carlo<br>Big Cluster<br>(Sequential Process) |
|---|---|---|
| Bayes I<br><br>Early Experiment<br>(Initiation Process) | - GPM Accumulation Picture<br><br>- Build Self-organizing Map | Individual Mutation Maps Initiated |
| Bayes II<br><br>Reorganization and Refinement of Model | Later Development GPM | Refining Stage Individual Mutation Maps |

FIG._54

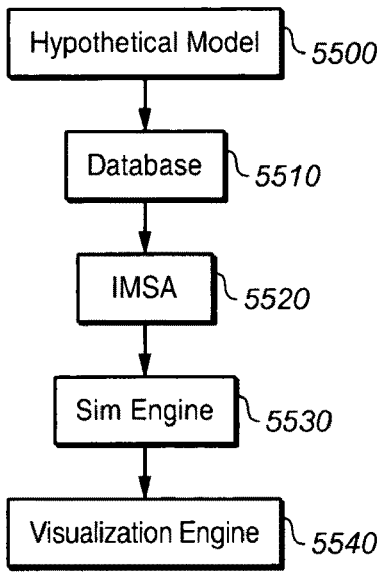
FIG._55
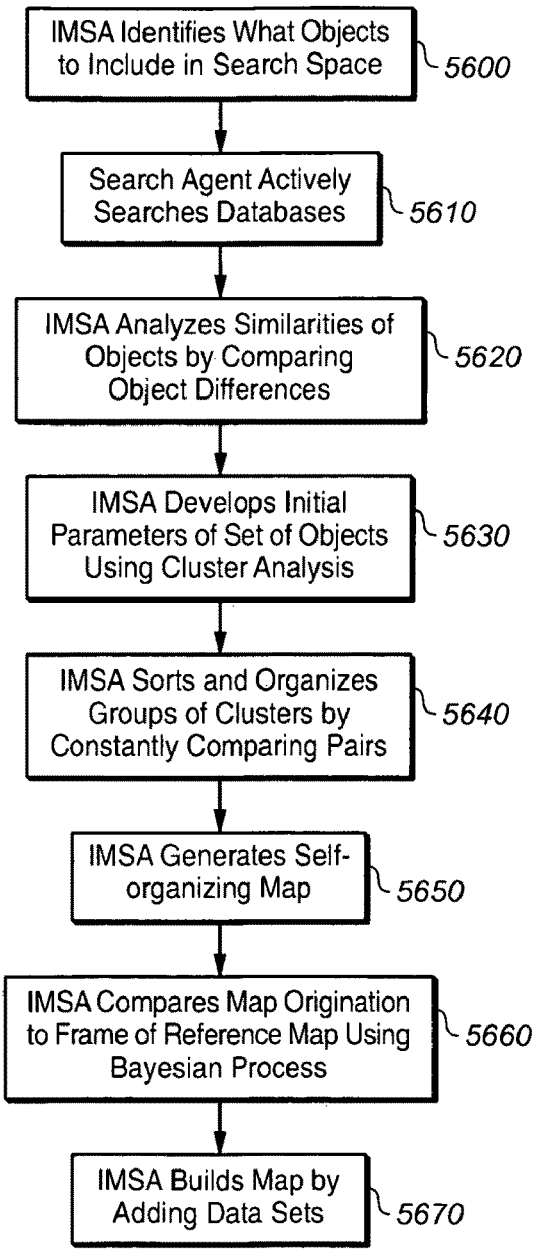
FIG._56

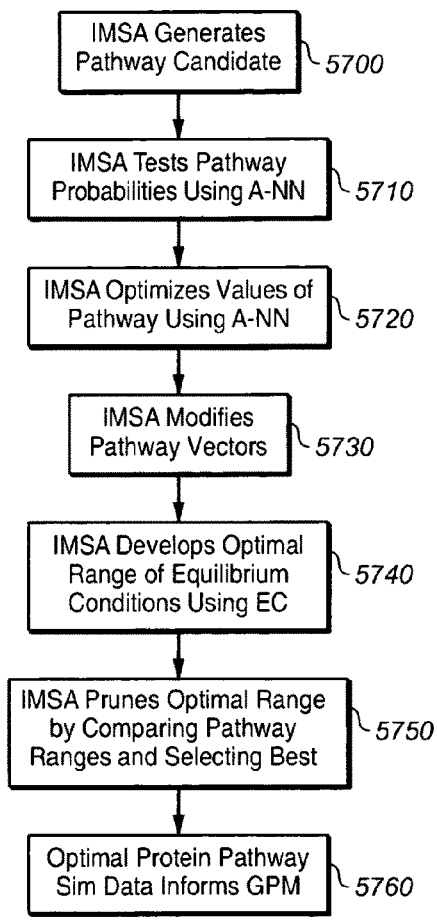
FIG._57
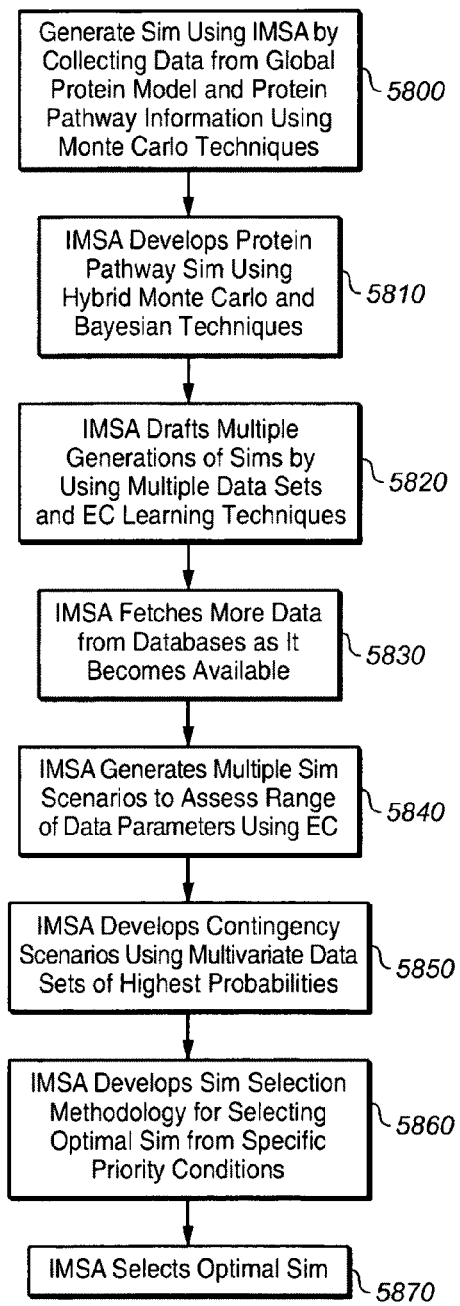
FIG._58

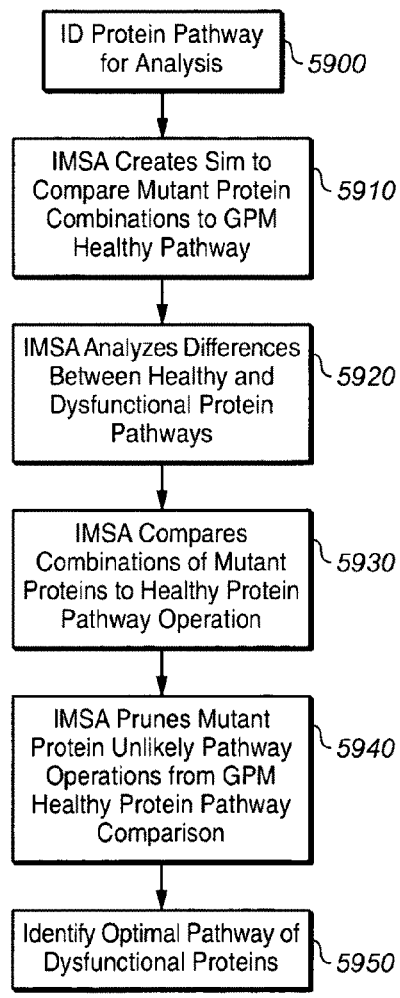
FIG._59
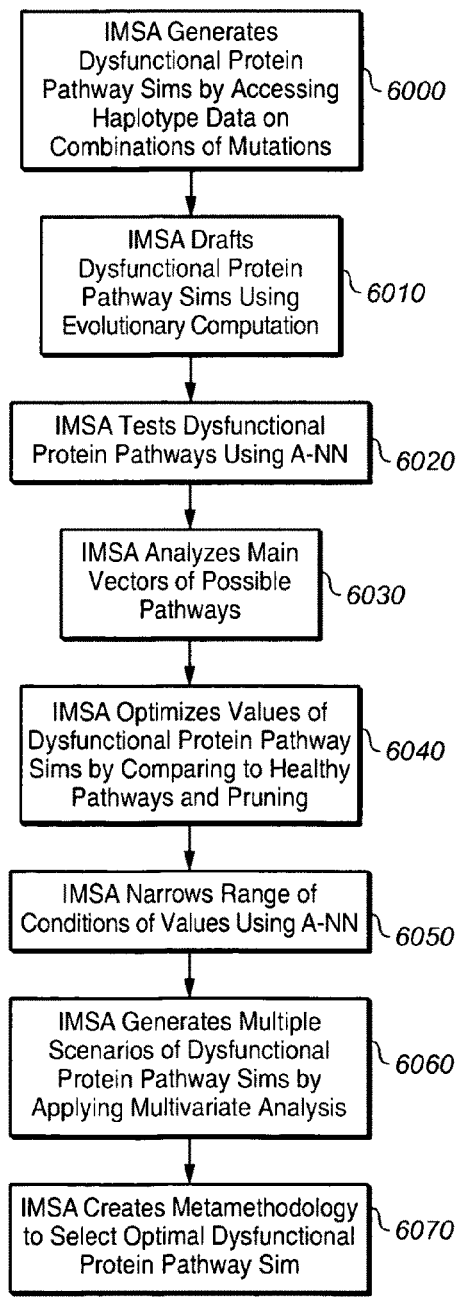
FIG._60

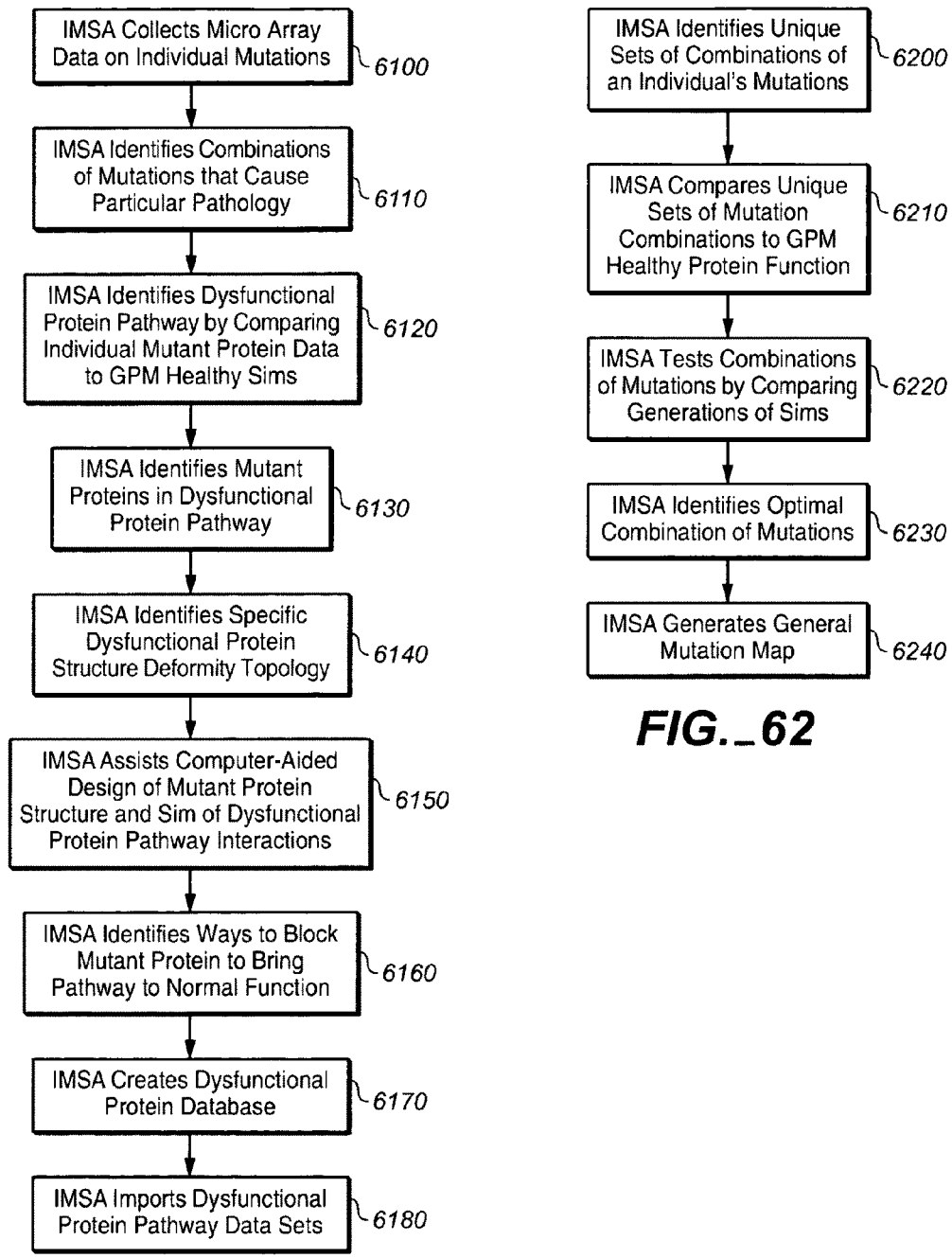
FIG._61
FIG._62

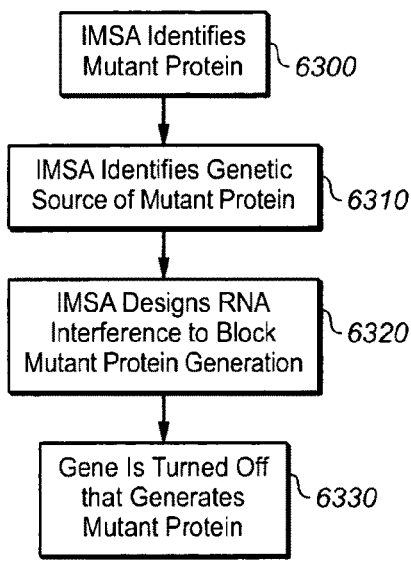
FIG._63
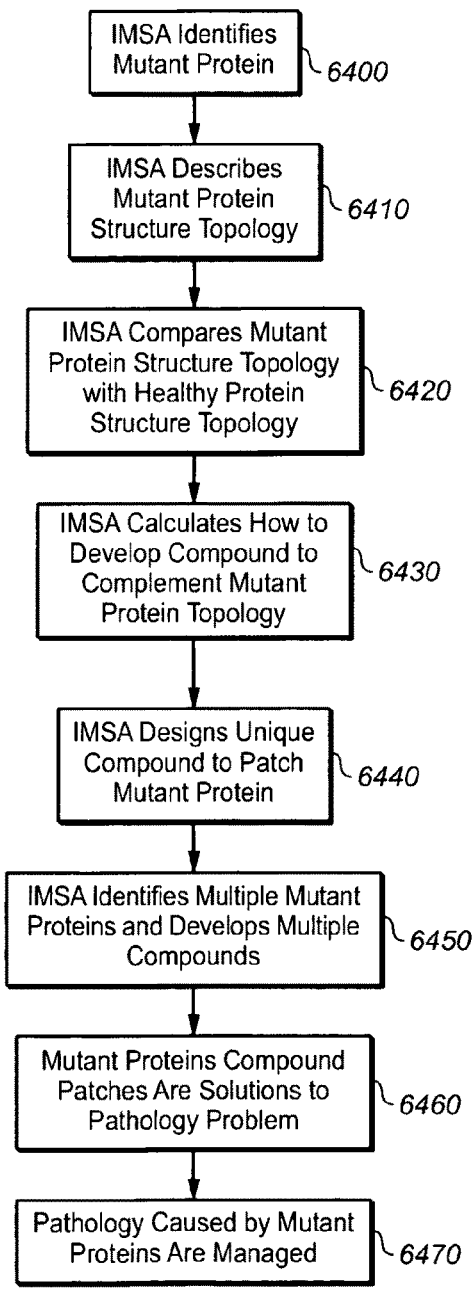
FIG._64

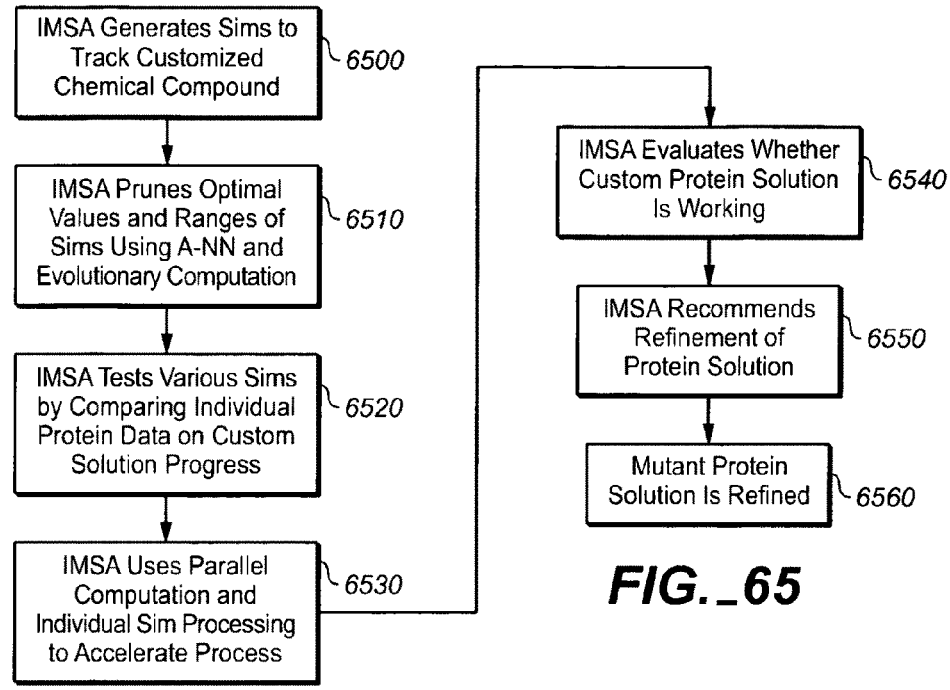

FIG._65

| GPM Healthy Functional Protein Operation Simulations | Dysfunctional Protein Pathway Simulations | Active and Interactive Pharmacoproteomics Process Simulations |
|---|---|---|
| • FP Interaction Sims<br>• FP Pathway Scenarios Based on Equilibrium Variables Using Sims<br>• Optimal Pathway Selection Process Using Sims<br>• Trace FP Sim to SP (and to Gene(s))<br>• Partial Information FP Sims based on Probabilities<br>• Sims Inform GPM about Analytical Relations | • Combinations of Mutations Sims<br>• Reverse Engineer Sims from Disease to Gene<br>• Sims of Scenarios Based on Variables of Disequilibrium of FP or on Dysfunctional Protein Operations<br>• Sims of Pathway Scenarios of Dysfunctional Protein Interactions<br>• Optimal Pathway Selection Process Sims<br>• Sims to Identify SP Profile of Mutant Protein from Dysfunctional Pathway Analyses | • Sims to Design Custom Solution to Mutant Protein Topology<br>• Sims to Test Solution Candidates Using Pathway Scenarios and Updated Feedback Data<br>• Sims to Refine Solutions Using Real Data from Solution-Candidate Feedback |

FIG._66

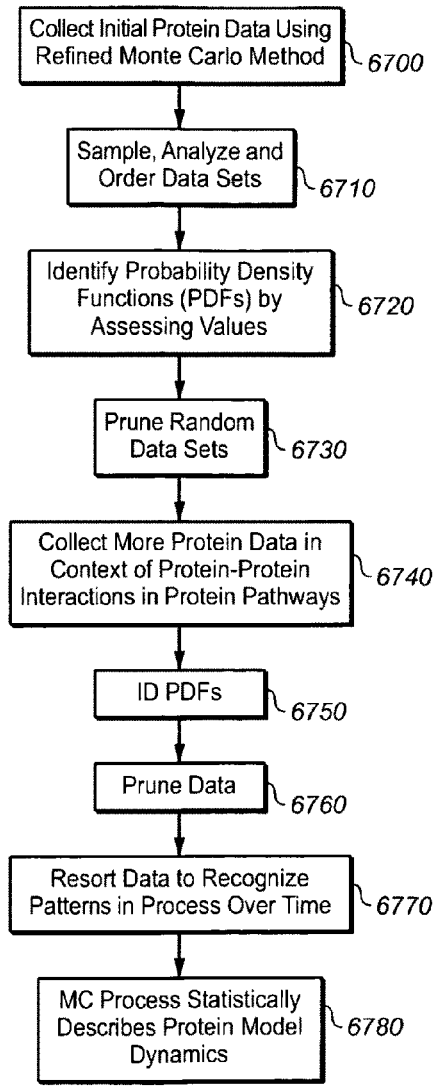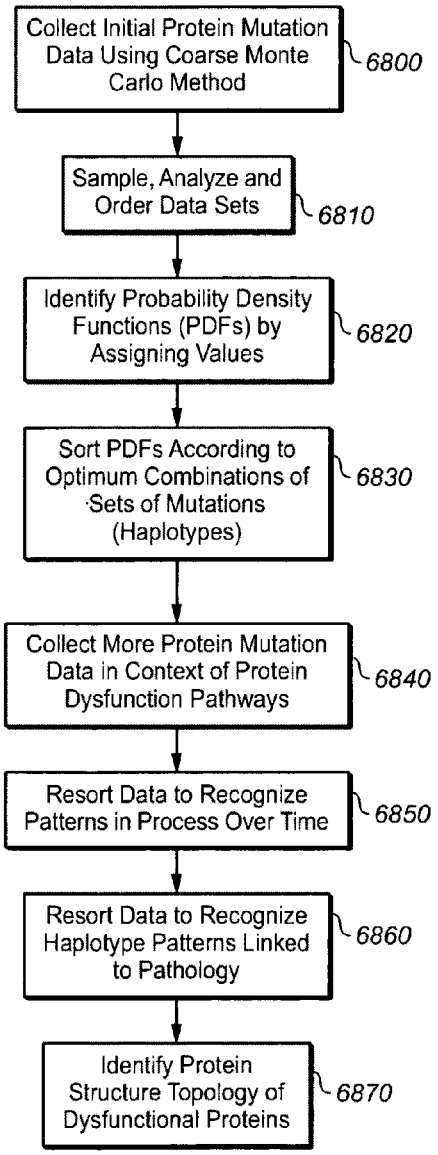
FIG._67
FIG._68

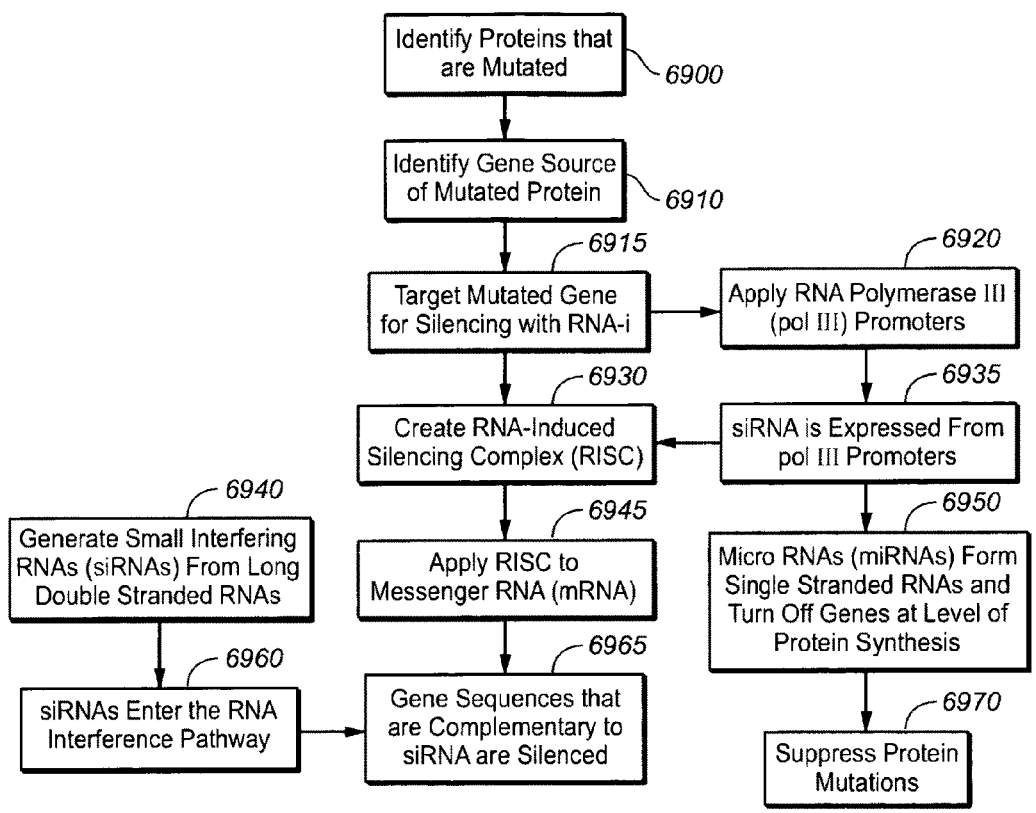
*FIG._69*

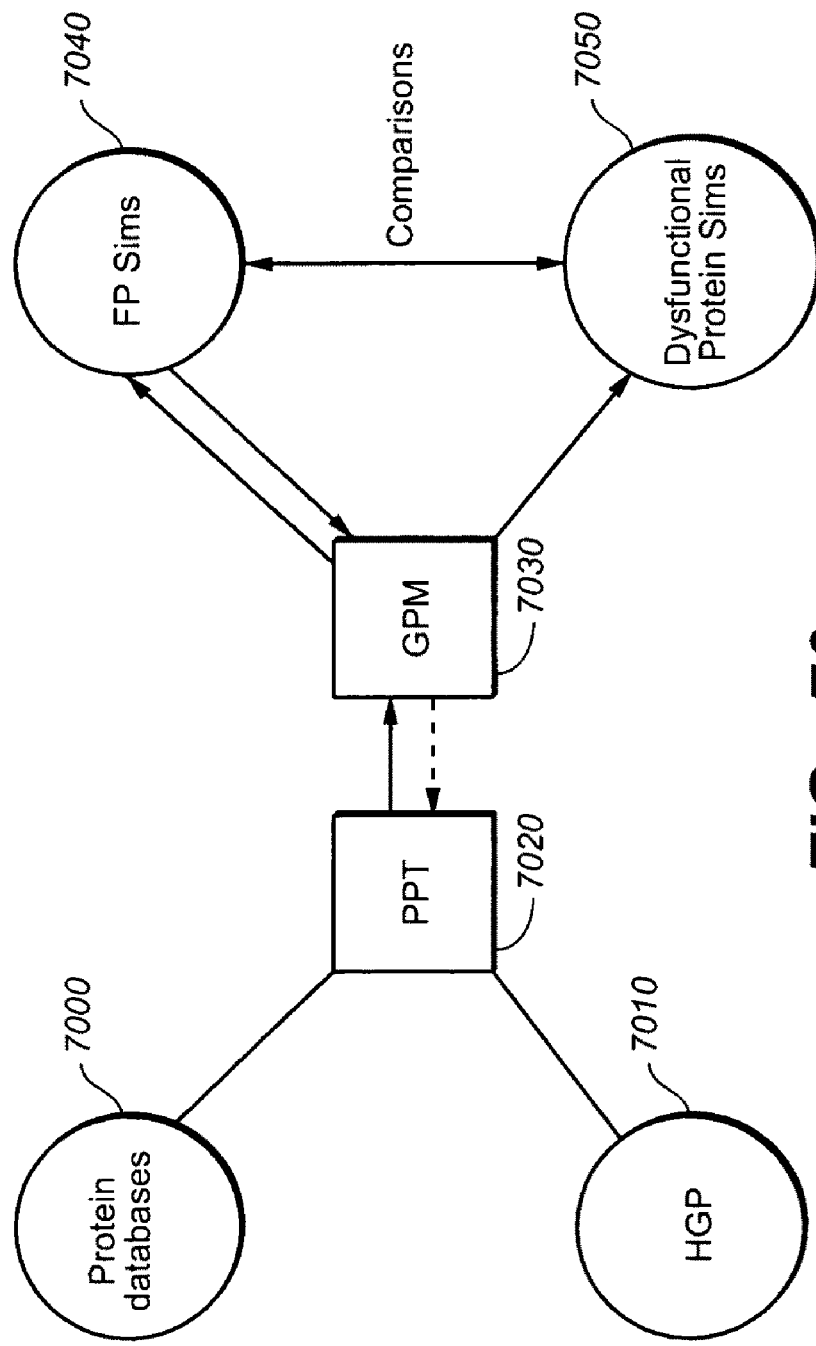
FIG._70

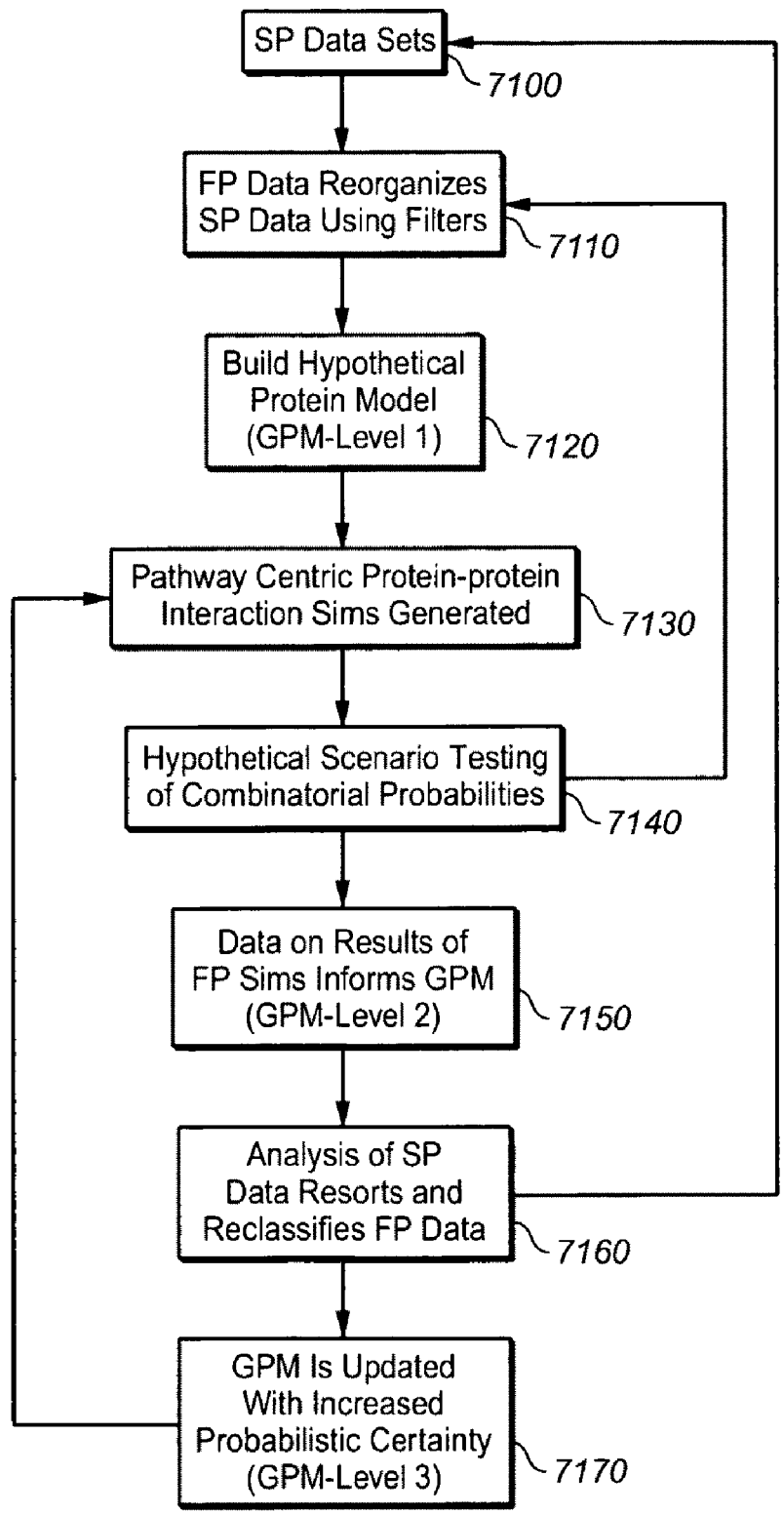
FIG._71

BIOINFORMATICS SYSTEM

CROSS-REFERENCES TO RELATED APPLICATIONS

The present application claims the benefit of priority under 35 U.S.C. §119 from U.S. patent application Ser. No. 11/133,492 on May 19, 2005, and Provisional Patent Application Ser. No. 60/572,716, filed on May 19, 2004, the disclosures of which are hereby incorporated by reference in their entirety for all purposes.

FIELD OF THE INVENTION

The present invention pertains to enterprise systems. The invention presents electronic methods to organize enterprise resource planning and strategic management processes applied to the performance of enterprise functions. The present system involves the integration of information technology networks with enterprise operations. The system develops novel enterprise modeling approaches which are applied to specific enterprise functions. The system also applies to dynamic strategic management processes of enterprise operation that include development of active models to advise decision-making processes. Finally, the system applies to networks of enterprises. In the network context, the present system provides technical mechanisms that allow enterprises to have specific strategic competitive advantages to maintain market leadership positions.

BACKGROUND OF THE INVENTION

The present invention pertains to computational biology, post-genomic informatics, structural proteomics and functional proteomics. The invention uses evolutionary computation approaches to design and select simulation scenarios of protein-protein interactions for functional proteomic modeling.

Prior art patent applications that apply to the present invention mainly involve structural proteomics mapping, protein pathway discovery mapping and specific disease application protein mapping.

In Rzhetsky (molecular interaction network prediction), U.S. patent application publication number 20030068610, Palsson (operational reaction pathway identification), U.S. patent application number 20040072723, Heal (protein sequence interaction rule prediction), U.S. patent application number 20030059844, and Gustafsson (functional biomolecule identification), U.S. patent application number 20040072245, systems are developed to identify structural protein relationships. Unknown molecular interactions, protein sequence activity relationships and protein reaction pathways are mapped using computational methods involving data search space development, probabilistic analysis, comparison analysis or rule prediction. These approaches are limited to structural proteomics mapping.

Lett (image-based biological simulations), U.S. patent application number 20030018457, teaches a method to simulate structural protein image data in time series to modify model predictions. Ramnarayan (structural protein modeling of polymorphisms for drug design), U.S. patent application number 20030158672, compares healthy and mutant structural protein 3-D modeling for pharmacogenomics drug design. These patent applications model 3-D or time series data but are limited to isolated proteins' structures.

Liu (neurological disorder inhibitor), U.S. patent application number 20020006606, presents a model to inhibit JNK and MLK kinase activity to prevent neuronal cell death in neurodegenerative disease. This approach does not model the process of protein function in this specific disease application to show how the proposed therapy is effective.

Most of the research history involving the technologies of the present system—including structural protein prediction, protein pathway prediction, protein model generation, SNP identification, personalized medicine and evolutionary computation—is represented in the academic literature described below.

The development of proteomics is fairly recent. The massive data sets derived from the human genome present a vast treasure of information about proteins. Theorists from biology and chemistry have built models in which the genetic data are useful for understanding individual protein structures. Data about the structure of individual proteins are input into a multiplicity of protein databases. These databases include the Berkeley Structural Genomics Center, Joint Center for Structural Genomics, Oxford Protein Production Facility, Protein Structure Factory and Structural Proteomics in Europe. In addition to structural proteomic (SP) data collection resources, there are a number of protein interaction databases: the Biomolecular Interaction Network Database, the Database of Interacting Proteins, The General Repository for Interacting Datasets, the Human Protein Interaction Database and the Human Protein Reference Database. These databases generally input protein information collected by biomolecular researchers. But the problem emerges of how to organize this vast data reservoir in order to improve our understanding of protein processes.

Much research in bioinformatics is directed to the prediction of protein structures from raw protein data. The goal here is to model individual proteins in a 3-D way akin to capturing portraits of a range of individuals. This work is preliminary to understanding the operation and functioning of proteins in specific cellular pathways.

Professor Kim et al., at the University of California, Berkeley, have taken a step towards providing order to these protein data sets. Kim used computer analyses to calculate the relationships within a sampling of human proteins in order to develop a structural proteomic computer model. In this research, a 3-D representation of the protein fold space is presented, which is generally considered to be a sort protein periodic table (PPT). This SP data is organized to plainly show the evolution of protein structures from simple to complex forms. In this preliminary work, however, Kim does not place the PPT model into a functional model in order to give operational meaning to the fundamental protein structure data. Simulations based on the PPT are thus restricted in terms of their useful functional information.

Paek et al. at the University of Seoul in the Republic of Korea have presented a multi-layered model to represent cell signalling pathways. Software, such as Vector PathBlazer (and others), is also available to map biological pathways and present protein-protein interaction analysis, though it is generally limited and restricted because it relies on genomic and SP data sets. Using software tools for functional protein modeling, a new generation of biosystems modeling is available that will rapidly accelerate our understanding of genetic information. The HAPMAP is a database that collects information about haplotypes, combinations of single nucleotide polymorphisms (SNPs). This genetic mutation information is significant for the identifying of disease sources. However, the HAPMAP focuses on common haplotypes and not specific individuals' haplotypes and hence is not useful in the development of personalized medicine.

Personalized medicine that takes information about an individual's disease, uses experimental biological and computer techniques to trace the source to the genetic level, develops a combination of drugs to treat the disease and refines the therapy in a customized way is the goal of physicians and biological researchers. Yet only since the human genome has been deciphered has this goal of pharmacogenomics been possible. So far, only small advances have been made in which specific mutations in individuals with specific diseases, such as forms of cancer, have been traced to the genomic source. In these cases, customized combination drug therapies targeted to individual pathologies manage the disease.

The field of bioinformatics applies computational analysis to the biological sciences. One main research model for bioinformatics has been the application of artificial intelligence to biological systems. Koza and G. Fogel have done early research in this field. Koza's research on genetic programming, building on Holland's research in genetic algorithms, generally emulates biological processes of evolution by developing multiple generations of programs based on principles of mutation, sexual reproduction and natural selection in order to solve complex optimization problems. Guyon (pattern identification in biological systems), U.S. patent application number 20030172043, presents methods that use Support Vector Machines and Recursive Feature Elimination by optimizing training weights in a classifier for pattern identification. While this method applies EC techniques to gene and SP classification, it does not produce FP activity patterns that are useful for understanding proteomic processes.

Finally, the Santa Fe Institute (SFI) has accomplished sophisticated computational analyses of biological processes. SFI researchers have developed EC models for application to biological self-organizing systems in an effort to emulate these complex processes. By simulating genetic interactions, these researchers have developed a paradigm to understand the functional operation of complex evolutionary systems. However, this highly theoretical work has failed to provide useful systematic functional proteomic models or pharmacoproteomic models.

While the identification of the architecture of genes in the Human Genome Project (HGP) presents information on the construction of individual proteomic structures, much more needs to be done to advance our understanding of proteomic function. For example, if genetic diseases are caused by unique combinations of genetic mutations, the identification of these mutations is critical to understanding disease sources and finding solutions. Development of the HGP thus enables a shift in the emphasis in the biological sciences toward a personalized identifying and curing of disease. The field of human genetics shifts its emphasis to proteomics, pharmacogenomics and pharmacoproteomics.

The use of advanced computational analysis is fundamental to the field of proteomics. While most proteomics research so far has focused on predicting 3-D representations of protein structures, much work is yet to be done on understanding the operation of protein interactions in cellular pathways. One application of evolutionary computation to functional proteomics, for instance, is to compute the values of training weights of protein interactions so as to accurately emulate optimal FP operations. Though preliminary to our understanding of protein operations, these research streams leave much yet to be done.

Key Challenges

Now that the human genome has been sequenced, the next frontier for the biological sciences is post-genomic informatics and proteomics. Proteomics, the computational analysis of proteins, is divided into structural proteomics and functional proteomics. Structural proteomics seeks to understand the organizational properties of proteins from their twenty amino acid components, including geometrical and topological characteristics of protein configurations. Functional proteomics seeks to understand how proteins interact in a dynamic cellular environment.

Whereas genomics has been concerned with identifying the thirty-six thousand genes in the human genome, which consist of about three billion nucleic acid components, proteomics is concerned with a hundred times more information. Since cellular behavior is constituted of the interactions of hundreds of thousands of proteins, it is critical to understand interactions within this complex system if we are to understand the healthy, and pathological, operations of biology. By identifying the causes and organization of pathological proteomic interactions, researchers may be able not only to understand their genetic causes but also to design effective therapies.

There are several key questioned raised by functional proteomics. How can functional maps of proteins be organized from limited information? How can genetic information be connected to proteomic function and pathology? How can the function of certain proteins be predicted based on analogous protein structures, functions and interactions? How can multivariate simulations be designed that posit various protein pathway scenarios? How can dynamic simulations of proteomic processes be designed that present a methodology to select optimal as well as suboptimal simulation scenarios? How can protein irregularities and pathologies be modeled? How can cellular dysfunctions be isolated in silico and the conditions reverse engineered to discover the genetic source? How can dysfunctional protein-protein interactions be simulated?

How can pharmacoproteomic therapies be designed based on simulations of an individual's unique pathology and genetic mutations? How can these functional proteomics modeling approaches be used to engineer complex chemical compounds that repair genetic damage manifested in protein malfunctions? How can systems be designed to create DNA-based therapies and multivariate scenarios to test new chemical compounds so as to minimize side effects and injurious drug interactions?

The present invention addresses the challenges expressed in these questions.

The challenge of functional proteomics is to develop methods to visualize protein activity, typically with imperfect information. To do this, it is necessary to develop models from which simulations can be generated. Once healthy protein structures are mapped and functional proteomic activities are simulated, it becomes possible to analyze dysfunctional protein interaction processes. With information resources like the HGP and the HAPMAP, genetic information and mutation information can inform FP models about these dysfunctional protein operations. Not only can we trace the source of genetic diseases, we can now understand their complex operations, and thus move closer to developing effective therapies to manage them. So far, a large knowledge gap remains between the massive genomic data sets that we already have, on the one hand, and the useful data for biological systems that need to be developed, on the other. The expedient application of novel computational and experimental techniques is proposed to solve these problems.

As knowledge of functional proteomics increases, we should be able to identify the optimal parameters of good health, which will lead to increased longevity, and also identify the biochemical processes that cause and treat disease. In particular, the ability of the human body to fight various types of cancer and viruses, as well as degeneration manifested in aging, may be contingent on a better understanding of functional proteomics. The present invention therefore seeks to identify novel methods to meet these challenges and demonstrate (1) protein function visualization, (2) protein pathology identification and (3) personalized drug discovery and testing.

SUMMARY OF THE SYSTEM

The present invention integrates several subsystems into a bioinformatics system for functional proteomics modeling. The first subsystem involves development of an evolvable Global Proteomics Model (GPM), which relies on data from the HGP and protein periodic table (PPT) of structural proteins, and which supplies a foundation for simulations of healthy protein-protein interactions. The second subsystem involves development of simulations to identify the operation and source of individual diseases in dysfunctional protein-protein interactions. The third subsystem involves development of simulations for pharmacoproteomics in which prospective drug targets are modeled, tested and refined for optimum effectiveness for individualized therapy.

The core system uses novel hybrid evolutionary computation techniques for the search, analysis and organization of data sets and the development and selection of simulations for complex biological processes. The system employs intelligent mobile software agents (IMSAs) which operate in a multi-agent system (MAS) in order to carry out computational operations rapidly and efficiently. IMSAs work together to process parts of complex computations in order to successfully solve complex FP optimization problems. By using simulations generated by IMSAs in the three main categories of FP modeling, dysfunctional proteomic modeling and pharmacoproteomics modeling, we are able to emulate and reconstruct complex self-organizing biological systems.

The use of simulations in emulating complex biological operations is useful so as to process temporal priority geometries of proteomic processes. Not only does the system emulate and predict healthy and dysfunctional protein interaction behaviors, but it also identifies ways to correct dysfunctional processes. Development of a GPM is useful for supplying a baseline from which to compare healthy proteomic simulations. The GPM relies on data from genetic and structural proteomic databases in order to develop a functional proteomic model for understanding general protein-protein interactions. The GPM continually receives inputs from SP data sources, including protein pathway and protein-lipid pathway data sets, as these data become available.

The GPM is a meta-model that employs adaptive algorithms and is both evolvable and interactive: IMSAs draw on data sets from the GPM but also input data and analyses into the GPM from subsequent simulations drawn from the GPM. The GPM is continually optimized by active IMSA operations. Ultimately, the GPM develops models of self-organizing protein systems. The GPM is a central resource upon which FP simulations are generated. The GPM is an important frame of reference regarding healthy protein functions against which dysfunctional protein operations may be compared. In the second sub-system of the present invention, IMSAs generate simulations from data sets involving dysfunctional protein interactions. Genetic diseases typically result from mutations that manifest in the operation of mutated proteins. Effectively modeling the operation of mutated proteins helps us to identify the structural proteomic source of the disease. Once a mutated protein is identified as the origin of the dysfunctional protein process, then the dysfunctional protein geometry can be analyzed and prospective corrections developed.

Genetic diseases can be traced to highly individualized genetic causes because they typically result from multiple mutations rather than a single universal mutation. Hence, the present system describes a personalized approach to discovering the unique combinations of mutations in each individual that will manifest in a genetic disease. By comparing the dysfunctional FP simulations to the GPM, we are able to track the process of the disease in a personalized manner. Because combinations of mutations occur in most diseases, multiple mutated proteins must be targeted for an effective therapy to manage the disease on the proteomic level. Identification and simulation of these processes and disease sources are critical to proposing effective solutions.

The third subsystem of the present invention involves development of a system for pharmacoproteomics. Once a disease is analyzed via proteomic simulations, the mutant proteins' structures are analyzed, and effective customized solutions are offered. The active computational system designs a compound to solve the problem with each distinctive mutant protein. The advent of personalized medicine depends upon these techniques and systems. The solutions offered include repairing, replacing or silencing (blocking) the affected proteins.

During the testing of the proposed solution designed from simulations in the system, feedback is provided to modify and refine the customized solution, a necessary process in complex multi-pathway dysfunctions. The present system's combination of active techniques provides a useful model for adaptive personalized medicine. The three main subsystems of the present invention each employ distinctive hybrid EC techniques. In the case of the GPM, specific methods are designed to collect and analyze information for FP simulation presentations of intracellular protein pathway operations. In the case of the mutation combination identification, dysfunctional simulation scenarios are modeled and probable solutions identified.

Finally, in the case of pharmacoproteomics, FP simulations propose and test prospective solutions to mutant protein structural problems. The present system is applicable to several main degenerative genetic diseases. Cancer is a paradigm for analysis of this system because multiple mutations cause unique neoplasms which can be remedied through the understanding and repairing of proteomic processes. Neurodegenerative diseases, including Alzheimer's disease (AD), Parkinson's disease (PD) and Huntington's disease (HD), involve proteomic processes of cell death that can be curbed by applying this system.

Immunodegenerative diseases, including Rheumatoid arthritis, lupus and forms of diabetes, can be rendered manageable via the understanding of their proteomic function that is provided by this system. Aging involves processes that can be understood by simulating proteomic processes comprised in this system. Finally, the identification of optimum health is made possible by using FP simulations that give us insight into equilibrium conditions. The present system affords understanding of both these important healthy proteomic operations and the identification and solution generation of dysfunctional proteomics. The proteomic modeling of these disease categories produces the fields of oncoproteomics, neuroproteomics, immunoproteomics and gerontoproteomics, respectively. Taken together, these genetic diseases affect as many as half the population. An understanding of these complex proteomic processes may improve the quality of life for millions of patients.

Innovations of the Present System

The present system proposes numerous innovations. The GPM surpasses a structural protein database. The GPM and other database information sources generate simulations that emulate molecular protein interactions. Analysis of these complex data sources systematically organizes the protein interactions manifest in protein pathways. The production of simulations with multiple vectors and scenarios optimizes the modeling process of functional proteomics.

IMSAs are employed to link database data sets and the GPM and to analyze patterns in the data. The use of IMSAs, multiple agents of which are used cooperatively, in a parallel computer environment and a MAS operating system, solve complex problems efficiently in real time.

By using the GPM as a source of comparison, IMSAs assemble information about dysfunctional protein behavior. The analysis of combinations of genetic mutations and their FP dysfunctional manifestations as unique diseases represents a major advance in personalized disease discovery. Not only are the sources and consequences of unique mutation combinations traced and simulated, but solutions to the structural deformity of mutant proteins are identified as well. The present system identifies ways to test and refine prospective solutions for problems involving dysfunctional proteins by developing a novel process of pharmacoproteomics. This process allows for an active approach to identification and testing of compounds for personalized medicine. The system model presented here for the active discovery of unique pathologies, mutation combinations and effective therapies is novel and useful.

The present system develops and integrates novel hybrid EC techniques for each subsystem. Evolutionary search solutions for the FP scenario problem are presented. Evolutionary solutions to the pathway identification problem are also presented. A method is provided to test sets of mutations to find optimal combinations at the core of individual pathology. Dysfunctional pathway scenario identification is performed using EC methods. Drug candidate solution generation is performed using EC techniques, as is drug candidate solution testing. By showing how to identify and develop solutions to degenerative pathology problems, the present system suggests ways to fortify the immune system, slow the onset of neurodegenerative disorders, manage neoplasms on the proteomic level and identify effective anti-aging proteomics models.

Another implication of the system is that its employment of combined methods makes it possible to predict pathologies from FP simulations, which may prove useful in disease prevention.

Advantages of the Present System

Optimal therapies can be identified and selected for each individual by using the proposed biological system simulation scenarios. Since individual pathologies change, these methods and models represent a shift from universal medical approaches towards personalized medicine. Ultimately, these approaches will allow development of pharmacoproteomics, personalized medicine based on our emerging knowledge of protein interaction operations. Consequently, the methods of the present invention lie at the heart of solutions to problems involving post-genomic informatics.

The present system allows researchers to "see" specific protein interactions in both healthy and diseased processes by applying simulations. Ultimately, it is possible, with the use of the present system, to understand genes in terms of what they do and how they do it.

By using the present system, researchers will be able to focus on key mutation combinations and pathways without distraction from any irrelevant information in highly complex proteomic systems. Novel approaches to the discovery of the proteomic causes of diseases create opportunities to develop customized solutions. Identification on the proteomic level of geometric deformities allows the design of molecular level drug compounds for individual therapies which will not only accelerate drug discovery but increase efficiency and preserve valuable resources. The evolution from universal medicine to personalized medicine is thereby facilitated by the use of the present system. Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

List of Acronyms:
EC: Evolutionary computation
GA: Genetic algorithm
MAS: Multi-agent system
GPM: Global proteomic model
PPT: Protein periodic table
FP: Functional proteomics
SP: Structural proteomics
HGP: Human Genome Project
IMSA: Intelligent Mobile Software Agent
SNP: Single nucleotide polymorphism
D-AI: Distributed artificial intelligence
TK: Tyrosine kinase
RNAi: RNA interference
siRNA: Small interfering RNA
miRNA: Micro RNAs
mRNA: Messenger RNA 20
mtDNA: Mitochondrial DNA
MC: Monte Carlo The present disclosures illustrate in detail the main ideas of the present system. Since the present invention has numerous embodiments, it is not the intention herein to restrict the description of the invention to a single embodiment. The system and methods incorporated in the present invention are implemented by using software program code applied to networks of computers. Specifically, the present invention represents a dynamic adaptive distributed computer system that includes a multi-agent system (MAS).

The main embodiment of the distributed computer system is implemented with complex databases. The system incorporates intelligent mobile software agents (IMSAs) within the MAS that organize into groups for problem-solving functions. The main biological challenges, after discovery of the human genome, are (a) understanding the normal functioning of proteins on the cellular level, (b) identifying the causes of biological pathologies and (c) predicting effective therapies. An assessment of the normal functioning of proteins reveals that healthy biological system equilibrium is optimized by good health; yet it is increasingly evident that some diseases are caused by genetic damage and consequent proteomic pathology. Genetic damage may result from natural mutations or exogenous factors such as carcinogens. The process of aging, for instance, produces genetic damage at the DNA level that manifests as cellular degradation.

While genomics provides a vast amount of information about the sequencing of genes and the production of amino acids that allows us to identify the structure of proteins, it does not provide us with information about the complex operation of protein interactions on the molecular and cellular levels. We need to know the precise operational functioning of protein interactions if we are to develop and validate drug therapies. So far, drug development has been a highly inaccurate and risky proposition. Functional proteomics promises new ways to search for and design complex biochemical compounds for specific purposes. With proteomic techniques for mapping and predicting protein interactions, we can identify and test new drugs and at the same time reduce toxicity. Concomitantly, we may isolate tumor cells and identify proteins that healthy cells lack and thereby develop treatments that fortify immunological responsiveness, attack tumor development, or stifle accelerated cell development. Its focused attention on the molecular level gives functional proteomics an advantage over earlier drug therapies in solving complex problems.

A new class of drugs has proven the general functional proteomic approach to be worthwhile. Gleevec, Erbitux, Herceptin and Iressa have effectively limited the progress of some cancers. Gleevec isolates enzymes that fuel cancer growth, while Iressa blocks the EGFR (epidermal growth factor receptor) protein. In the case of Herceptin, the strategy is to target tumour cell receptors. Iressa and Erbitux are anti-proliferative agents that operate as signal transduction inhibitors, which interfere with the pathways that fuel tumour growth. With Iressa, researchers may need to screen for mutations in order to target the drug most effectively. In the future, new classes of drugs may treat a range of diseases from cancer to diabetes and from viral infections to cellular degeneration associated with aging. Ultimately, the development of personalized medicine will allow individualized treatments based on our unique genetic configurations by simply identifying and repairing dysfunctional genes. Pharmacoproteomics will enable the alignment of gene with drug therapy, with the intended effect of allowing us to control various diseases that have a genetic origin.

Biological organisms are complex self-organizing systems that consist of dynamic interactions of subsystems. Biology bridges the gulf between molecular-level information and information about integrated biological systems. Dynamic functions of biological systems include metabolic pathway processes, feed-forward cellular networks, feedback from chemical inputs on the cellular level and feedback to regulate a stable environment within complex networks. The genetic information from DNA and RNA provides "time-release" aspects of self-organizational sequences in dynamic biological systems. Whereas most models, such as protein topology, have provided a transition from the genome to three-dimensional structural proteomics, we propose a deeper understanding of the complex processes that constitute functional proteomics; this insight involves time series intervals of protein interactions, predictions and causes. To assess and analyze metabolic pathways on the molecular and cellular levels, it is essential to model them as dynamic interactions.

Structural and Functional Proteomics

Since the completion of the human genome, much work has advanced understanding of the connections between DNA data, RNA data and protein structure. DNA and RNA data organize the twenty amino acid components of proteins in specific configurations. There are four levels of abstraction in protein geometry. The primary level provides information about amino acid sequences.

The secondary level provides information about protein coils and loops. The tertiary level provides information about three-dimensional folding of proteins. Finally, the quaternary level provides information about the complex dynamic interactions between proteins. Structural proteomics deals with the first three levels, the geometric aspects of protein configuration. Understanding distinctive protein shapes is critical to understanding proteomic process interactions. Databases of structural proteomics provide information about families of known protein shapes. Since proteins are assemblages of unique configurations of amino acids, these complex structures are ordered according to similarities between families and subfamilies of proteins. Native protein structures occur in thermodynamically optimal conditions whereby temperature, Ph and electrical current are in equilibrium. If these qualities are not in equilibrium, the protein shapes will distort. In some cases, protein structure can also be computed by analysis of protein bond lengths, bond angles and torsion angles on the molecular level.

Much of structural proteomics derives from analysis of and comparison to these libraries of information. Comparisons of unknown proteins to parts or blocks of proteins in protein databases such as those at universities in the U.S., Europe and Japan illustrate the ability to test various combinations to assess and predict protein behaviors from structural information alone. The challenge is to make sense of protein analysis on the basis of limited information. Unfortunately, protein structure information and analysis alone are insufficient to understand the complexities of proteomics.

In contrast to structural proteomics, functional proteomics simulates protein macromolecular behavior. Functional proteomics organizes functional maps that emulate the operation of protein interactions. As such, functional proteomics focuses on identifying cell signalling pathways and potential pathways. As a first step toward organizing a fully developed functional proteomics with dynamic relationships, we must see protein reactions as simple biochemical mechanics with molecular causes and effects. In the simplest case, a protein molecule will act on another protein molecule, typically the nearest neighbour. This molecular cause and effect relationship leads to more complex biochemical kinetics in which reactive events are stimulated by turning chemical thresholds on and off.

Chemical chain reactions of molecular level proteins based on DNA information supplied to the proteins' amino acid components thus occur in the context of a complex biological system. As we develop a fuller picture of multiple reactions, we discover that there are multiple protein reaction pathways.

The combining of multiple protein reaction pathways leads to construction of models which represent highly complex protein-protein interactions. The challenge here is to reconstruct, and phenomenologically describe, proteomic interaction processes. Multiple vector reactions in a complex self-organizing system require a mapping of dynamic protein interactions. Since these interactions occur in the cellular environment, complex multi-pathway cellular interactions that feature feedback mechanisms are also modeled in functional proteomics. Functional proteomics represents the manifestation of the dynamics of structural proteomics. Because much of structural proteomics is contingent on protein databases, functional proteomics also constructs complex databases that identify causal relationships between proteins. One way to track protein behaviors is to isolate key subsystems such as cell type and correlate this information with protein variables. Another way to track protein behaviors is to differentiate the main states of the protein both in and out of equilibrium.

The fundamental attribute of functional proteomics is its temporal dimension. Since protein interactions are temporally based, the temporal dynamics of protein network interactions represent genetically stimulated protein multi-pathway sequences. These sequences may be represented as isolated events or as complex interaction dynamics. One of the challenges for both genomic informatics and functional proteomics is to identify the genetic triggers of biochemical functions. Another challenge is to identify the mechanisms of cell receptor proteins that are targeted by other proteins acting as triggers which turn complex protein interaction sequences on and off. As we obtain more empirical evidence we are more precisely able to identify and model complex proteomic developmental processes such as embryonic growth.

A particularly useful benefit of functional proteomics is its ability to predict protein protein interactions as well as protein reactions to biochemical substances. Protein pathway predictions can be made by identifying similar structural proteins in protein databases and comparing their behavior. As the interaction combinations become much more complex, it is necessary to rely on computational resources to model the network interactions between proteins. Because of the high number of variables in complex functional proteomic modeling, the adopted models have constraints on predictive capability in an inverse correlation to the degree of complication. One way to model multivariate protein interaction multivector pathways is to develop multiple scenario simulations. This approach allows us to add or remove variables in a visual replica and to predict the consequences of prospective reactions. This approach also allows us to reverse engineer chemicals based on the analysis and synthesis of our understanding of biochemical processes.

Proteomic Computational Modeling Methods

There are several main approaches to obtaining empirical data on the structure of proteins. These include 2-D gel, mass spectrometry, microarrays and X-ray crystallography. The first two approaches provide images of protein sequences, while microarrays measure slight differences between similar proteins. X-ray crystallography is a process in which atomic level images of proteins are obtained. When combining these empirical methods for obtaining data on protein structure with genomic information about DNA sequencing, we are better able to assess primary and secondary information about individual proteins. However, the use of this empirical data to build 3-D models of protein folding on the tertiary level and 4-D models of protein interaction on the quaternary level requires adoption of advanced computation models.

Bioinformatics incorporates multiple evolutionary computation techniques to solve problems with the goal of obtaining information for building models of complex protein behaviors. These techniques include the use of artificial neural networks which learn and adapt for data mining, data search and pattern matching in large databases and development of self-organizing maps. For example, multiple sources of inputs in a complex pathway of numerous vectors may point to a dominant pathway in which the threshold of inputs are ranked by priority; calculation of these inputs and thresholds may be performed by ANN processes. In another example; multivariate analyses and regression analyses may be used to perform these modeling calculations. Such combination of computation methods into hybrid approaches results in optimal effect.

Because part of the challenge of structural proteomics is to mine large protein databases in order to assess similar patterns, the use of complex data mining strategies that involve active search and pattern matching processes is computationally more efficient than passive approaches. Intelligent software agents for search are therefore proposed to produce complex dynamic mapping results. Multivariate regression methods provide ways to isolate variables for multifactoral analysis. The classification of sequences according to the families and sub-families of protein classes allows researchers to isolate these variables on the atomic level. A comparison of new proteins with familiar proteins reveals new protein attributes.

In addition, comparisons of unknown proteins with interspecies protein information reveal protein factors with features that are common to multiple species; hence we establish a larger database to draw upon than that derived from a single genome.

Cluster analysis uses pairwise similarity analysis techniques to assess the parameters of similar groups. Decision tree analysis can also be useful for discovering the classification of protein structures.

Computational approaches to the development of structural protein databases include the use of complex statistical methodologies such as Bayesian learning, simulated annealing, Monte Carlo methods, Support Vector Machines and hidden Markov chains. In most cases, these methods are adopted in environments with imperfect information in which random search is performed from a sample of data in order to narrow the range of model development. For the applications of functional proteomics, vector probabilities are created via these statistical techniques. These techniques allow us to identify factors that are missing from a solution and thus to identify missing components. The testing of multiple potential variables and their interpolation within a restricted search space to optimal solution candidates constitutes a way to solve this class of proteomic problems. Combinatorial optimization techniques are used to assess the unique combinations of molecules of a given protein when only limited information is available. In particular, combinatorial optimization approaches are useful in developing models of functional proteomics in which a number of complex combinations of proteins interact with multiple vectors and pathways. Distributed and parallel computation systems are employed in order to calculate the optimization parameters of these complex functional proteomic models.

One of the goals of structural proteomics is to predict folding properties of protein behavior. With the use of probabilistic analytical techniques we are able to predict protein properties within a limited range of probability. Similarly with functional proteomics, the use of probabilistic analytical techniques allows us to predict vectors of protein reaction and interaction but only within limited ranges. Pathway matching techniques can be applied by comparing the pathways of known protein interactions with limited data about newly discovered proteins. Machine learning approaches to these predictive models accelerate their calculations. Evolutionary computation involves development of multiple generations of solutions to complex computational problems. The several types of evolutionary computation include genetic algorithms, genetic programming and automatic programming methods. It is useful to combine the best parts of these methods into an integrative model for applying hybrid evolutionary computation methods in order to solve complex functional proteomic problems. The application of EC techniques may be accelerated by using distributed artificial intelligence technologies.

The use of multiple parallel computation approaches enables the testing of protein functioning. It is advanced that the use of intelligent mobile software agents in D-AI can solve the problems of functional proteomics. For example, an intelligent search agent can perform data mining with greater accuracy, predictive probability (within a range of scenarios) and greater speed. Intelligent mobile software agents (IMSAs) operate in distributed computer systems. In one operation, an IMSA makes an initial map of a protein interaction that provides information about a newly discovered protein network. By comparing the proteins with existing protein interaction databases, new statistical information is added and the map is updated. This information is used to design a dynamic map customized for a specific protein interaction sequence. Real time dynamic comparisons of active biochemical and cellular interactions with known databases provide a basis for customized proteomic model development. IMSAs are used for identification of specific protein relationships, for active pattern matching of similar functional protein database processes and for comparisons of different types of chemical analyses (including across genomes) and reactions.

Using these methods and tools, we may work backwards from a particular problem involving cellular pathology and thereby narrow the pool of data to be analyzed. By assessing the classification of analogical protein structures we are able to identify similar functional protein pathways, a process that narrows the data scope appreciably. These computational approaches are active, efficient and synthetic and therefore well suited for functional protein interaction analysis and synthesis. The use of these computational methods and models markedly accelerates experimental processes and adds immeasurably to our acquisition of valuable knowledge.

Dynamic Simulations

Computer simulations are a central part of proteomic analysis. With them, information about proteins is organized, analyzed and evaluated. For example, in structural proteomics, protein folding calculations of possible geometric configurations are made based on sequence analyses. Modeling functional proteomic data sets using computer simulations is more complex.

The phenomenological modeling of protein interaction pathways is necessary for understanding protein reactions, protein effects and drug effects. Used in reverse, these same models assess the protein interaction causes of cellular pathologies.

One of the best ways to model functional protein interactions is to develop contingency simulations of complex processes. Thus a functional proteomic model would have not only a limited range but also simulation scenarios with contingencies based on limited, and updated, information. These modeling scenarios are hybrid simulations, that is, they are both discreet and continuous based on multiple protein behaviors. The simulation and modeling system consists of a hypothetical model, a database, a simulation engine and a visualization engine. Simplified simulations are created by removing as much inessential data as possible in order to focus on a particular problem. For instance, using this reduced information model we can assess the immediate consequences of a biochemical reaction, such as a small molecule ligand interacting with a large protein molecule. As the model evolves, we fill in the pieces of the puzzle, moving from a partial map, in which an outline is obtained with limited information, to a more robust model. This simple simulation is useful for assessing a limited range of protein reactions. This model also helps isolate anomalies.

Multivariate simulations that develop dynamic models for functional proteomics emphasize different phases of events, adding and subtracting variables to develop a map that emulates the operation of protein pathway vectors. The various factors are analyzed and evaluated by comparisons with known protein interaction sequences. With this model, we are able to colour code the various pathways in order to separate the related proteins in a complex self-organizing system and thus assess more complex structural anomalies. The selection of optimal scenarios from among the various proteomic simulation runs will provide the most transparent understanding of functional protein interactions within the constraints of limited information. This multivariate simulation approach allows for the accelerated substitution of experimental processes.

Simulation scenarios apply experimental data to develop contingency scenarios based on the limits of information but are constrained to using probabilistic inference. We develop adaptive deterministic molecular spatio-temporal simulations based on an emerging knowledge bank. These multifaceted protein reactions are represented as contingencies in simulation scenarios in which input variables are modified to assess changes in outcomes. In this way, we can test various combinations of molecules with predicted results.

By producing functional protein simulations with multiple scenarios based on input variable limits, we are able to increase the probabilities of accurate predictions of protein pathway vectors and protein-protein interactions based on information from similar known protein families. These techniques allow us to anticipate possible similar predictions of protein interactions based on similar comparisons. As an example of this, we can separate the healthy operation of cellular function from pathological operation and seek to identify the protein pathway functions that cause disease. By specifying the narrow conditions of optimal health we are better able to identify pathological conditions. By using these complex simulation scenarios for functional proteomics we are able to test and evaluate drugs for specific pathologies. By reversing this same approach, we may begin with pathologies and work to identify protein pathway causes of disease which allow us to develop drugs that target specific proteins for accelerated drug discovery.

General System Architecture and Dynamics

DESCRIPTION OF THE DRAWINGS

FIG. 1 is drawing of system layers.

FIG. 2 is a schematic diagram of a biological model process.

FIG. 3 is a flow chart of a system model overview.

FIG. 4 is a flow chart of a Global Proteomic Model (GPM) overview.

FIG. 5 is a schematic diagram of a computer system overview.

FIG. 6 is a schematic diagram of a general simulation typology.

FIG. 7 is a schematic diagram of an Intelligent Mobile Software Agent (IMSA) system model.

FIG. 8 is a chart of levels of protein model abstraction.

FIG. 9 is a chart of the GPM emphasizing categorization of protein structures and protein functions.

FIG. 10 is a chart of the GPM emphasizing protein functions according to sub-functions.

FIG. 11 is diagram of the protein development process.

FIG. 12 is a chart of protein modeling types for structural proteomics and functional proteomics.

FIG. 13 is a list of structural proteomics properties.

FIG. 14 is a list of structural proteomics topology typology

FIG. 15 is a chart of protein functional activity.

FIG. 16 is list of the range of protein combinatorial interaction.

FIG. 17 is a list of temporal dynamics categories of protein network interaction.

FIG. 18 is a schematic diagram of a search for the efficient model of structural proteomics.

FIG. 19 is a schematic diagram of a map of proteomics models.

FIG. 20 is a diagram of pathways.

FIG. 21 is a schematic diagram of a process of protein macromolecule binding with micro molecules.

FIG. 23 is a schematic diagram of dysfunctional structural proteomic geometric shapes that interact to produce pathological operation.

FIG. 24 is a schematic diagram of a multi phasal simulation of protein-protein behavior.

FIG. 25 is a flow chart showing layers of protein function.

FIG. 26 is a flow chart showing functional protein map development.

FIG. 27 is flow chart delineating pathological protein pathway modeling.

FIG. 28 is a schematic diagram of a dysfunctional proteomics model.

FIG. 29 is a schematic diagram of healthy and dysfunctional protein processes compared.

FIG. 30 is a diagram of a risk assessment analysis of mutations.

FIG. 31 is a flow chart of a disease management process.

FIG. 32 is a flow chart of an individual pathology assessment based on analysis of mutations.

FIG. 33 is a flow chart which describes the construction of an individualized haplotype model.

FIG. 34 is a flow chart describing a reverse engineering of customized pathology model.

FIG. 35 is a flow chart of a mutation analysis method.

FIG. 36 is a flow chart of a simulation scenario selection for pathology prediction.

FIG. 37 is a flow chart of an identification process of individuals in groups that share SNPs and pathologies.

FIG. 38 is a flow chart of a pharmacoproteomic system model.

FIG. 39 is a diagram of solution generation for pharmacoproteomics.

FIG. 40 is a diagram of a comparison of pathology tracking with targeted drug process.

FIG. 41 is a flow chart describing a proteomic dysfunction identification and solution selection process.

FIG. 42 is a flow chart describing a solution generation of pathology.

FIG. 43 is a flow chart showing a semi-custom medicine process.

FIG. 44 is a chart of types of management protocols of genetic pathology that provide solutions to dysfunctional protein structures.

FIG. 45 is a flow chart showing active feedback to track protein based medicinal therapy regulation.

FIG. 46 is a flow chart of pharmacoproteomics modeling describing real time simulations for individualized medicine.

FIG. 47 is a chart of degenerative diseases.

FIG. 48 is a chart delineating neoplasms by type, mutation source and oncoproteomic solutions.

FIG. 50 is a schematic diagram of the pharmacogenomics of neuronal death mechanisms.

FIG. 51 is a flow chart describing human immune system operation.

FIG. 52 is schematic diagram showing the pathophysiologic scheme of sickle cell disease.

FIG. 53 is a chart delineating the pathology of gerontoproteomics.

FIG. 54 is a chart showing hybrid modeling techniques applied to proteomic simulations.

FIG. 55 is a flow chart showing the modeling system architecture.

FIG. 56 is a flow chart describing a model generation process using IMSAs.

FIG. 57 is a flow chart describing a pathway generation process using IMSAs.

FIG. 58 is a flow chart describing an optimal simulation generation using IMSAs.

FIG. 59 is a flow chart describing a pathology protein pathway simulation generation using IMSAs.

FIG. 60 is a flow chart describing optimal dysfunctional protein pathway simulations using IMSAs.

FIG. 61 is a flow chart describing the process of identification of mutant protein(s) using IMSAs.

FIG. 62 is a flow chart describing the process of mutation combination generation and selection using IMSAs.

FIG. 63 is a flow chart describing the gene blocking process of mutant protein source of pathology using IMSAs.

FIG. 64 is a flow chart describing the solution to the problem of protein mutations using IMSAs.

FIG. 65 is a flow chart describing the pharmacoproteomic process of testing protein solutions using IMSAs.

FIG. 66 is a chart illustrating simulation typology categories.

FIG. 67 is a flow chart showing a Monte Carlo statistical technique applied to protein data organization in a dynamic process.

FIG. 68 is a flow chart showing a Monte Carlo statistical technique applied to protein mutation data organization in a dynamic process.

FIG. 69 is a flow chart showing the application of RNA interference techniques used to silence the production of a protein.

FIG. 70 is a schematic diagram of the GPM operation.

FIG. 71 is a flow chart describing the GPM as an evolvable meta-model.

DETAILED DESCRIPTION OF THE DRAWINGS

Figure 22:
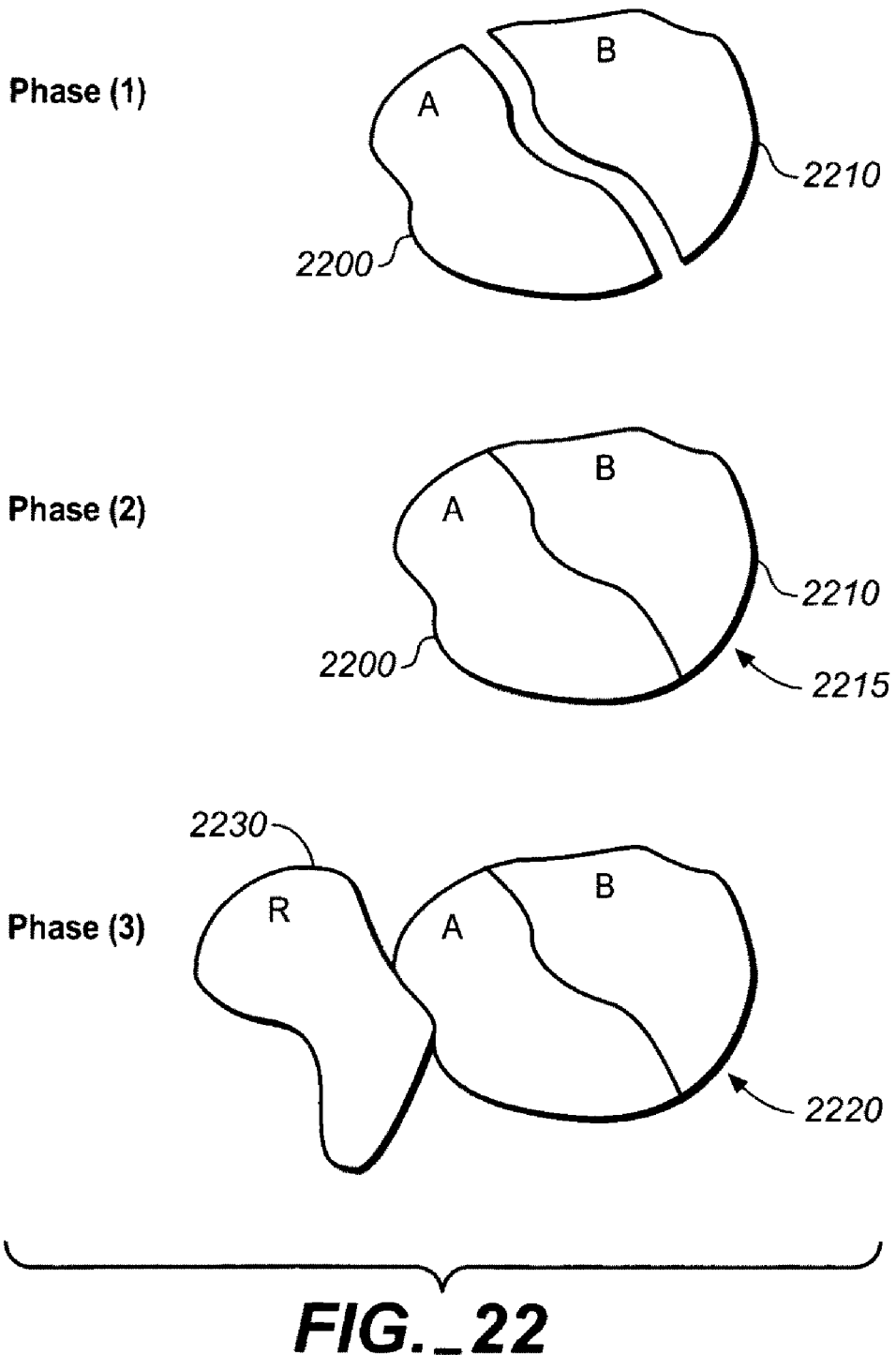
FIG. 22 is a schematic diagram of structural proteomic geometric shapes that interact to produce protein functions.

The main system incorporates a number of system layers or operational protocols. FIG. 1 illustrates the layers of the functional proteomic modeling system architecture. Working from the bottom up, the first layer (100) represents human genome databases. Layer two represents structural proteomic libraries (105), which are informed by the human genome databases. These SP libraries inform the dynamic Global Proteomic Model (GPM) (110) at layer three. From the GPM, functional protein maps are drawn (115) at layer four. With FP maps, the modeling of protein behaviors (120) can be performed at layer five. Intelligent Mobile Software Agents (IMSAs) (130), using evolutionary computation (EC) in a distributed artificial intelligence (D-AI) based multi-agent system (MAS) use the protein behavior modeling information at layer six. Simulations of protein interactions are then drawn (135) at layer seven.

Mutation combinations (haplotypes) are identified for individual pathologies (140) at layer eight based on comparisons with information from prior levels. Pharmacoproteomics (145), which customizes of medical therapies for unique genetic problems, occurs at layer nine. The distinctive pathology applications category typology (150), which develops specific treatments for a range of disease types, is at layer ten. Finally in the present system, specific genetic degenerative field categories of oncoproteomics (155), neuroproteomics (160), immunoproteomics (165), and gerontoproteomics (170), which deal with, respectively, cancers (neoplasms), neurodegenerative diseases, immunodegenerative diseases and aging, as well as other genetic diseases (175) and optimal health (180), represent the eleventh layer.

FIG. 2 shows a multi-level biological model process from gene structure (200), RNA replication (210), protein structure assessment (220), protein structure prediction (230), protein function assessment (240), protein-protein interaction (250) and, finally, to the aggregate functional proteomic effects (260) within a healthy individual. This sequence is unidirectional from genetic structure to healthy proteomic operation. FIG. 3 illustrates the system model overview. From protein structure databases (300) are derived a protein periodic table (PPT) (305). From the PPT is derived the Global Proteomic Model (GPM) (310) and from the GPM, by using IMSAs (315), normal pathway functional representations are determined (320). From the functional pathway information, which includes protein interaction maps and interactive variable control maps, we derive proteomic modeling (330), which describes self-organizing proteomic group behaviors as well as combinatorial optimization representation of distinct sets of proteins. From this information we can derive specific proteomic simulations (335) which identify, in this context of the operation of healthy protein function, the most efficient pathway of functional proteomic interactions.

After healthy proteomic function is revealed, the system identifies mutation combinations (haplotypes) for specific pathologies in distinctive disease categories (340). This dysfunctional proteomic information is sometimes reverse engineered from pathology to the genetic source (345). But in another mode of the system, a personalized medicine system is developed from the identification of dysfunctional proteomic information (350). By using IMSAs (355), the system builds customized model(s) of unique proteomic pathology (360) and develops customized solutions to a specific pathology (365). By applying the solution (370), testing the solution (375) and refining the solution (380), a customized management of the disease is possible (385).

The discussion below of the functional proteomic modeling system follows this general model. The first seven figures cover the general system architecture. FIGS. 8 through 26 articulate the general model of functional proteomics modeling for healthy operations. FIGS. 27 to 37 discuss the analysis of functional proteomics modeling of dysfunctional proteins. FIGS. 38 to 46 teach pharmacoproteomics modeling. FIGS. 47 to 53 review disease types and the application of the system to these distinctive genetic degenerative pathologies. FIGS. 54 to 65 generally discuss the role of IMSAs in the system (with FIGS. 54-58 for normal FP, FIGS. 59-62 for pathology and FIGS. 63-65 for pharmacoproteomics). FIGS. 66 to 68 deal with aspects of simulations.

The Global Proteomic Model (GPM) is generally described in FIG. 4. From the main GPM (400) are generated customized functional proteomic (FP) "maps" (410). These maps provide protein interaction diagrams and multivariable control to guide the maps. Dynamic four-dimensional animation modeling (410) can be derived from the FP maps, delineating self-organizing group behaviors. Combinatorial biochemistry also models distinct sets of proteins using this dynamic modeling approach. Finally, specific simulations (430) are derived from the modeling. Optimal pathway mapping, including dynamic temporal illustrations, can be made of protein-protein interactions from the modeling information. See also FIG. 70 below.

In FIG. 5, the computer system overview is illustrated. The local databases (500) are accessed through an interface from either the Internet (for instance, the World Wide Web) (510) or local access portals (520). The system has backup (530) and redundancy (540). The system also has network interfaces with external databases (550). The core software operates within a multi-agent system (MAS) that interoperates within the local and external databases. IMSAs operate within the MAS.

FIG. 6 briefly shows the main classes of simulations (600) that are used in the present system. First, functional proteomics (605) models simulate optimal protein pathway operations. Second, dysfunctional proteomics (615) simulations are modeled. Finally, the dynamic process of personalized medicine is modeled (635). Refer to FIG. 66 for a list of simulation categories corresponding to these main modeling types.

The main simulation types indicated in FIG. 6 correspond to the main categories of modeling employed in the present system. FIG. 7 illustrates these main modeling categories and the processes that correspond to the main categories. The first type of IMSA (700) develops the GPM (705), from which FP modeling (710) and optimal FP pathway simulations (715) are generated. The second type of IMSA (720) develops the pathology model (725), at least in part by comparing mutations to the GPM, and pathology structural proteomic (SP) pathway simulations (730) (from the pathology model and from comparisons with the GPM). From the pathology SP pathway simulations and from the FP modeling (710) (generated from the GPM), pathology FP pathway simulations (735) are generated.

A third type of IMSA (740) develops the pharmacoproteomic model (745), from which solution development simulations (750) are produced in silico. Pathology FP pathway simulations also inform solution development simulations. From these solution development simulations, solution testing (755) is performed in which feedback is obtained about the effects of the solution. From this testing process, the solution refinement process (760) is implemented, eventually leading to optimum solution scenario (765) development and selection.

FIG. 8 is a chart indicating the levels of protein model abstraction. At the first level is raw protein data, which is input into protein databases. On the second level, proteins are viewed as two dimensional and are organized by individual protein groupings based on similarities, which are then stored and reorganized in protein databases; from these data sets protein structure predictions are made. On the third level, which occurs in three dimensions, the protein periodic table (PPT) is developed which organizes classes of protein families. On this level, the evolutionary origins of proteins can be determined because we can see the generation of complex from simple proteins. Protein structure predictions allow for the organization of individual protein properties on this level. Finally, on the fourth level, protein operation and interaction is organized in four dimensions in the Global Proteomic Model (GPM). Dynamic protein interaction is modeled using IMSAs and multivariate analyses to simulate the operation of protein in experiments in silico. At this level of abstraction, the functional proteomics (FP) model identifies the parameters of protein conditions and protein interaction potentials.

FIG. 9 illustrates the protein structure categories indexed with their functions in an outline of a GPM. Four axes, A, B, A/B and Composite, organize families of proteins in a classification scheme. These aspects of the organization of protein families by structure are further correlated with protein function at the top scale. In general, proteins can be divided into binding and activities categories and further subdivided into general binding, chemical binding, specialized activities and electron transport activity as well as miscellaneous functions. In practical terms regarding their use on the cellular level, these main categories of protein functions embrace the majority of protein utility. By creating this classification scheme we can see the logical integration of structure with function of the main families of proteins. See the discussion below at FIGS. 70 and 71.

The functional classification of protein families is further delineated in FIG. 10 in which DNA binding, protein binding, ATP binding, RNA binding, nucleic acid binding and calcium, magnesium and zinc ion binding occur in over half of all proteins. Binding is thus a fundamental aspect of protein behavior; blocking or enhancing binding processes is critical to the management of health and the maintenance of degenerative diseases. Similarly, oxidoreductose activity, electron transport, catalytic activity, structural molecule activity, electron transporter activity, receptor activity, hydrolase activity, endonuclease activity, signal transducer activity, protein kinase activity, nuclease activity and serine-type endopeptibase inhibitor activity taken together embrace more than a third of protein functional activities.

Taken together, almost ninety percent of all protein functions are related to binding and cellular process activities. This being the case, the development of a GPM based on understanding of the function of proteins is critical to our understanding of biological processes. Our awareness of these two central abstract functions of binding and activities accords an opportunity to develop a classification scheme that goes far beyond the limits of individual structure protein topologies. Nevertheless, understanding the complex interactions of functional proteomics requires effective modeling and simulation of these natural processes that is the chief aim of this system to represent.

The protein development process is illustrated generally in FIG. 11. Moving backward, protein-protein interaction is modeled in the context of cellular pathways (1100) from protein-protein interaction simulations (1110). Protein protein simulations are derived from protein function models (1120), which are themselves derived from protein structure models (1130). Protein structure prediction (1135) is also derived from protein structure models, which are themselves derived from both amino acid (1140) models and RNA (1155) models. The genome (1150) is the core foundation for individual DNA (1160) modeling. This central dogma about the organization of proteomics and genomics rests as the centerpiece of our knowledge of biology. Although we have learned much about the genome in recent years, there is nevertheless much more to learn about the complex self-organizing processes of the proteins produced and governed by our DNA.

In order to further our understanding of proteomics, protein modeling systems generate specific representations of protein interactions. FIG. 12 describes the main protein modeling types for structural proteomics and functional proteomics. Protein structures can be topologically described in three dimensions of Cartesian space. The "prediction" of protein structures represents protein topology and overall architecture, but structural proteomics also seeks to represent the optimal equilibrium conditions of individual proteins. In fact, understanding the functioning of proteins will ultimately help us more fully understand the structural aspects of proteomics as well because operational data will provide information on equilibrium conditions. Ultimately, the GPM will inform a protein periodic table (PPT) as much as a PPT or structural protein data will inform the functional GPM.

On the functional side of the modeling of proteins represented in FIG. 12, we see four-dimensional (that is, three spatial dimensions plus the temporal dimension) representations of protein operations. Modeling of FP can be forward or backward. FP representations can delineate optimal or sub-optimal protein interactions as well as protein reactions to processes.

Protein function relies on protein structure for its main building blocks. Consequently, we need to understand the main components of proteins, which are represented in FIG. 13. Proteins are comprised of the chemicals carbon, hydrogen, nitrogen, oxygen, phosphorous and sulphur. In addition to their chemical aspects, protein molecules have electrical aspects (based on their atomic components) which manifest as electron binding energies, ionization energies, nuclear charges and electronegativities. Finally, temperature and pH are qualities that influence the operation of proteins. Taken together, these molecular features and their complex combinations represent the ultimate building blocks for a protein periodic table. Further aspects are developed in FIG. 14.

FIG. 14 lists the structural proteomics topology typology. Since protein structures appear as clumps of ribbons and strings, determining their geometrical configurations is central to understanding their structure and function. The structural criteria for proteins include geometric surface shape type, protein fold type, amino acid aggregate configuration type, combinatorial geometry (and combinatorial biochemistry) and protein structure conditions (including sub-optimal conditions). Structural proteomics is generally seen in optimal equilibrium conditions. FIG. 15 provides a list of categories in which there are sub-optimal and post-optimal conditions for protein structure operation. These SP conditions include binding, transport, regulation, signalling, receptor, target, inhibitor and disruption features. In all cases, the protein structure is evaluated according to conditions that are intracellular. That is, SP analysis is made based on understanding the context of protein operation. The challenge is to understand, and to model, the operation of a protein in action.

As the attempt to model proteins moves from understanding a particular protein's structure to the interoperation of multiple proteins, the range of complexity increases. The representation of protein function is made in the GPM with multiple criteria that go beyond the PPT descriptive categories limited to SP. Because the universe of proteins is extremely complex, it is necessary to narrow the range of criteria in order to focus our understanding of their behaviors. FIG. 16 shows a list of these complex criteria.

The FP criteria specified in FIG. 16 are (1) narrowing the range of proteins that combine with other proteins to perform a specific function, (2) narrowing the range of protein networks with specific functions, (3) narrowing the range of macromolecular assemblies of interacting proteins, (4) specifying the cellular pathways (within and between) with specific range of protein functions, (5) specifying the nearest neighbour protein interaction, and (6) narrowing the range of proteins that do not combine with other specific proteins and thus ruling them out of the equation. These aspects of protein combinatorial interactions allow us to focus our FP simulations in a useful way.

FP interaction criteria generally emphasize the active mode of systemic operation in contrast to the emphasis in SP on merely portraying an individual protein. Physical motion of groups of interacting entities is a key aspect of protein function. In FIG. 17, the main temporal aspects are illuminated. These temporal components are (1) discreet event isolation, (2) threshold event identification, (3) time release aspect of protein pathway sequence, and (4) statistical trial and error as a key method for assessing protein inter-operation compatibility in cellular pathways. These temporal aspects capacitate our understanding of complex functional proteomic systems. In order to understand FP we must first understand the general principles of SP which provide the main building blocks of system operation.

FIG. 18 illustrates the search for an efficient model of SP. After data is collected on protein structure (1805) from a protein database (1800), a Monte Carlo algorithm is applied to the protein structure data in order to break random data into clusters for the assessment of protein structures (1810). Protein data is ordered by developing a pattern based on common elements of protein structures (1815). Less relevant data is pruned out (1820) and known structural protein families are organized (1825). The initial phases of a self-organizing map (SOP) of protein structures are developed (1830). A Bayesian algorithm is applied (1835) to SOP data sets and more data is collected in a process of continuous data analysis and organization. From the SOP and the known structural protein families, matches are made of protein structures by comparing protein classes and selecting the most relevant (1840). From this organized data, a structural protein map is constructed (1845) and the SP map is updated (1850).

FIG. 19 illustrates the organization of proteomics models. From the human genome, specific individual genetic architecture (1900) models are generated, which produces the structural proteomic periodic table (S-PPT) (1910). From the PPT, a functional GPM is generated (1920). From the GPM, protein-protein interaction behaviors are simulated (1930), healthy pathway protein interactions are simulated (1940) and dysfunctional pathway protein interactions are simulated (1950), while reverse simulations trace the cause of pathology (1960). From these simulations, haplotypes (mutation combination sets) (1970) are identified by comparing healthy and pathology FP data. Individual mutation combinations are identified (1980) and modeled for specific degenerative pathologies (1990).

Protein interactions occur within cellular pathways. FIG. 20 provides an example of two parallel and interacting pathways. In pathway "A", protein 2000 interacts with proteins 2002 and 2006. Protein 2002 interacts with proteins 2004, 2008 and 2012. In pathway "B", 2030 interacts with 2032 which then interacts with 2034. Protein 2006 interacts with protein 2034 in pathway "B", while protein 2034 interacts with protein 2012 of pathway "A". Protein 2008 interacts with protein 2010, which interacts with protein 2014. Protein 2038 of pathway "B" also interacts with protein 2014 of pathway "A". 2014 continues to interact with protein 2016, which interacts with protein 2018 and 2020. Protein 2038 in pathway "B" interacts with both proteins 2040 and 2042. Protein 2040 interacts with proteins 2020 and 2044. Protein 2044 in turn interacts with proteins 2046 and 2048. Protein 2020 in pathway "A" interacts with proteins 2024 and 2028. At each stage in these parallel processes the addition or subtraction of carbon atoms change the molecular structure of each succeeding event. These protein interactions generally rely on thresholds before continuing on to each successive level of interaction. These successive threshold events rely on values that can be numerically assigned to proteins at various levels. Calculations of these values, and thus prediction of the event thresholds, is performed by employing various combinations of evolutionary computation, machine learning and artificial neural network techniques.

Much of the process of FP relies on the binding properties of interacting proteins. FIG. 21 shows a multi-phasal process of protein macromolecule binding with micro molecules. In phase 1, the small molecule protein moves from position A' (2105) to A (2110) to bind with the large protein R (2100). In phase 2, the micro-molecule B moves from position B' (2120) to position B (2125) to bind with R (2115). In addition, micro-molecule T moves from position T' (2130) to position T (2135) and micro-molecule Z moves from Z' (2140) to Z (2145) to bind to A (2150). A then binds with R. In the phase 3, T (2170) binds with A while C (2155), B (2160), A (2195) and Z (2180) bind with R (2150).

For optimal binding, proteins require a compatible geometric fit. One of the generators of pathology on the molecular level is the dysfunctional geometric interaction of proteins that are generated from mutations. Examples of this phenomenon may be observed in sickle cell anaemia (FIG. 52) and in cancers and other degenerative diseases. Particular molecules missing from, or added to, a protein will generate a cascade of pathological manifestations in the geometries of interacting proteins. FIGS. 22 and 23 generally illustrate this phenomenon.

In FIG. 22, healthy proteins A and B (2200 and 2210) interact in phase 1. In phase 2 the two proteins (A and B) unite to form a macro-molecular unit (2215). In phase 3, a complementary protein, R (2230), binds to the appropriate space on the conjoined protein (2220). In FIG. 23, however, the proteins are dysfunctional because of a genetic mutation. In this case, in phase 1, A (2300) binds with B (2310) and in phase 2 the conjoined A and B unite to form a macro-molecular unit (2320). But unlike in the case of FIG. 22, in FIG. 23 A has a deformity, represented here on its left side as an exaggerated deep crevice, which binds with Z (2340) to create a dysfunctional pathology in the context of cellular pathway interoperations. The geometrical aspect of non-optimal protein binding is a core concept in understanding the pathologies of genetic disease.

In FIG. 24, protein B (2420) binds to protein C (2425) at phase 2. In phase 3, A (2430) also binds to C (2440) (where B (2435) is already conjoined from the earlier phase). The entire assembly from phase 3, C (2455), then binds to D (2460). This multi-phasal illustration shows the complex interaction processes of micromolecules with macro-molecules.

FIG. 25 shows layers of protein function. FP interactions occur in the context of cellular pathways (2500). A first layer is introduced to this pathway (2510) and then a second layer is introduced (2520). Protein functions are timed to interact with these layers. In fact, multiple layers may exist in a cellular pathway or between multiple pathways. The issue of timing of protein interactions is key to FP and relies on the emergence of thresholds to determine the precise timing of behaviors. Specific proteins and the genes that produce them are "programmed" to time the operation of the cellular system with substantial precision. Much of FP is based on the organization of these event interactions. Proteins interact in ways that activate other proteins to perform functions and so on throughout the cellular system. These observations are important to understanding and simulating FP models. See the discussion below after FIG. 71.

In order to map FP operations, the GPM serves as a major model, informed by SP data sets and by the PPT, to draw from in order to develop healthy cellular pathway simulations and general protein function maps. FIG. 26 shows the development of a functional protein map. After two proteins are compared (2600), arranged into categories based on common structural elements (2610) and compared with other proteins (2620), they are sorted into structural protein categories (2630). The SP organization is filtered using FP data (2640), and the two proteins are re-sorted and mapped into categories based on functional protein organization. The protein functions are analyzed (2660) based on the evolution of proteins and sorted into structural categories (2670).

Knowledge of protein function affords greater insight into the meaning of individual proteins. Since many proteins appear to be very similar but function very differently, assessing the organization of protein structures by the criteria of protein function, allows us to appropriately reorganize large sets of proteins. Since the structural protein data can be organized from simple to complex, generally mirroring the historical evolution of proteins, we can cross reference the SP with FP data to elucidate the more evolved functions. These data filtering processes provide us a context of empirical analysis of protein interactions in cellular systems and allow us to organize protein architectures and processes into a general protein model. See also the discussion at FIG. 71 below.

According to the current dogma, protein pathology is caused by genetic mutations. These mutations combine in unique ways to present in each individual's pathology. The challenge of dysfunctional proteomics, or FP pathology, is to identify the unique combination of mutations, or haplotypes, that cause specific diseases and to simulate the specific dysfunctional protein interactions. Once the dysfunctional protein interactions are detected, then the source of the deformity in the geometries of specific proteins is identified and solutions presented to repair these specific (and sometimes unique) deformations. FIGS. 27 to 37 apply to identification and analysis of dysfunctional proteins that cause degenerative diseases.

In FIG. 27, both endogenous (2700) and exogenous (2705) causes of mutations create a genetic mutation (2710). An endogenous mutation manifests in RNA (2720) while an exogenous mutation also manifests in RNA (2730). This is important, because the RNA presents an intermediary process between the DNA and the production of proteins. Consequently, RNA interference (RNAi) processes can change the mutation mechanism (2740) by blocking mutated genes from developing into proteins. See the discussion of RNAi at FIG. 69 below. But generally, mutations from the DNA are transmitted via the RNA to create protein structure deformation(s) (2745). Before the SP deformities can present protein function anomalies (2765), the geometric deformations of the protein structures can be "patched" with either a chemical (2755) or a nano product tailored to repair the deformity (2760). Once patched, the repaired protein leads to healthy cell operation (2775). Without the intervention of the patch process, the protein function anomaly will lead to cellular pathology (2770). The drug Gleevec operates to precisely "patch" the tyrosine kinase enzyme by "sitting" in the enzyme's active site to switch off a signal for a cell to grow in cases of the disease chronic myeloid leukaemia (CML). This "patch" model is in fact the paradigm for functional proteomics management of pathological protein operation at the SP level without affecting the DNA of the subject. In the case of CML there is only one protein to repair, but in many diseases unique combinations of protein dysfunctions create the cellular pathology. It is necessary to understand these processes with the assistance of FP simulations.

FIG. 28 describes a dysfunctional proteomic model. After acquiring data and analyzing the data on proteins from gene and protein databases (2815), single nucleotide polymorphism (SNP) combinations are identified (2820) and analyzed (2825). Structural protein deformities are identified (2830) by comparisons with the GPM (2800) and protein dysfunctions (2835) are recognized. A customized pathology model is developed (2840) in which structural proteomic data is reverse engineered from limited information (2845). Data is supplemented from the limited information on protein pathology, and comparisons are made from four-dimensional simulations of optimal protein-protein interaction maps (2810) from the FP model generated by the GPM. Data is interpolated (2850) from the reverse engineering process and supplemented to the analysis of the SP deformities. In this way, we build dysfunctional protein maps of individual pathologies.

A comparison of healthy protein function and an unhealthy FP process is shown in FIG. 29. On the left side, DNA (2900) produces RNA (2905) and amino acids (2915) that then produce protein structures (2925), protein function interactions (2930) and, finally, equilibrium in cellular biology system (2945). However, as shown in the right side of the chart, either exogenous influences (2950) or endogenous influences (2955) may cause DNA damage (2960) which transmits to the RNA (2965) and the amino acids (2970) and manifests as mutant protein structures (2975), pathological protein function (2980) and a specific disease (2985). Genetic mutations are the main cause of genetic diseases. FIG. 30 shows the risk assessment of mutations (3000) by showing SNP combinations, or haplotypes (3010) that are caused by either endogenous sources (3015) of mother (3020) or father (3025) or exogenous sources (3030) such as food (3035) or the environment (such as chemicals, radiation, etc.) (3040).

In order to manage genetic disease, as referenced in FIG. 31, whether as a hereditary factor (3100) or an environmental factor (3110), mutations are identified (3120), protein structure deformations are identified (3130), the genetic disease is diagnosed (3135) and activation (or nonactivation) of specific inhibitors of normal cellular processes (3140) is made, leading to maintenance of a healthy equilibrium (3145).

An individual's pathology assessment, based on an analysis of mutations, is shown in FIG. 32. After DNA micro-array data is acquired from an individual (3200), the individual's haplotypes (SNP combinations) are identified (3210). The dysfunctional SNPs are compared to the healthy FP operation of the GPM (3220). Haplotypes, the combinations of which represent a pathology type, are identified by comparing sets of extra conditional SNPs to the GPM (3230). Once the individual mutations are recognized, the unique vector probabilities of the specific mutation combinations are identified as the cause of a specific pathology (3240). In order to accomplish this complex task of identifying the meaning of an individual's specific haplotypes, and in order to identify the specific pathway pathology, less relevant data is pruned out (3250), by comparison to the healthy FP in the GPM or by comparison to other existing pathologies and their unique mutation sources.

The construction of an individualized haplotypes model is further described in FIG. 33. An individual's custom pathology model is developed (3300) in this figure by collecting DNA microarray data (3310), identifying SNPs (3320), identifying the SNP combinations (haplotypes) (3330), comparing the haplotypes to the GPM (3340), identifying the haplotypes that relate to specific pathology (3350), pruning the haplotype SNP subsets to assess the pertinence to specific pathways of the individual's pathology (3360) and comparing the SNP subsets to pathway protein interaction data (3370). In order for pathologies to be understood, we need to assess their sources. Granting that genetic mutations cause pathologies, our goal is to trace the origins of disease from the pathology, through the proteomic (both functional and structural) operations to the genetic source. This process of understanding the genesis of disease involves a reverse engineering of pathology.

FIG. 34 describes the process of reverse engineering a customized pathology. After identifying the specific pathology (3400), haplotypes are tracked as a source of the pathology (3410). Specific biochemical pathological pathways are identified (3420), and the individual's diseased pathway configurations are compared to the GPM (3430). The overlap of the haplotypes and the GPM FP data is considered and compared (3435), and the range of protein interaction data is narrowed by pruning the combinatorial search space (3440). The scope of haplotypes causing specific pathway pathology is further narrowed (3450) and the SNP combination subsets are tested by interacting with FP pathway protein interaction data in the GPM (3460).

FIG. 35 presents a mutation analysis method. Specific pathologies are identified for specific consequences of a haplotype (3510) after haplotype subsets are identified (3500). The range of specific combinations of haplotype subsets (3520) is narrowed, and probability values are assigned to the specific narrow range of specific mutation combination subsets (3530). Various FP combinations are tested for specific pathologies (3540), and this protein combination data are linked from the GPM to specific pathology (3550). Specific narrow haplotypes subsets for specific pathologies are tested (3560), and mutation conditions specific to a pathology are predicted (3570). Simulations are an optimal format for modeling pathology prediction from FP data.

In FIG. 36, a simulation scenario selection process for pathology prediction is described. Various simulations of pathology causes based on pathway protein function, from both the GPM and haplotype data, are tested (3600). Various simulation scenarios of pathway pathology are then generated by selecting different mutation combination subset input variables (3610). Known GPM-based simulations of protein pathology are identified (3620), and the range of simulation scenarios is narrowed by pruning GPM data of FP interactions as probable cause of specific pathology (3630). The probabilities of pathology causes are sorted by pruning unlikely FP behavior (3640). Contingent scenarios based on the most probable mutation combination subset are created from GPM data on healthy FP and pathological protein pathway data (3650). The most likely mutation combination subset simulation scenario is selected as a predictor of pathology (3660), which is limited to a specific range of probability (3670).

Since unique combinations of SNPs are shared between individuals, typically caused by genetic inheritance in families, there are general haplotypes shared by groups of individuals. FIG. 37 shows the identification process of individuals in these groups that share SNPs and pathologies. The HAPMAP is a database of haplotypes. HAPMAP data on SNPs can be identified and evaluated (3700) using traditional data mining procedures. SNPs are identified in a sample of a number of individuals (3710), and pathologies that are shared by these individuals are identified by sampling the group (3720). The shared set of SNPs between the subsets of individuals is identified (3730). Shared relationships between individuals, such as common relatives, are identified (3740), and the probabilities of specific individuals to obtain a specific genetic disease are statistically analyzed (3750).

The need to identify the combinations of genetic mutations that create mutant proteins which, in turn, cause dysfunctional protein behaviors that are responsible for genetic diseases is just the first part of understanding these diseases. While it is true that the invention of the GPM is important to our functional understanding of the operation of interactive proteins in that it provides a baseline model for the understanding of dysfunctional protein operations, the main goal in this system is to identify the proteomic sources of diseases so that we can develop solutions that will allow us to manage these diseases on the proteomic level. FIGS. 38 to 46 generally discuss the process of customized medicine called pharmacoproteomics. The main objective of individualized medicine is to identify and to precisely describe, through the use of simulations, dysfunctional protein structures for each individual so that we may identify specific solutions to bring each unique pathological cellular pathway to optimum health and to manage genetic diseases at the proteomic level. The scientific community has completed a combination of discoveries that make this system possible.

As shown in FIG. 38, SNPs and haplotypes are identified as the origin of specific pathologies (3800), and data is collected on an individual's DNA with the help of DNA microarrays (3810). IMSAs analyze haplotypes and SNP subsets to identify a specific individual's FP cause of specific pathology (3820). Once the FP source of pathology is identified, the specific protein structure deformities can be identified, which will allow us to construct a customized solution for a particular proteomic pathological cause (3830). The proposed solution is tested by obtaining new DNA microarray data to assess the progress of the solution in the patient (3840), and the customized proteomic solution is further refined (3850).

In FIG. 39 pharmacoproteomic solution generation is described. IMSAs (3910) perform interaction processes with a specific application (e.g., a specific cancer type) by first identifying mutations (3920) (identified by comparing mutant proteins with healthy cells), then by developing a model and simulations of the problem (3940), developing simulations of personalized solutions to repair the mutations (3950), testing the solution for effectiveness by obtaining feedback from the progress of the solution in the patient (3960) and, finally, refining the solution (3970).

The left sequence of FIG. 40 tracks the pathological cause from the cellular system (4000) to cellular pathways (4005), protein function (4010), protein structure (4015), amino acids (4020), RNA (4023) and, finally, to DNA (4025). On the right sequence of FIG. 40, the targeted drug process is described with repair of the genetic damage at the level of DNA (4030), RNA (4035), amino acids (4040), structural proteins (4045), functional proteomics (4050) and cellular system behavior (4055).

In order to develop customized solutions to specific dysfunctional proteomic problems, it is necessary to precisely identify the problem. Since the functional proteomic pathology typically is merely the manifestation of a structural proteomic deformity, identifying the structural deformation is critical to solving the problem. Even if we can identify the mutations and the mutation combinations that create distinctive pathologies, we nevertheless are required to precisely isolate the SP deformity with computer-aided design techniques and with the collection and comparison of data sets from protein databases and the GPM. To identify appropriate solutions, then, the pharmacoproteomic model requires evaluation of the structural and functional proteomic dysfunctions in order to be able to identify appropriate solutions.

FIG. 41 describes a proteomic dysfunction identification and solution selection process. Individualized diseases that build up via cellular damage (and manifest as mutations) (4100) and the dysfunctional proteins and the sources of the pathology are identified (4110) and compared to the GPM in order to assess healthy FP operations of a specific pathway (4120). FP dysfunction(s) are detected (4130), and the dysfunctional parameters are identified (4135). Individualized simulations of probable dysfunction are constructed, and the most probable simulation is selected within specific conditions (4140). Prospective solutions to correct the protein dysfunction at the structural protein deformity level are identified (4145). The defect is then corrected at the FP level (4150).

In FIG. 42, the generation of a solution to SP pathology is delineated. After the dysfunctional SP causing the specific pathology is identified (4200), the precise geometrical deformation configuration in the dysfunctional protein is identified with CAD software (4210). Once the geometrical deformity is structurally recognized, it is possible to tailor a chemical compound that integrates into the protein's geometrical configuration deformation (4220) and thereby to repair the protein deformity that causes the functional proteomic pathway dysfunction (4230). This method manages the disease at the level of proteomic interaction without curing the source of the disease, namely, the genetic mutations themselves.

Because they are genetic diseases, with common genetic inheritances, some pathologies are shared between individuals in the same family or the same community. Consequently genetic diseases that are common to specific groups may be managed by combining specific combinations of medicines which treat specific combinations of shared mutations among a group. Though not considered personalized medicine, the modeling of medicines targeted at groups with inherited diseases is considered to be semi-customized.

In FIG. 43, a semi-custom medicine development process is articulated. Following data collection from specific subpopulations (4300), common pathologies for various subpopulations are aggregated (4310), and specific diseases within substantial sub-groups are selected to efficiently treat (4320). Like in the personalized medicine model, the structure of dysfunctional proteins causing common pathologies is identified (4330), and individuals are tested for common mutations that have a common pathology (4340). Combinations of drugs are finally applied to address a multiple, specific genetic mutation caused by protein structure deformity (4350).

The targeting of combinations of drugs to manage multiple disease-causing mutations may be observed in the example of one form of lung cancer. EGFR, a tyrosine kinase (TK) enzyme, is overabundant in eighty percent of lung cancers and plays a major role in over-stimulating cell division. The drug Iressa, a TK inhibitor, may be useful to limiting EGFR, but for it to be effective, the patient must possess a key mutation. Consequently, Iressa is effective in only a limited number of patients in whom the mutation is present. In another example, the HER-2 protein is a cell-surface receptor protein that plays a role in some forms of breast cancer. The drug Herceptin stops activation of the HER-2 protein in some patients with specific mutations. In both cases, patients must be screened for a combination of genetic mutations in order to assess the potential effectiveness of these drugs against their particular forms of the diseases. The present system introduces models that simulate the operation of proteins, giving researchers more precise tools to "see" the genetic and proteomic causes of disease as well as the effects of particular drugs on these unique combinations of genetic mutations.

FIG. 44 presents a chart of management protocols of genetic pathology that provide solutions to dysfunctional protein structures. In order to "patch" the deformed parts of a dysfunctional protein structure, such as presented in FIG. 23, a universal molecular "paste" is suggested. A more tailored approach is suggested in which a customized chemical compound integrates into the protein geometrical configuration deformity. An even more personalized approach to solving the problem of protein structural geometric deformity is to individually tailor nano-structures that correct the proteomic dysfunction. These structures can be delivered by way of an adenovirus to specific cellular regions. Another interesting model, parallel to the stem cell replacement therapy model, suggests the generation of healthy proteins to substitute for dysfunctional proteins. In a similar approach, synthetic protein is generated to replace the dysfunctional protein to produce healthy FP cellular pathways.

Another model for managing dysfunctional proteins is the application of RNAi techniques, typically via adenovirus, to block the genetic production of malicious proteins. As FIG. 69 illustrates, this protein silencing procedure may be done at the level of the gene or the level of protein production.

In still another model, the body's mechanisms to attack dysfunctional proteins are enhanced. In this paradigm, the immune system is fortified to resist proteomic dysfunctions. In the main methods to manage the FP manifestations of disease summarized above, antibodies carry the respective remedies to the appropriate targets. In addition, vaccines may be customized for particular patients by taking their own cells and fashioning a response that fights particular diseases. The goal of pharmacoproteomics is to develop customized therapies for specific diseases. The use of combinations of the above methods is therefore appropriate in order to tailor specific remedies to specific complex disease problems. Understanding the interoperation of the functional proteomics provides a crucial step toward identifying the causes of genetic disease which is itself preparatory to designing customized therapeutic solutions.

Once the personalized medicinal therapies of pharmacoproteomics are fashioned, they must be tested. In order to test specific proteomic solutions to complex problems, it is necessary to receive systemic feedback. FIG. 45 shows the active feedback process needed to track protein-based medicinal therapy regulation. It is assumed by reductive logic that degenerative diseases change status, that is, degrade. Neurodegenerative diseases and aging illustrate this problem of degradation over time. It is necessary to track this degradation process in the course of administering medicine in order to refine the effectiveness of the medicine. The problem of the degrading source of the mutations is recognized, as well as the need to redevelop solutions (4500). Microarrays are employed to test the assimilation of drugs in a patient over time by taking multiple readings (4510). The information from the microarrays is used to develop an individual model which is then used to track the feedback of the medicine not only for the affected patient but also for other similar patients (4520). The information about the effectiveness of the drug(s) presents feedback data, which allows an analysis of the parameters of the specific mutant protein to repair (4530). Combined with this feedback process of assessing the progress of proposed therapies (4540), personalized medicine is made possible because of the modeling of the functional proteomic dysfunction processes. In a sense, the feedback provided by microarray assessments allows the customized medicine model to "experiment" with each patient's unique set of pathologies by adapting the medicine combinations within a customized protocol.

In FIG. 46 the pharmacoproteomics modeling process is shown using real time simulations for individualized medicine. After multiple protein databases provide information sources to protein pathology (4600), a wet lab provides data sets on protein pathology for computer-based experiments (4605), and simulations are generated of protein pathology from wet lab data sets (4610). Once the SP geometric deformities are identified, the appropriate corrective, such as a chemical compound, is applied to the mutant protein (4620). Protein changes are tested (4630), the drug effects are traced and feedback is obtained (4635), and episodic changes to the protein function are identified (4640). An optimal simulation is selected (4650), and optimal medicine is applied (4655). Once the medicine is applied, more information is obtained on the drug's effectiveness, feedback is obtained, and the process is continually refined.

The most prominent applications of the present functional proteomics modeling system to genetic diseases include degenerative diseases of cancer, neurodegenerative diseases, immunodegenerative diseases and aging. FIGS. 47 to 53 discuss these main disease categories in the context of proteomic interactions.

FIG. 47 describes these main disease classes in the context of cellular problems, proteomic sources, bio-mechanisms and the solutions for each. In the case of most types of cancers, the cellular mechanism is stimulation of cell division, the cause is unique combinations of genetic mutation, the source is endogenous, the solution is to retard, block or prevent tumour development, and the biomechanism is to block, inhibit or disable proteomic mechanisms. In the case of neurodegenerative diseases such as Alzheimer's Disease (AD), Parkinson's Disease (PD) and Huntington's Disease (HD), the cellular mechanism is dysfunctional proteomics, the cause is genetic mutations that contribute to intracellular degradation, the source is endogenous, the solution is to delay onset or to stimulate the growth of cells, and the biomechanism is to block, inhibit or disable proteomic mechanisms.

In the case of immunodegenerative diseases such as forms of arthritis, allergies and diabetes, the problem lies in disequilibrium of the regulatory system—dysfunction of the protecting mechanisms against exogenous diseases leaves patients susceptible to a range of secondary diseases—the cause is cellular degradation, the source is either endogenous (genetic) or exogenous (e.g., a virus that degrades or suppresses the immune system), the solution is to fortify the immune system or to delay accumulation of degradation, and the biomechanism is to fortify biological mechanisms or to block those processes which interfere with healthy operation.

Finally, in the case of aging, the problem lies in the erosion or deterioration of cellular mechanisms, the cause is genetic intracellular mutations (such as in the mitochondria or mitochondrial lining because of oxidation), the source is endogenous, the solution is to delay degradation or stimulate healthy function (such as with antioxidants), and the biomechanism is to block cellular degradation or fortify proteomic mechanisms.

These four degenerative diseases clearly contrast with optimum health, in which biomechanisms are generally in equilibrium. Since the goal of personalized medicine is to provide corrections to genetic dysfunctions, it is useful to identify the healthy functioning of proteins and cellular systems and make comparisons with the range of diseases.

FIG. 48 shows six main neoplasms (cancers) by type, mutation source and oncoproteomic solution. In the case of lung cancer, often stimulated by exogenous factors such as smoking cigarettes, which causes genetic damage that manifests as proteomic mutations, the EGFR tyrosine kinase (TK) enzyme is often present. Overabundant in eighty percent of lung cancers, EGFR over stimulates cell division. Iressa is an angiogenic TK inhibitor. Similarly, in some forms of breast cancers, the HER-2 mutation involves a cell surface receptor protein that is addressed by the antibody-based Herceptin in perhaps twenty percent of cases. Combinations of multiple mutations cause some forms of breast cancers, and must be addressed by a cocktail of medicines specified for each unique mutation.

The B-RAF protein is present in about twenty percent of Colo-Rectal cancers. Erbitux, which is antibody-based, is effective in delaying the progress of the disease, suggesting that multiple proteins affect these cellular processes. The B-RAF protein is also a factor in as many as eighty percent of skin cancers, intracellular mutations of which are sometimes caused by radiation. Kidney cancer, like lung cancer, is caused by EGFR protein surpluses that require a TK inhibitor such as Tarceva or an angiogenic such as Avastin. Finally, in the case of Chronic Myeloid Leukaemia (CML), which presents as an over-generation of white blood cells, chromosomes 9 and 22 break and rejoin into a hybrid 9-22 chromosome. BCR-ABL genes combine to form the BCR-ABL protein, a TK enzyme that produces a signal for the cell to grow. Gleevec is a class of promitotic medicine that acts as a TK inhibitor by filling the gap in the geometrical deformity of the dysfunctional protein created by the genetic mutation. Because there is only one mutation that causes this disease, there is a high rate of neoplasm control from Gleevec therapy applied to those patients with this unique mutation.

All of these examples demonstrate functional proteomic interactions and dysfunctional protein mutations as the cause of disease. Each of these classes of protein dysfunctions requires a different type of solution to be effective for specific combinations of mutations. The present system contains modeling and simulation subsystems that show healthy proteomic operation as well as dysfunctional operation of pathologies and pharmacoproteomic approaches to personalized medicine. It is argued that this general approach is the future of medicine.

Figure 49:
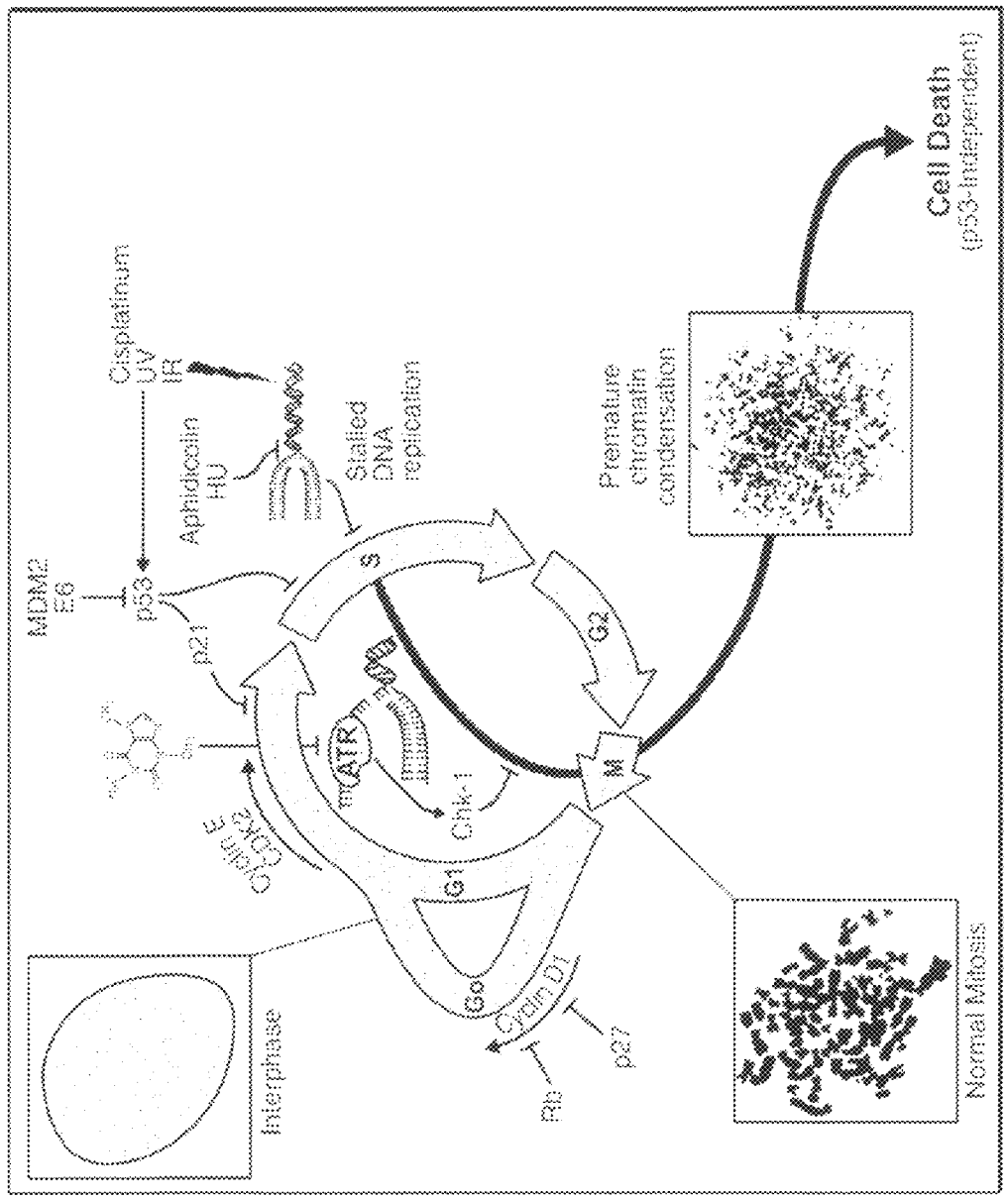
FIG. 49 is a schematic diagram of a dysfunctional cell cycle.

FIG. 49 is a map of the cell cycle comparing normal function and cancer cell generation. Genetic mutations modify the normal cell operation by not limiting the p53 and p21 proteins, which in turn do not limit the rapid growth of cells. Exogenous factors cause mutations in this cellular system that slow normal DNA synthesis. When ATR recognizes that cellular replication is insufficient, it uses Chk-1, which delays mitosis, further delaying the replication of DNA. This representation of a dysfunctional cell cycle illustrates the complexity of dynamic biological system models of disease. This representation is from Brenner and Duggan, *Oncogenomics*, page 309, 2004 (Wiley).

FIG. 50 is a map that reveals the pharmacogenomics of neuronal death mechanisms prominent in neurodegenerative diseases such as AD, PD and HD. The oval in the figure at number 3 indicates a mitochondria. Neurodegeneration is caused by oxidative stress and toxicity involving the mitochondria. Mitochondria are a major source of free radicals that increase oxidation and thus produce degenerative cellular events and eventually cell death. The various approaches to minimize the oxidative process of the mitochondria include blocking of glutamate at 1, inhibiting NMDA receptors at 2, enhancing energy metabolization by using agents such as creatine at 3, decreasing free radicals by using enzymatic inhibitors at 4, utilizing anti-apoptotic molecules at 5, and applying anti-aggregate molecules at 6. This figure, intended to illustrate neurodegenerative processes, is taken from Licinio and Wong, editors, *Pharmacogenomics*, page 354, 2002 (Wiley). The intracellular processes of neurodegeneration are similar to processes that cause aging.

FIG. 51 describes the functioning of a human immune system. The main implication of this complex process is that at specific nexus points, a dysfunction, created by a combination of mutations, will create pathology. These genetic diseases of the immune system derive from two main effects: either they do not perform the main task of keeping exogenous pathogens at bay, or they actually attack the host body. Diseases of Rheumatoid Arthritis, Lupus and forms of Diabetes are examples of the latter. Suppression of the immune system produces the susceptibility to numerous bacteriological and viral pathogens. If genetic mutations, triggered by endogenous or exogenous sources, affect the production of T-cells or B-cells, the healthy operation of the immune system as articulated in this figure is disabled or degraded. The source for this figure is http://uhavax.hartford.edu/BUGL/immune-.htm. This figure illustrates the self-organizing behavior of a complex system within functional proteomics.

FIG. 52 shows the "pathophysiologic scheme of sickle cell disease." In this example, the genetic mutation causes the normally healthy GAG gene to transcribe to the GTG mutation. This condition manifests as a deformed red blood cell that can be very painful and injurious. A potential remedy would be to correct the deformed protein created by the GAG gene with a medicine that allows it to function in a healthy manner. Modeling techniques allow us to consider the source of the problem from a functional proteomic viewpoint and to design drugs to correct the structural proteomic deformity. This figure is from Licinio and Wong, editors, *Pharmacogenomics*, page 237, 2002 (Wiley).

FIG. 53 shows the concepts generated in FIG. 50 involving the mitochondria. This figure delineates the pathology of gerontoproteomics, or the functional processes of aging. There are a number of causes of cellular decay and death that may manifest as aging. Accelerated aging can occur in a particular cell line, such as skin cells, because of overexposure to the sun which stimulates mutations. These processes involve the degradation or degeneration of mitochondrial membrane integrity, cellular wall decay, telomere (the tips of chromosomes) decay or the accumulation of mitochondrial DNA mutations. FP models combine these various factors to trace the causes of and discover ways to retard, the effects of aging. Aging manifests in a suppressed immune system as well as other degenerative diseases. Mitochondrial membrane integrity and cellular wall integrity degradation is caused by oxidation and exposure to free radicals that occurs in the process of producing energy (ATP) for the cell. Intracellular mechanisms cause dysfunctional processes that can be inhibited with the use of proteins such as antioxidants; these correct for the oxidative effect of free radicals produced by the mitochondria. The present system makes it possible to identify and enhance free radicals mechanisms of cellular respiration and thus constitutes a key way to retard the aging process.

One strategy to slow the aging process is to slow the mitochondrial DNA (mtDNA) mutation rate which then affects oxidation. Reducing the circular feedback mechanism of reduced ATP increases free radicals, which increases mtDNA mutation accumulation and in turn reduces ATP; doing so makes it possible to slow the effects of aging. Though mtDNA, which consists of thirteen genes, controls some mitochondrial operation, nuclear DNA control mtDNA regulation. Therefore, to address the problem of mitochondrial DNA mutations, proteins will be configured to block the effects of the accumulation of the mutations in both mtDNA and nuclear DNA.

Another model to slow the aging process involves the telomeres. Telomeres are "pre-programmed" to copy the DNA a specific number of times before decaying. After this period, mutations begin to accumulate. In order to extend the replication process in which the telomeres play a prominent part, several strategies are applied to affect the mechanisms involved in gene replication. First, the enzyme responsible for DNA replication will be refined and enhanced in order to increase the precision of its function. Second, the effect of this increase in precision will be more accurate replication of telomeres, in effect extending their effective copying life, which minimizes mutations and limits the corrosive effects of the aging process. Finally, in order to increase the accuracy and precision of the DNA replication process, it is necessary to identify and enhance the proteins involving RNA replication precision. A combining of these strategies which are identifiable and solvable using the present system forms the groundwork for gerontoproteomics.

IMSAs employ multiple techniques to build functional proteomics models. The Monte Carlo (MC) simulation method breaks down random data sets into clusters for analysis over time sequences. The Bayesian theory is used to simulate experiments in which an early phase will inform and guide a later phase; this is useful in reorganizing and refining the model generated by accumulating data sets over time. FIG. 54 is a chart showing the application of hybrid modeling techniques involving MC and Bayesian techniques to proteomic simulations. Hybrid techniques are useful in the application of IMSA operations as they build molecular models and simulations.

In the upper left grid of the chart in FIG. 54, the GPM is assembled by using a combination of the small cluster and initiation Bayes process in order to build a self-organizing map. In the upper right grid, individual mutation maps are initiated using big cluster MC models which combine with the initiation Bayes process. Because the MC cluster is small (divided), it is possible to use parallel processing to accelerate the simulation, while a coarse grained approach uses a sequential process. In the lower left grid, small cluster MC is combined with the later phases of Bayesian analysis in order to refine and constantly reorganize the GPM. Since the GPM is a developmental model that undergoes continual reorganization as new functional proteomic information is made available, such combination of techniques is optimal for this modeling. In the lower right grid, big cluster MC is combined with refinement Bayesian analysis in order to produce refined individual mutation maps, which require the acquisition and analysis of many data sets.

FIGS. 55 to 65 apply to the development of proteomic models using IMSAs. FIGS. 55 to 58 delineate normal FP modeling, FIGS. 59 to 62 illuminate pathological modeling of dysfunctional proteomics, and FIGS. 63 to 65 elucidate pharmacoproteomic modeling.

FIG. 55 describes the modeling system architecture. A hypothetical model is generated (5500) and connected to a database (5510) or multiple distributed databases. The database is accessed by intelligent mobile software agents (IMSAs) (5520), which connect to a simulation engine (5530) and to a visualization engine. The IMSAs are the key operating component integrating the database and the simulation engine. The visualization engine represents the manifestation of the simulation engine. This hypothetical model presents an initial position from which to develop simulations based on new data sets. Though a simulation is built on the data used to model it, the initial generation of a simulation is based on hypothetical models used in the past; future models are built by analogy to the category of data presented. Without a hypothetical model, simulations rely on self-organizing maps, which have originating and transformative phases.

The general modeling system architecture is presented as a foundation for organizing complex data sets based on self-organizing sets of the GPM, individual mutation combinations and pharmacoproteomics, each of which is a category of optimization problem. Consequently, various techniques are employed to model these problem categories as presented in this system.

IMSAs, core components of this modeling system, are software agents that move from machine to machine to collect and analyze data and generally build FP models. The IMSAs operate in a multi-agent system (MAS) as specialized sophisticated software entities that cooperate or compete to solve complex computational problems. In the context of this system, the IMSAs employ hybrid EC techniques and other computational techniques such as MC and Bayesian approaches and artificial neural networks (A-NN) in mobile software code that is programmed to model and simulate complex FP behaviors.

In general, EC consists of computational processes which emulate the theory of biological evolution, in which software algorithms or software programs are "bred" using principles of natural selection, mutation and sexual reproduction. The aim is to develop multiple runs of computer programs which lead, at each successful generation of development, to the selection of the strongest possible outcomes. Over time, this process is intended to identify solutions to hard problems. Given substantial computer hardware capabilities, the use of these computational strategies and techniques yields rapid solutions in real time since many generations of computer programs can be bred to solve problems quickly.

Multiple IMSAs may work together to solve complex problems. An IMSA will send signals to other IMSAs requesting information on or analysis of a problem. In order to solve a combinatorial optimization problem more quickly, multiple IMSAs will divide the problem into parts or solve it in multiple phases. In this further embodiment of the system, multiple IMSAs perform functions to complete a task. Use of multiple IMSAs that employ various hybrid EC techniques simultaneously to solve aspects of larger problems, allows the complex modeling of the GPM, individual mutation combination identification, and pharmacoproteomics to be performed. By employing modular EC techniques, IMSAs seamlessly integrate and automatically update AI for advanced IMSA operations. The central challenge share by these main functions is how to identify the classification of data sets in an ordered way. Because organizing very large data sets requires experimentation, in silico techniques are utilized in conjunction with wet lab procedures to decipher, via a process of trial and error, initial organizational models. Hybrid EC techniques, as used by IMSAs, are expected to be a major resource for the biological sciences in coming generations.

FIG. 56 describes a model generation process using IMSAs. After an IMSA identifies what objects to include in the search space (5600), the search agent actively searches databases (5610). The IMSA analyzes similarities of objects by comparing object differences (5620), develops initial parameters of object sets using cluster analysis (5630) and sorts and organizes groups of clusters by constantly comparing pairs (5640). The IMSA generates a self-organizing map (5650) and compares the map origination to a frame of reference map using a Bayesian process (5660). The IMSA builds a map by adding data sets (5670), which it then updates and reorganizes as the data require.

The pathway generation process is described in FIG. 57. The IMSA tests pathway probabilities using artificial neural networks (A-NN) (5710) after first generating a pathway candidate (5700). A-NNs are particularly useful in training IMSAs because they allow the refinement of specific EC techniques. The IMSA optimizes values of the pathway using A-NN (5720) and modifies pathway vectors (5730) and values. The IMSA develops an optimal range of equilibrium conditions using EC (5740) and prunes the optimal range of options by comparing pathway ranges and selecting the best option (5750). The optimal protein pathway simulation data informs the GPM (5760), which is then updated with the new information.

An optimal simulation generation process using IMSAs is described in FIG. 58. A simulation is generated using an IMSA by collecting data from the GPM and from protein pathway information using MC techniques (5800). The IMSA develops a protein pathway simulation using hybrid MC and Bayesian techniques as discussed in FIG. 54 (5810). The IMSA drafts multiple generations of simulations by using multiple data sets and EC learning techniques (5820). After the IMSA fetches more data from the databases (as they become available) (5830), it generates multiple simulation scenarios to assess the range of data parameters using EC (5840). The IMSA develops contingency scenarios using multivariate data sets of highest probabilities (5850). The IMSA then develops simulation selection methodology for selecting an optimal simulation from specific priority conditions (5860). The IMSA selects the optimal simulation (5870). Multiple computational techniques are employed at different stages of the process to maximize solution generation success.

Whereas the general simulation construction is performed as described above, the pathology protein pathway simulation generation model using IMSAs is described in the following figures. In FIG. 59, after a protein pathway is identified for analysis (5900), an IMSA creates a simulation to compare mutant protein combinations to the GPM's healthy pathway data (5910). The IMSA analyzes the differences between healthy and dysfunctional protein pathways (5920) and then compares combinations of mutant proteins to healthy protein pathway operation (5930). The IMSA prunes mutant proteins' unlikely pathway functioning from the healthy protein pathway information in the GPM by comparing them (5940). An optimal pathway of dysfunctional proteins is then identified (5950).

FIG. 60 describes the process of optimal dysfunctional protein pathway simulations using IMSAs. An IMSA generates dysfunctional protein pathway simulations by accessing haplotype data on combinations of mutations (6000) and then drafts dysfunctional protein pathway simulations using EC techniques (6010). The IMSA tests dysfunctional protein pathways using A-NN techniques (6020) and analyzes main vectors of possible pathways (6030). The IMSA optimizes values of dysfunctional protein pathway simulations by comparing to healthy pathways and prunes suboptimal options (6040). The IMSA narrows the range of conditions of values using A-NN (6050) and generates multiple scenarios of dysfunctional protein pathway simulation by applying multivariate analysis (6060). The IMSA creates a metamethodology for the selection of an optimal dysfunctional protein pathway simulation (6070) and makes a final selection.

FIG. 61 shows the process of identification of mutant protein(s) using IMSAs. After the IMSA collects microarray data on individual mutations (6100), the IMSA identifies combinations of mutations that cause particular pathology (6110). The IMSA identifies the dysfunctional protein pathway by comparing individual mutant protein data to GPM healthy simulations (6120). The IMSA then identifies mutant proteins in the dysfunctional protein pathway (6130) and the specific dysfunctional protein structure deformity topology (6140). The IMSA assists the computer-aided design (CAD) of the mutant protein structure and the simulation of dysfunctional protein pathway interactions (6150). The IMSA identifies ways to block the mutant protein to bring the pathway to normal function (6160). This may be done by identifying binding sites and ligand potentials and designing the appropriate protein to block the docking of mutant (and maliciously-behaving) proteins. The IMSA creates a dysfunctional protein database (6170) and imports dysfunctional protein pathway data sets into the database (6180).

In FIG. 62 the mutation combination generation and selection process using IMSAs is described. An IMSA identifies unique sets of combinations of an individual's mutations (6200) using microarray data. The IMSA compares unique sets of mutation combinations to the GPM's healthy protein function (6210). The IMSA tests combinations of mutations by comparing generations of simulations (6220). The IMSA identifies an optimal combination of mutations (6230) responsible for a particular pathology and generates a general mutation map (6240) for the patient. Of course, once the haplotypes are identified, it is necessary to develop solutions to the problem mutations. FIG. 63 shows IMSA use in the gene-blocking process of mutant proteins which cause pathology. After identifying the mutant protein (6300), an IMSA identifies the genetic source of the mutant protein (6310). The IMSA then designs RNA interference to block mutant protein generation (6320), and the gene is effectively turned off that generates the mutant protein (6330). FIG. 69, below, specifies RNA interference techniques in greater detail. However, there are multiple methods to block a mutant protein generation and operation, as discussed above at FIG. 61.

In FIG. 64, the solution to the problem of protein mutations using IMSAs is described. After identifying the mutant protein (6400), an IMSA describes the protein's structure topology (6410). The IMSA compares the mutant protein structure topology with healthy protein structure topology (6420) and calculates how to develop a compound to complement the mutant protein topology (6430) similar to the illustration in Phase three of FIG. 23. The IMSA designs a unique compound to patch the mutant protein (6440). The IMSA identifies multiple mutant proteins and develops multiple compounds to patch each of these (6450). Taken together, the combination of multiple mutant protein patches comprises a solution to the pathology (6460), and the pathology caused by the mutant proteins is managed (6470) as long as the therapy is applied.

Once the FP problem is identified and the solution designed and applied, it is necessary to test it. FIG. 65 describes the pharmacoproteomic testing process using IMSAs. An IMSA generates simulations to track a customized chemical compound (6500) and prunes optimal values and ranges of simulations using A-NN and EC techniques (6510). The IMSA tests various simulations by comparing individual protein data on the progress of custom solutions (6520) and uses parallel computation and individual simulation processing in order to accelerate the process (6530). The IMSA evaluates whether the custom protein solution is working (6540), recommends refinement of the protein solution (6550) and refines the mutant protein solution (6560).

Several main types of simulations in the present system correspond to the three main problem categories of the GPM, protein mutation analysis and pharmacoproteomics. FIG. 66 lists these main simulation types. See also the discussion below at FIG. 71. GPM healthy FP operation simulations consist of (1) FP interaction simulations, (2) FP pathway scenarios based on equilibrium variables using simulations, (3) optimal pathway selection process using simulations, (4) reverse engineering simulations tracing from (healthy) FP to SP (and to gene(s)), (5) FP simulations that use partial information based on probabilities, and (6) simulations that inform and update the GPM about analytical relations.

Dysfunctional protein pathway simulations consist of (1) mutation combination simulations, (2) reverse engineering simulations from disease to genetic mutation(s), (3) variable based scenario simulations based on dysfunctional protein operations, (4) simulations of pathway scenarios of dysfunctional protein interactions, (5) optimal pathway selection process simulations, and (6) simulations to identify the SP profile of mutant protein(s) from dysfunctional pathway analyses.

Active and interactive pharmacoproteomics process simulations consist of (1) simulations to design a custom solution to (combinations of) mutant protein topologies, (2) simulations to test solution candidates using pathway scenarios and updated feedback data, and (3) simulations to refine solutions using real data from the solution candidate feedback process.

Since Monte Carlo (MC) statistical simulation techniques are suited to molecular modeling processes, FIGS. 67 and 68 describe the use of the MC to FP simulation approaches. In FIG. 67 the MC statistical technique is applied to protein data organization in a dynamic process. After collecting initial protein data using a refined MC method (6700) to divide the clusters into smaller groups for analysis, the data sets are sampled, analyzed and ordered (6710). Probability density functions (PDFs) are identified by assessing values (6720), and random data sets are pruned (6730). More protein data is collected in the context of protein-protein interactions in protein pathways (6740). PDFs are identified (6750), and the data is pruned (6760). The data is resorted to recognize patterns in the process over time (6770). The MC process statistically describes protein model dynamics (6780).

In FIG. 68, the MC statistical technique is applied to protein mutation data organization in a dynamic process. After initial protein mutation data using a coarse MC method is collected (6800), the data sets are sampled, analyzed and ordered (6810). PDFs are identified by assigning values (6820), and PDFs are sorted according to optimum combinations of sets of mutations (haplotypes) (6830). More protein mutation data are collected in the context of protein dysfunction pathways (6840), and data are resorted to recognize patterns in the process over time (6850). The data are resorted to recognize haplotype patterns linked to pathology (6860), and protein structure topology of dysfunctional proteins is identified (6870). By employing these techniques, typically with the use of IMSAs, it is possible to model the complex molecular interaction processes in order to identify healthy and dysfunctional protein behaviors.

FIG. 69 describes the RNA interference process used in silencing the production of a protein. Mutated proteins are identified (6900), and the source of the mutations is identified in the genes (6910). The malicious gene is targeted for silencing with RNAi (6915). An RNA-induced silencing complex (RISC) is created (6930) using small interfering RNA (siRNA) expressed from Polymerase III (pol III) promoters (6920 and 6935). The RISC is applied to messenger RNA (mRNA) (6945), and the gene sequences that are complementary to siRNA are silenced (6965). Another way to silence the gene sequence using the siRNA is to generate siRNAs from long, double-stranded RNAs (6940) and enter the RNA interference pathway (6960). Finally, since pol III promoters can produce micro RNAs (miRNAs) by forming single-stranded RNAs, they can turn off genes at the level of protein synthesis (6950) and thus suppress protein mutations (6970). These may be delivered by adenoviruses or antibodies to the particular DNA, RNA or protein locations.

FIG. 70 describes the GPM operation in more detail. After inputting data sets from protein databases (7000) and the HGP (7010) to the PPT (7020), the GPM (7030) is updated with SP data from the PPT. It is from the GPM that FP simulations (7040) and dysfunctional protein simulations (7050) are generated. FP and dysfunctional protein simulations are compared. However, the GPM is updated by information from the analysis of the FP simulations as well. In addition, the GPM functional data on proteins update the PPT by providing improved categorization.

FIG. 71 illustrates the feedback mechanisms of the GPM. After SP data sets (7100) are input, FP data reorganize the SP data by using filters (7110) that compare and classify the SP data according to function. This process is similar to understanding the syntax of language based upon an understanding of semantics. A hypothetical protein model is built (7120) which represents the GPM's first level. Pathwaycentric protein-protein interaction simulations are generated (7130) from the hypothetical model. In this initial simulation, hypothetical scenario testing of combinatorial probabilities (7140) is conducted.

At this point in the operation of the GPM, the analysis of the FP scenarios informs the reorganization process of the SP data sets (7110) while it also informs the GPM (7150) at a second level. Further analysis of SP data from the simulations re-sorts and reclassifies FP data (7160). Though SP data inform FP models, FP data facilitate the organization of SP and gene data sets through filtering and re-sorting processes. This analysis of the SP data then informs the SP inputs (7100), and the GPM is updated with increased probabilistic certainty (7170) at the third level. Simulations are then generated (7130) from this level of the GPM with greater efficiency and certainty. In this evolutionary way, the GPM is updatable and accumulates more detail about FP processes. While there are limits to the completeness of the GPM, the multiple passes of the GPM operation make the GPM an evolvable, dynamic meta-model from which simulations are generated.

From the GPM it is possible to generate simulations that provide a hypothetical testing approach to understanding protein operations. The simulations available from GPM data analyze not only a single protein's multiple vectors and variables on a cellular pathway but also the complex interoperation of multiple proteins. In these multiple probabilistic scenarios, various values and training weights change. The simulations order and constantly reorder data sets by rapidly testing probabilities within limited ranges in order to identify various aspects of the problem.

Since protein binding is a key protein function that affects degenerative diseases, it is important to model aggregation scenarios between proteins. Such simulations identify docking sequences, optimal binding criteria, and binding blockage potentials as well as drug interaction probabilities. The application of combinatorial geometry to these classes of aggregation problems assists in computer-aided identification and design of virtual small molecules.

A range of functional simulations is generated from information in the GPM, which, taken together, provides a powerful toolkit for biochemical researchers. In addition to forward motion simulations, there are also backward motion simulations (from effect to cause). Reverse simulations trace multiple probable causes of a dysfunction. Forward simulations trace multiple pathway-centric protein interactions. Multivariate simulations, generated from different prospective assumptions, present different scenarios within varied probabilistic ranges. Simulations may focus on various types of proteins, such as on binding aspects of specific macromolecules, or may focus on different angles of a binding site in order to analyze scenarios and probabilities. Simulations also accommodate and emulate the complex feedback mechanisms of protein-protein system adaptation, effects of which are not available in SP analyses. Simulations also analyze the potential pathways of protein behavior under specific disequilibria conditions. Finally, comparative analysis of simulations provides valuable information about dysfunctional operation as well as sharpens our understanding of functional protein-protein operations. These approaches assist in the simulation of protein behavior predictions.

Simulations are time sensitive representations of systems of interactive molecular protein phenomena. Rather than simulate protein phenomena in a time-consistent way, FP simulations present time-asynchronous processes. Specific processes are accelerated or decelerated within specific equilibria conditions. Identification and understanding of the enzyme processes which may accelerate a protein pathway reaction a thousand-fold are central to understanding threshold event catalysts and the challenges of modeling these processes. The way that simulations are time modulated, then, represents a novelty in the process of modeling functional proteomics.

Finally, as we have seen in the evolvability of the GPM, multiple generations of simulations are required to accurately represent protein functional relationships. This process of simulation refinement is limited by the quality and quantity of information about pathways and FP interactions.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

I claim:

1. A bioinformatics system for functional proteomics modeling, the system comprising:
a computer;
computer modeling program code configured to access at least one database;
at least one computer database configured to receive and access data involving protein and genetic information;
wherein a first computer modeling subsystem develops an evolvable Global Proteomics Model (GPM), which accesses data from the Human Genome Project and protein and genetic databases of structural proteomics and which supplies a foundation for generating simulations of healthy protein-protein interactions;
wherein a second computer modeling subsystem generates simulations from data on an individual's dysfunctional proteins and from data on the individual's genetic mutations to identify the operation and source of individual diseases in dysfunctional protein-protein interactions; and
wherein a third computer modeling subsystem generates simulations for pharmacoproteomics from data on the individual's dysfunctional proteins and from comparison to data in the GPM, in which prospective drug targets are modeled for optimum effectiveness for individualized therapy.

2. A bioinforrnatics system of claim 1:
wherein the system employs intelligent mobile software agents (IMSAs) which operate in a multi-agent system (MAS) in order to carry out computational operations;
wherein the IMSAs access the at least one database to provide data sets to the modeling program.; and
wherein the modeling program builds models and simulations of protein interactions.

3. A bioinformatics system of claim 2:
wherein the IMSAs work together by sharing data and program code to process computations in order to solve complex functional proteomics (FP) optimization problems.

4. A bioinformatics system of claim 2:
wherein the simulations generated by IMSAs in the three main categories of FP modeling, dysfunctional proteomic modeling and pharmacoproteomics modeling facilitate the emulation and reconstruction of complex protein interaction networks.

5. A bioinformatics system of claim 1:
wherein the GPM accesses data from genetic and structural proteomics databases to develop a functional proteomics model for understanding general protein-protein interactions; and
wherein the GPM is updated by the most recent data and analyses of genetic databases, including the Human Genome Project, and structural proteomics databases.

6. A bioinformatics system of claim 1:
wherein the dysfunctional protein simulations are generated from data sets involving at least one individual's dysfunctional protein interactions.

7. A bioinformatics system of claim 1:
wherein the pharmacoproteomics simulations are organized, once a disease is analyzed via proteomics simulations, to analyze the structure of dysfunctional proteins.

8. A. bioinformatics system. of claim 1:
wherein the computer is programmed to design a biological or chemical compound by accessing the geometrical configurations of each dysfunctional protein's structure and by generating the specifications for a drug target that are constructed from the pharmacoproteomics simulation and designed to apply to the dysfunctional protein.

9. A bioinformatics system of claim 1:
wherein the computer system accesses the GPM and other database information sources to generate simulations that emulate molecular protein interactions; and
wherein the simulations have multiple vectors and scenarios that arc organized by the computer modeling program.

10. A bioinformatics system of claim 1:
wherein the GPM is used by the computer as a source of comparison to assemble information about dysfunctional protein behavior.

11. A bio informatics system of claim 1:
wherein the drug targets are analyzed and refined by the pharmacoproteomics modeling system by comparing the geometric configurations of the compounds to healthy proteins in the GPM.

12. A bioinformatics system of claim 1:
wherein the three modeling subsystems are applied and processed in a distributed computer network.

13. A bioinformatics system of claim 1:
wherein the three modeling subsystems are configured to perform separately.

14. A bioinformatics system of claim 1:
wherein the computer models is applied to create drug targets to apply to dysfunctional proteins in the disease categories of oncoproteomies, immunoproteomics, neuroproteomics and geronotoprotemics.

15. A method for managing a bioinformatics modeling system for functional proteornics modeling, the method comprising:
processing information via a computer using; computer program code configured to access at least one database and to build a computer model; and
at least one computer database configured to receive and access data involving protein, and genetic information and organized to process and store biological data;
the method further comprising the steps of:
constructing an evolvable Global Proteomics Model (GPM) with a first computer modeling subsystem, by accessing data from the Human Genome Project and protein and genetic databases of structural proteomics and by generating simulations of healthy protein-protein interactions;
generating simulations with a second computer modeling subsystem from data on an individual's dysfunctional proteins and from data on the individual's genetic mutations by identifying the operation and source of individual diseases in dysfunctional protein-protein interactions; and
generating simulations with a third computer modeling subsystem for pharmacoproteomics from data on the individual's dysfunctional proteins and from comparing to data in the GPM, by modeling prospective drug targets for optimum effectiveness for individualized therapy.

16. The method of claim 15, further comprising the step of:
analyzing the structure of dysfunctional proteins after a disease is deciphered by proteomics simulations by accessing the pharmacoproteomics simulations.

17. The method of claim 15, further comprising the step of:
programming the computer to design a biological or chemical compound by accessing geometrical configurations of each dysfunctional protein's structure and by generating specifications for a drug target that is constructed from the pharmacoproteomics simulation and designed to apply to the dysfunctional protein.

18. The method of claim 15, further comprising the steps of:
configuring the computer system to access the GPM and other database information sources to generate simulations that emulate molecular protein interactions; and
organizing the simulations with multiple vectors and scenarios by running the computer modeling program.

19. The method of claim 15, further comprising the step of:
analyzing and refining the drug targets developed by the pharmacoproteomics modeling subsystem by comparing geometric structures of the drug targets to healthy proteins in the GPM.

20. The method of claim 15, further comprising the step of:
applying the method to create drug targets to apply to dysfunctional proteins in the disease categories of oncoproteomics, immunoproteomics, neuroproteomics and geronotoproteomics.

* * * * *